(12) United States Patent
Deng

(10) Patent No.: US 10,073,071 B2
(45) Date of Patent: Sep. 11, 2018

(54) HEATING SYSTEM

(71) Applicant: David Deng, Diamond Bar, CA (US)

(72) Inventor: David Deng, Diamond Bar, CA (US)

(*) Notice: Subject to any disclaimer, the term of this patent is extended or adjusted under 35 U.S.C. 154(b) by 538 days.

(21) Appl. No.: 14/702,465

(22) Filed: May 1, 2015

(65) Prior Publication Data
US 2015/0233883 A1    Aug. 20, 2015

Related U.S. Application Data

(62) Division of application No. 13/155,348, filed on Jun. 7, 2011, now Pat. No. 9,021,859.

(60) Provisional application No. 61/352,327, filed on Jun. 7, 2010, provisional application No. 61/421,541, filed on Dec. 9, 2011, provisional application No. 61/352,329, filed on Jun. 7, 2010, provisional application No. 61/473,714, filed on Apr. 8, 2011.

(51) Int. Cl.
    *G01N 33/00*    (2006.01)
(52) U.S. Cl.
    CPC .................... *G01N 33/0036* (2013.01)
(58) Field of Classification Search
    CPC ..... G01N 33/0036; F23D 11/38; F23D 14/48; F23D 14/64; F23D 17/00; F23D 2900/14481; F23N 1/007; F23N 2035/22; F23N 2035/24; F23Q 9/045; F24C 3/12; F24D 2200/04; F24H 9/2064
    USPC .............. 73/23.2; 126/25 R, 39 R, 344, 512; 34/524
    See application file for complete search history.

(56) References Cited

U.S. PATENT DOCUMENTS

| | | |
|---|---|---|
| 188,740 A | 3/1877 | Murphy |
| 743,714 A | 11/1903 | Guese |
| 1,051,072 A | 1/1913 | Bradley |
| 1,216,529 A | 2/1917 | Wilcox |
| 1,574,234 A | 2/1926 | Cumner |
| 1,589,386 A | 6/1926 | Harper |
| 1,639,115 A | 8/1927 | Smith |
| 1,639,780 A | 8/1927 | Mulholland |
| 1,697,865 A | 1/1929 | Hahn et al. |
| 1,729,819 A | 10/1929 | Campbell |
| 1,755,639 A | 4/1930 | Fawcett |
| 1,860,942 A | 5/1932 | Morse |
| 1,867,110 A | 7/1932 | Signore |

(Continued)

FOREIGN PATENT DOCUMENTS

| | | |
|---|---|---|
| CN | 2167287 Y | 6/1994 |
| CN | 2421550 | 2/2001 |

(Continued)

OTHER PUBLICATIONS

Machine translation of CN 101881481 filed Nov. 10, 2010, three pages.*

(Continued)

*Primary Examiner* — Daniel S Larkin
(74) *Attorney, Agent, or Firm* — Innovation Capital Law Group, LLP; Vic Lin

(57) ABSTRACT

A heating system can include certain pressure sensitive features. These features can be configured to change from a first position to a second position based on a pressure of a fuel flowing into the feature. These features can include, fuel selector valves, pressure regulators, burner nozzles, and oxygen depletion sensor nozzles, among other features.

10 Claims, 49 Drawing Sheets

(56) References Cited

U.S. PATENT DOCUMENTS

| | | |
|---|---|---|
| 1,961,086 A | 5/1934 | Sherman et al. |
| 2,054,588 A | 9/1936 | Stephens |
| 2,088,685 A | 8/1937 | Birch |
| 2,095,064 A | 10/1937 | Harper |
| 2,108,299 A | 2/1938 | Steffen |
| 2,120,864 A | 6/1938 | Kagi |
| 2,160,264 A | 5/1939 | Furlong |
| 2,161,523 A | 6/1939 | Moecker, Jr. et al. |
| 2,231,460 A | 2/1941 | Barman |
| 2,319,676 A | 5/1943 | Guelson |
| 2,354,286 A | 7/1944 | Whaley, Jr. |
| 2,380,956 A | 8/1945 | Evarts |
| 2,397,670 A | 4/1946 | Krugler |
| 2,422,368 A | 6/1947 | Ray |
| 2,443,892 A | 6/1948 | Caparone |
| 2,464,697 A | 3/1949 | Logan et al. |
| 2,518,894 A | 8/1950 | Humbarger et al. |
| 2,556,337 A | 6/1951 | Paille |
| 2,560,245 A | 7/1951 | Ramsaur et al. |
| 2,578,042 A | 12/1951 | Chandler |
| 2,588,485 A | 3/1952 | Clarke et al. |
| 2,630,821 A | 3/1953 | Arey et al. |
| 2,641,273 A | 6/1953 | Siebens |
| 2,661,157 A | 12/1953 | Reichelderfer |
| 2,678,066 A | 5/1954 | Carter |
| 2,685,294 A | 8/1954 | Gold et al. |
| 2,687,140 A | 8/1954 | St. Clair et al. |
| 2,693,812 A | 11/1954 | Jones et al. |
| 2,716,470 A | 8/1955 | Focht |
| 2,750,997 A | 6/1956 | Reuter |
| 2,817,362 A | 12/1957 | Antrim, Jr. |
| 2,829,674 A | 4/1958 | Segelhorst et al. |
| 2,844,166 A | 7/1958 | Edman |
| 2,853,098 A | 9/1958 | Fritzsche |
| 2,899,980 A | 8/1959 | Loebel et al. |
| 2,905,361 A | 9/1959 | Noall |
| 2,907,348 A | 10/1959 | Gerteis |
| 2,966,920 A | 1/1961 | Oglesby et al. |
| 2,969,924 A | 1/1961 | Jay |
| 3,001,541 A | 9/1961 | St. Clair et al. |
| 3,032,096 A | 5/1962 | Stout |
| 3,054,529 A | 9/1962 | Billington |
| 3,067,773 A | 12/1962 | Olander |
| 3,083,721 A | 4/1963 | Matthews et al. |
| 3,100,504 A | 8/1963 | Kauer, Jr. |
| 3,115,330 A | 12/1963 | Dollison |
| 3,120,243 A | 2/1964 | Allen et al. |
| 3,139,879 A | 7/1964 | Bauer et al. |
| 3,207,169 A | 9/1965 | Miller |
| 3,244,193 A | 4/1966 | Loveless |
| 3,282,323 A | 11/1966 | Katz et al. |
| 3,331,392 A | 7/1967 | Davidson et al. |
| 3,357,443 A | 12/1967 | Brumm |
| 3,386,656 A | 6/1968 | Bergquist |
| 3,417,779 A | 12/1968 | Golay |
| 3,430,655 A | 3/1969 | Forney |
| 3,504,663 A | 4/1970 | Edwards |
| 3,550,613 A | 12/1970 | Barber |
| 3,552,430 A | 1/1971 | Love |
| 3,577,877 A | 5/1971 | Warne |
| 3,578,015 A | 5/1971 | Andersen |
| 3,578,243 A | 5/1971 | Love |
| 3,590,806 A | 7/1971 | Locke |
| 3,630,652 A | 12/1971 | Nutten et al. |
| 3,633,606 A | 1/1972 | Hay |
| 3,654,948 A | 4/1972 | Nelson |
| 3,693,655 A | 9/1972 | Frisk |
| 3,734,132 A | 5/1973 | Kuhnelt |
| 3,747,629 A | 7/1973 | Bauman |
| 3,768,514 A | 10/1973 | Goto |
| 3,800,830 A | 4/1974 | Etter |
| 3,802,454 A | 4/1974 | Kleuters |
| 3,804,109 A | 4/1974 | Martin et al. |
| 3,814,570 A | 6/1974 | Guigues et al. |
| 3,814,573 A | 6/1974 | Karlovetz |
| 3,825,027 A | 7/1974 | Henderson |
| 3,829,279 A | 8/1974 | Qualley et al. |
| 3,843,310 A | 10/1974 | Massi |
| 3,884,413 A | 5/1975 | Berquist |
| RE28,447 E | 6/1975 | Bonner et al. |
| 3,939,871 A | 2/1976 | Dickson |
| 3,977,423 A | 8/1976 | Clayton |
| 4,005,724 A | 2/1977 | Courtot |
| 4,005,726 A | 2/1977 | Fowler |
| D243,694 S | 3/1977 | Faulkner |
| 4,021,190 A | 5/1977 | Dickson |
| 4,067,354 A | 1/1978 | St. Clair |
| 4,067,358 A | 1/1978 | Streich |
| 4,081,235 A | 3/1978 | Van der Veer |
| 4,101,257 A | 7/1978 | Straitz, III |
| 4,146,056 A | 3/1979 | Buchanan |
| 4,157,238 A | 6/1979 | Van Berkum |
| 4,171,712 A | 10/1979 | DeForrest |
| 4,181,154 A | 1/1980 | Oley et al. |
| 4,251,025 A | 2/1981 | Bonne et al. |
| 4,253,493 A | 3/1981 | English |
| 4,290,450 A | 9/1981 | Swanson |
| 4,301,825 A | 11/1981 | Simko |
| 4,348,172 A | 9/1982 | Miller |
| 4,355,659 A | 10/1982 | Kelchner |
| 4,359,284 A | 11/1982 | Kude et al. |
| 4,386,625 A | 6/1983 | Perkins et al. |
| 4,453,568 A | 6/1984 | Canalizo |
| 4,454,892 A | 6/1984 | Chadshay |
| 4,465,456 A | 8/1984 | Hynek et al. |
| 4,474,166 A | 10/1984 | Shaftner et al. |
| 4,515,554 A | 5/1985 | Sirand |
| 4,538,644 A | 9/1985 | Knutson et al. |
| 4,566,488 A | 1/1986 | Chow et al. |
| 4,610,425 A | 9/1986 | Kelly |
| 4,625,762 A | 12/1986 | Hassanzadeh et al. |
| 4,653,530 A | 3/1987 | Kelly |
| 4,660,595 A | 4/1987 | Kuster et al. |
| 4,683,864 A | 8/1987 | Bucci |
| 4,705,330 A | 11/1987 | Tindall |
| 4,718,448 A | 1/1988 | Love et al. |
| 4,718,846 A | 1/1988 | Oguri et al. |
| 4,768,543 A | 9/1988 | Wienke et al. |
| 4,768,947 A | 9/1988 | Adachi |
| 4,782,814 A | 11/1988 | Cherryholmes |
| 4,787,414 A | 11/1988 | Kelly et al. |
| 4,796,652 A | 1/1989 | Hafla |
| 4,848,133 A | 7/1989 | Paulis et al. |
| 4,850,530 A | 7/1989 | Uecker |
| 4,874,006 A | 10/1989 | Iqbal |
| 4,895,184 A | 1/1990 | Abbey |
| 4,930,538 A | 6/1990 | Browne |
| 4,944,324 A | 7/1990 | Kajino et al. |
| 4,958,771 A | 9/1990 | Klomp |
| 4,965,707 A | 10/1990 | Butterfield |
| 5,025,990 A | 6/1991 | Ridenour |
| 5,027,854 A | 7/1991 | Genbauffe |
| 5,040,567 A | 8/1991 | Nestler et al. |
| 5,044,390 A | 9/1991 | Kelly et al. |
| 5,048,563 A | 9/1991 | Buchanan et al. |
| 5,063,956 A | 11/1991 | Borcuch et al. |
| 5,090,451 A | 2/1992 | Buchanan et al. |
| 5,090,899 A | 2/1992 | Kee |
| 5,097,818 A | 3/1992 | Kee et al. |
| 5,172,728 A | 12/1992 | Tsukazaki |
| 5,189,991 A | 3/1993 | Humburg |
| 5,239,979 A | 8/1993 | Maurice et al. |
| 5,245,997 A | 9/1993 | Bartos |
| 5,251,823 A | 10/1993 | Joshi et al. |
| 5,278,936 A | 1/1994 | Shao |
| 5,326,029 A | 7/1994 | Schultz |
| 5,353,766 A | 10/1994 | Peters et al. |
| 5,379,794 A | 1/1995 | Brown |
| 5,413,141 A | 5/1995 | Dietiker |
| 5,452,709 A | 9/1995 | Mealer |
| 5,458,294 A | 10/1995 | Zachary et al. |
| 5,470,018 A | 11/1995 | Smith |
| 5,494,072 A | 2/1996 | Schinowsky |
| 5,513,798 A | 5/1996 | Tavor |

(56) References Cited

U.S. PATENT DOCUMENTS

| | | |
|---|---|---|
| 5,520,206 A | 5/1996 | Deville |
| 5,542,609 A | 8/1996 | Myers et al. |
| 5,544,538 A | 8/1996 | Takagi et al. |
| 5,567,141 A | 10/1996 | Joshi et al. |
| 5,584,680 A | 12/1996 | Kim |
| 5,591,024 A | 1/1997 | Eavenson et al. |
| 5,603,211 A | 2/1997 | Graves |
| 5,630,408 A | 5/1997 | Versluis |
| 5,634,491 A | 6/1997 | Benedict |
| 5,642,580 A | 7/1997 | Hess et al. |
| 5,645,043 A | 7/1997 | Long et al. |
| 5,653,257 A | 8/1997 | Johnston |
| 5,674,065 A | 10/1997 | Grando et al. |
| 5,706,859 A | 1/1998 | Backlund |
| D391,345 S | 2/1998 | Mandir et al. |
| 5,782,626 A | 7/1998 | Joos et al. |
| 5,785,075 A | 7/1998 | Uchida et al. |
| 5,787,874 A | 8/1998 | Krohn et al. |
| 5,787,928 A | 8/1998 | Allen et al. |
| 5,795,145 A | 8/1998 | Manning et al. |
| 5,807,098 A | 9/1998 | Deng |
| 5,814,121 A | 9/1998 | Travis |
| 5,838,243 A | 11/1998 | Gallo |
| 5,865,618 A | 2/1999 | Hiebert |
| 5,906,197 A | 5/1999 | French et al. |
| 5,915,952 A | 6/1999 | Manning et al. |
| 5,931,661 A | 8/1999 | Kingery |
| 5,941,699 A | 8/1999 | Abele |
| 5,944,257 A | 8/1999 | Dietiker et al. |
| 5,966,937 A | 10/1999 | Graves |
| 5,971,746 A | 10/1999 | Givens et al. |
| 5,975,112 A | 11/1999 | Ohmi et al. |
| 5,987,889 A | 11/1999 | Graves et al. |
| 5,988,204 A | 11/1999 | Reinhardt et al. |
| 5,988,214 A | 11/1999 | Tajima et al. |
| 6,000,427 A | 12/1999 | Hutton |
| 6,026,849 A | 2/2000 | Thordarson |
| 6,035,893 A | 3/2000 | Ohmi et al. |
| 6,045,058 A | 4/2000 | Dobbeling et al. |
| 6,050,081 A | 4/2000 | Jansen et al. |
| 6,076,517 A | 6/2000 | Kahlke et al. |
| 6,135,063 A | 10/2000 | Welden |
| 6,162,048 A | 12/2000 | Griffioen et al. |
| 6,244,223 B1 | 6/2001 | Welk |
| 6,244,524 B1 | 6/2001 | Tackels et al. |
| 6,247,486 B1 | 6/2001 | Schwegler et al. |
| 6,257,270 B1 | 7/2001 | Ohmi et al. |
| 6,340,298 B1 | 1/2002 | Vandrak et al. |
| 6,347,644 B1 | 2/2002 | Channell |
| 6,354,072 B1 | 3/2002 | Hura |
| 6,354,078 B1 | 3/2002 | Karlsson et al. |
| 6,402,052 B1 | 6/2002 | Murawa |
| 6,431,957 B1 | 8/2002 | Lefky |
| 6,543,235 B1 | 4/2003 | Crocker et al. |
| 6,607,854 B1 | 8/2003 | Rehg et al. |
| 6,634,351 B2 | 10/2003 | Arabaolaza |
| 6,672,326 B2 | 1/2004 | Pappalardo et al. |
| 6,705,342 B2 | 3/2004 | Santinanavat et al. |
| 6,786,194 B2 | 9/2004 | Koegler et al. |
| 6,832,625 B2 | 12/2004 | Ford |
| 6,832,628 B2 | 12/2004 | Thordarson et al. |
| 6,845,966 B1 | 1/2005 | Albizuri |
| 6,884,065 B2 | 4/2005 | Vandrak et al. |
| 6,901,962 B2 | 6/2005 | Kroupa et al. |
| 6,904,873 B1 | 6/2005 | Ashton |
| 6,910,496 B2 | 6/2005 | Strom |
| 6,938,634 B2 | 9/2005 | Dewey, Jr. |
| 6,941,962 B2 | 9/2005 | Haddad |
| 7,013,886 B2 | 3/2006 | Deng |
| 7,044,729 B2 | 5/2006 | Ayastuy et al. |
| 7,048,538 B2 | 5/2006 | Albizuri |
| 7,143,783 B2 | 12/2006 | Emke et al. |
| 7,146,997 B2 | 12/2006 | Francis et al. |
| 7,156,370 B2 | 1/2007 | Albizuri |
| 7,174,913 B2 | 2/2007 | Albizuri |
| 7,201,186 B2 | 4/2007 | Ayastuy |
| 7,225,830 B1 | 6/2007 | Kershaw |
| 7,228,872 B2 | 6/2007 | Mills |
| 7,251,940 B2 | 8/2007 | Graves et al. |
| 7,299,799 B2 | 11/2007 | Albizuri |
| 7,334,772 B2 | 2/2008 | Carepa |
| 7,367,352 B2 | 5/2008 | Hagen et al. |
| 7,386,981 B2 | 6/2008 | Zielinski et al. |
| 7,434,447 B2 | 10/2008 | Deng |
| 7,458,386 B2 | 12/2008 | Zhang |
| 7,487,888 B1 | 2/2009 | Pierre, Jr. |
| 7,490,869 B2 | 2/2009 | Iturralde et al. |
| 7,528,608 B2 | 5/2009 | Elexpuru et al. |
| 7,533,656 B2 | 5/2009 | Dingle |
| 7,559,339 B2 | 7/2009 | Golan et al. |
| 7,591,257 B2 | 9/2009 | Bayer et al. |
| 7,600,529 B2 | 10/2009 | Querejeta |
| 7,607,325 B2 | 10/2009 | Elexpuru et al. |
| 7,607,426 B2 | 10/2009 | Deng |
| 7,617,841 B2 | 11/2009 | Zimpfer et al. |
| 7,634,993 B2 | 12/2009 | Bellomo |
| 7,637,476 B2 | 12/2009 | Mugica et al. |
| 7,641,470 B2 | 1/2010 | Albizuri |
| 7,651,330 B2 | 1/2010 | Albizuri |
| 7,654,820 B2 | 2/2010 | Deng |
| 7,677,236 B2 | 3/2010 | Deng |
| 7,730,765 B2 | 6/2010 | Deng |
| 7,758,323 B2 | 7/2010 | Orue |
| 7,766,006 B1 | 8/2010 | Manning |
| 7,861,706 B2 | 1/2011 | Bellomo |
| 7,942,164 B2 | 5/2011 | Hsiao |
| 7,967,006 B2 | 6/2011 | Deng |
| 7,967,007 B2 | 6/2011 | Deng |
| 8,011,920 B2 | 9/2011 | Deng |
| 8,057,219 B1 | 11/2011 | Manning et al. |
| 8,123,150 B2 | 2/2012 | Khan et al. |
| 8,152,515 B2 | 4/2012 | Deng |
| 8,464,754 B2 | 6/2013 | Stretch et al. |
| 8,622,069 B2 | 1/2014 | Ferreira |
| 9,170,016 B2 | 10/2015 | Deng |
| 2002/0058266 A1 | 5/2002 | Clough et al. |
| 2002/0155011 A1 | 10/2002 | Hartnagel et al. |
| 2002/0160325 A1 | 10/2002 | Deng |
| 2002/0160326 A1 | 10/2002 | Deng |
| 2003/0010952 A1 | 1/2003 | Morete |
| 2003/0150496 A1 | 8/2003 | Rousselin |
| 2003/0213523 A1 | 11/2003 | Neff |
| 2003/0217555 A1 | 11/2003 | Gerhold |
| 2004/0011411 A1 | 1/2004 | Thordarson et al. |
| 2004/0025949 A1 | 2/2004 | Wygnaski |
| 2004/0040315 A1 | 3/2004 | Koyama et al. |
| 2004/0226600 A1 | 11/2004 | Starer et al. |
| 2004/0238030 A1 | 12/2004 | Dewey, Jr. |
| 2004/0238047 A1 | 12/2004 | Kuraguchi et al. |
| 2005/0028781 A1 | 2/2005 | Yamada |
| 2005/0036770 A1 | 2/2005 | Ito et al. |
| 2005/0167530 A1 | 8/2005 | Ward et al. |
| 2005/0202361 A1 | 9/2005 | Albizuri |
| 2005/0208443 A1 | 9/2005 | Bachinski et al. |
| 2006/0065315 A1 | 3/2006 | Neff et al. |
| 2006/0096644 A1 | 5/2006 | Goldfarb et al. |
| 2006/0154194 A1 | 7/2006 | Panther et al. |
| 2006/0201496 A1 | 9/2006 | Shingler |
| 2006/0236986 A1 | 10/2006 | Fujisawa et al. |
| 2007/0044856 A1 | 3/2007 | Bonior |
| 2007/0154856 A1 | 7/2007 | Hallit et al. |
| 2007/0210069 A1 | 9/2007 | Albizuri |
| 2007/0215223 A1 | 9/2007 | Morris |
| 2007/0215225 A1 | 9/2007 | Koch et al. |
| 2007/0266765 A1 | 11/2007 | Deng |
| 2007/0277803 A1 | 12/2007 | Deng |
| 2008/0041470 A1 | 2/2008 | Golan et al. |
| 2008/0121116 A1 | 5/2008 | Albizuri |
| 2008/0149872 A1 | 6/2008 | Deng |
| 2008/0153045 A1 | 6/2008 | Deng |
| 2008/0168980 A1 | 7/2008 | Lyons et al. |
| 2008/0223465 A1 | 9/2008 | Deng |
| 2008/0227045 A1 | 9/2008 | Deng |
| 2008/0236688 A1 | 10/2008 | Albizuri |

(56) References Cited

U.S. PATENT DOCUMENTS

| | | |
|---|---|---|
| 2008/0236689 A1 | 10/2008 | Albizuri |
| 2008/0314090 A1 | 12/2008 | Orue Orue et al. |
| 2009/0039072 A1 | 2/2009 | Llona |
| 2009/0140193 A1 | 6/2009 | Albizuri Landa |
| 2009/0159068 A1 | 6/2009 | Querejeta et al. |
| 2009/0280448 A1 | 11/2009 | Antxia Uribetxbarria et al. |
| 2010/0035195 A1 | 2/2010 | Querejeta Andueza et al. |
| 2010/0035196 A1 | 2/2010 | Deng |
| 2010/0086884 A1 | 4/2010 | Querejeta Andueza et al. |
| 2010/0086885 A1 | 4/2010 | Querejeta Andueza et al. |
| 2010/0089385 A1 | 4/2010 | Albizuri |
| 2010/0089386 A1 | 4/2010 | Albizuri |
| 2010/0095945 A1 | 4/2010 | Manning |
| 2010/0102257 A1 | 4/2010 | Achor et al. |
| 2010/0132626 A1 | 6/2010 | Torgerson et al. |
| 2010/0154777 A1 | 6/2010 | Carvalho et al. |
| 2010/0163125 A1 | 7/2010 | Igarashi |
| 2010/0255433 A1 | 10/2010 | Querejeta Andueza et al. |
| 2010/0275953 A1 | 11/2010 | Orue Orue et al. |
| 2010/0310997 A1 | 12/2010 | Mugica Odriozola et al. |
| 2010/0319789 A1 | 12/2010 | Erdmann et al. |
| 2010/0326430 A1 | 12/2010 | Deng |
| 2010/0330513 A1 | 12/2010 | Deng |
| 2010/0330518 A1 | 12/2010 | Deng |
| 2010/0330519 A1 | 12/2010 | Deng |
| 2011/0081620 A1 | 4/2011 | Deng |
| 2011/0143294 A1 | 6/2011 | Deng |
| 2011/0168284 A1 | 7/2011 | Whitford et al. |
| 2011/0193000 A1 | 8/2011 | Miyazoe et al. |
| 2011/0198841 A1 | 8/2011 | Kitagawa |
| 2011/0226355 A1 | 9/2011 | Benvenuto et al. |
| 2011/0284791 A1 | 11/2011 | Vasquez et al. |
| 2012/0006091 A1 | 1/2012 | Deng |
| 2012/0006426 A1 | 1/2012 | Gorelic |
| 2012/0012097 A1 | 1/2012 | Deng |
| 2012/0012099 A1 | 1/2012 | Deng |
| 2012/0012103 A1 | 1/2012 | Deng |
| 2012/0067341 A1 | 3/2012 | Mateos |
| 2012/0080024 A1 | 4/2012 | Deng |
| 2012/0118238 A1 | 5/2012 | Togerson et al. |
| 2012/0132189 A1 | 5/2012 | Deng |
| 2012/0160186 A1 | 6/2012 | Turrin |
| 2012/0187318 A1 | 7/2012 | Chen |
| 2013/0098349 A1 | 4/2013 | Deng |
| 2014/0186783 A1 | 7/2014 | Deng |

FOREIGN PATENT DOCUMENTS

| | | |
|---|---|---|
| CN | 2430629 Y | 5/2001 |
| CN | 1873268 | 12/2006 |
| CN | 2844777 Y | 12/2006 |
| CN | 200979025 Y | 11/2007 |
| CN | 201013968 Y | 1/2008 |
| CN | 201028619 Y | 2/2008 |
| CN | 101140033 A | 3/2008 |
| CN | 201166154 Y | 12/2008 |
| CN | 101363549 A | 2/2009 |
| CN | 201212569 Y | 3/2009 |
| CN | 201228788 Y | 4/2009 |
| CN | 201241969 Y | 5/2009 |
| CN | 101699109 A | 4/2010 |
| CN | 101701635 B | 5/2010 |
| CN | 101865312 A | 10/2010 |
| CN | 201606540 U | 10/2010 |
| CN | 101881481 A | 11/2010 |
| CN | 201621334 U | 11/2010 |
| CN | 201651456 U | 11/2010 |
| CN | 101943476 A | 1/2011 |
| CN | 201739559 U | 2/2011 |
| CN | 201779762 U | 3/2011 |
| CN | 201982726 U | 9/2011 |
| CN | 102494164 A | 6/2012 |
| CN | 102506198 A | 6/2012 |
| CN | 202360799 U | 8/2012 |
| CN | 102661409 A | 9/2012 |
| CN | 202708189 U | 1/2013 |
| CN | 202708209 U | 1/2013 |
| CN | 202884149 U | 4/2013 |
| CN | 202884174 U | 4/2013 |
| CN | 202884327 U | 4/2013 |
| CN | 202955313 U | 5/2013 |
| CN | 202955780 U | 5/2013 |
| DE | 113 680 C | 11/1899 |
| DE | 720 854 C | 5/1942 |
| DE | 1650303 | 9/1970 |
| DE | 1959677 | 5/1971 |
| DE | 3345561 A1 | 7/1985 |
| DE | 3700233 A1 | 7/1988 |
| DE | 19543018 | 5/1997 |
| EP | 0509626 | 10/1992 |
| EP | 1326050 | 7/2003 |
| EP | 1939526 | 7/2008 |
| EP | 1970625 | 9/2008 |
| FR | 2151367 | 4/1973 |
| GB | 19845 | 2/1913 |
| GB | 1136468 | 12/1968 |
| GB | 1381887 | 1/1975 |
| GB | 1424711 | 2/1976 |
| GB | 2210155 | 6/1989 |
| GB | 2241180 | 8/1991 |
| GB | 2298039 | 8/1996 |
| JP | S5765469 A | 4/1982 |
| JP | 58 219320 A | 12/1983 |
| JP | 59009425 | 1/1984 |
| JP | 03 230015 A | 10/1991 |
| JP | H11311150 A | 11/1991 |
| JP | 05-256422 | 5/1993 |
| JP | H09329254 A | 12/1997 |
| JP | 10141656 | 5/1998 |
| JP | 11192166 | 7/1999 |
| JP | 11-344216 | 12/1999 |
| JP | 2000234738 | 8/2000 |
| JP | 2003 056845 A | 2/2003 |
| JP | 2003 074837 A | 3/2003 |
| JP | 2003 074838 A | 3/2003 |
| JP | 2003099131 A | 4/2003 |
| JP | 2004360713 A | 12/2004 |
| JP | 2010071477 | 4/2010 |
| WO | 02077545 A1 | 10/2002 |
| WO | 2007109664 A2 | 9/2007 |
| WO | 2008012849 A1 | 1/2008 |
| WO | WO 2008/071970 | 6/2008 |

OTHER PUBLICATIONS

Consumer Guide to Vent-Free Gas Supplemental Heating Products, est. 2007.
Heat and Glo, Escape Series Gas Fireplaces, Mar. 2005.
Heat and Glo, Escape-42DV Owner's Manual, Rev. i, Dec. 2006.
Napoleon, Park Avenue Installation and Operation Instructions, Jul. 20, 2006.
Napoleon, The Madison Installation and Operation Instructions, May 24, 2005.
International Search Report and Written Opinion for International Application No. PCT/US2011/039521, Notification dated Mar. 18, 2013.
International Search Report and Written Opinion for International Application No. PCT/US2011/039524, Notification dated Mar. 13, 2013.
International Search Report and Written Opinion for International Application No. PCT/US2011/039525, Notification dated Apr. 5, 2013.
International Search Report and Written Opinion for International Application No. PCT/US2011/039526, Notification dated Mar. 28, 2013.
Extended European Search Report in International Application No. PCT/US2013/048769, dated Apr. 22, 2016.
Gas Hearth Systems Reference Manual, Chapter 18: Millivolt Gas Control Valves, Jun. 2006.
International Search Report and Written Opinion for International Application No. PCT/US2013/056007, Notification dated Feb. 3, 2014.

(56) References Cited

OTHER PUBLICATIONS

International Search Report and Written Opinion for International Application No. PCT/US2012/021455, Notification dated Oct. 8, 2013.
International Search Report and Written Opinion for International Application No. PCT/US2012/034983, Notification dated Jul. 24, 2012.
International Search Report and Written Opinion for International Application No. PCT/US2013/040202, Notification dated Sep. 6, 2013.
International Search Report and Written Opinion for International Application No. PCT/US2013/056024, Notification dated Jan. 9, 2014.
International Search Report and Written Opinion dated Nov. 5, 2013 in the related PCT Application No. PCT/US13/48769.
Invitation to Pay Additional Fees and, Where Applicable, Protest Fee for PCT Application No. PCT/US2012/032176 filed Apr. 4, 2012.
Country Flame Technologies Inglenook Fireplace Gas Log Set Model INGLS 24-N or INGLS 24-P Natural Gas or Propane Conversion Kit, Installation, Operation, and Maintenance Manual, 2004.
Desa Heating Products, Technical Service Training Manual, 2004.
Flagro F-400T Dual Fuel Construction Heater, Operating Instructions Manual.
Heat Wagon S1505 Construction Heater, Installation and Maintenance Manual, Jul. 29, 2002.
Jotul GF 3 BVAllagash B-Vent Gas Heater, Installation and Operating Instructions, Dec. 2000.
Vanguard Unvented (Vent-Free) Propane/LP Gas Log Heater Manual, Feb. 2004.
White Mountain Hearth, The Vail Vent-Free Gas Fireplace, Installation Instructions and Owner's Manual, Mar. 2006.
Installation Instructions and Owner's Manuals for Empire Unvented Gas Fireplace Model VFHS-36, Mar. 2001.
Installation Instructions and Owner's Manuals for Empire Unvented Gas Fireplace Model VFHS-33, Apr. 2001.
Installation Instructions and Owner's Manuals for Empire Unvented Gas Fireplace Models VFHD-32 and VFHS-36, Apr. 2003.
Installation Instructions and Owner's Manuals for Empire Unvented Gas Fireplace Models VFHD-32 and VFHS-36, Sep. 2003.
Installation Instructions and Owner's Manuals for Empire Unvented Gas Fireplace Models VFHD-32 and VFHS-36, Feb. 2004.
Installation Instructions and Owner's Manuals for Empire Unvented Gas Fireplace Models VFHD-32 and VFHS-36, Sep. 2004.
Installation Instructions and Owner's Manuals for Empire Unvented Gas Fireplace Models VFHD-32 and VFHS-36, Jun. 2005.
Installation Instructions and Owner's Manuals for Empire Unvented Gas Fireplace Models VFP32FP and VFP36FP, Mar. 2006.
Installation Instructions and Owner's Manuals for Empire Unvented Gas Fireplace Models VFP32FP and VFP36FP, May 2006.
Installation Instructions and Owner's Manuals for Empire Unvented Gas Fireplace Model VFHS-20, Jun. 2002.
Installation Instructions and Owner's Manuals for Empire Unvented Gas Fireplace Model VFHS-20, Sep. 2003.
Installation Instructions and Owner's Manuals for Empire Unvented Gas Fireplace Model VFHS-20, Nov. 2003.
Installation Instructions and Owner's Manuals for Empire Unvented Gas Fireplace Model VFHS-20, Sep. 2004.
Installation Instructions and Owner's Manuals for Empire Unvented Gas Fireplace Model VFHS-20, Jun. 2005.
Installation Instructions and Owner's Manuals for Empire Unvented Gas Fireplace Model VFHS-32, Aug. 2002.
*Procom Heating, Inc.* v. *GHP Group, Inc.*: GHP's Answer to the First Amended Complaint, Aug. 27, 2014.
*Procom Heating, Inc.* v. *GHP Group, Inc.*: Procom Heating's First Amended Complaint, Aug. 13, 2014.
*Procom Heating, Inc.* v. *GHP Group, Inc.*: Claims Construction Memorandum Opinion and Order, Jul. 8, 2015.
*Procom Heating, Inc.* v. *GHP Group, Inc.*: GHP's Initial Invalidity Contentions, Mar. 31, 2014.
*Procom Heating, Inc.* v. *GHP Group, Inc.*: GHP's 2nd Amended Initial Invalidity Contentions, Sep. 4, 2015.
*Procom Heating, Inc.* v. *GHP Group, Inc.*: GHP's 2nd Amended Initial Invalidity Contentions, Claims Chart—Exhibit A, Sep. 4, 2015.
*Procom Heating, Inc.* v. *GHP Group, Inc.*: GHP's 2nd Amended Initial Invalidity Contentions, Claims Chart—Exhibit B, Sep. 4, 2015.
*Procom Heating, Inc.* v. *GHP Group, Inc.*: GHP's 2nd Amended Initial Invalidity Contentions, Claims Chart—Exhibit C, Sep. 4, 2015.
*Procom Heating, Inc.* v. *GHP Group, Inc.*: GHP's 2nd Amended Initial Invalidity Contentions, Claims Chart—Exhibit D, Sep. 4, 2015.
*Procom Heating, Inc.* v. *GHP Group, Inc.*: GHP's 2nd Amended Initial Invalidity Contentions, Claims Chart—Exhibit E, Sep. 4, 2015.
*Procom Heating, Inc.* v. *GHP Group, Inc.*: GHP's 2nd Amended Initial Invalidity Contentions, Claims Chart—Exhibit F, Sep. 4, 2015.
*Procom Heating, Inc.* v. *GHP Group, Inc.*: GHP's 2nd Amended Initial Invalidity Contentions, Claims Chart—Exhibit G, Sep. 4, 2015.

* cited by examiner

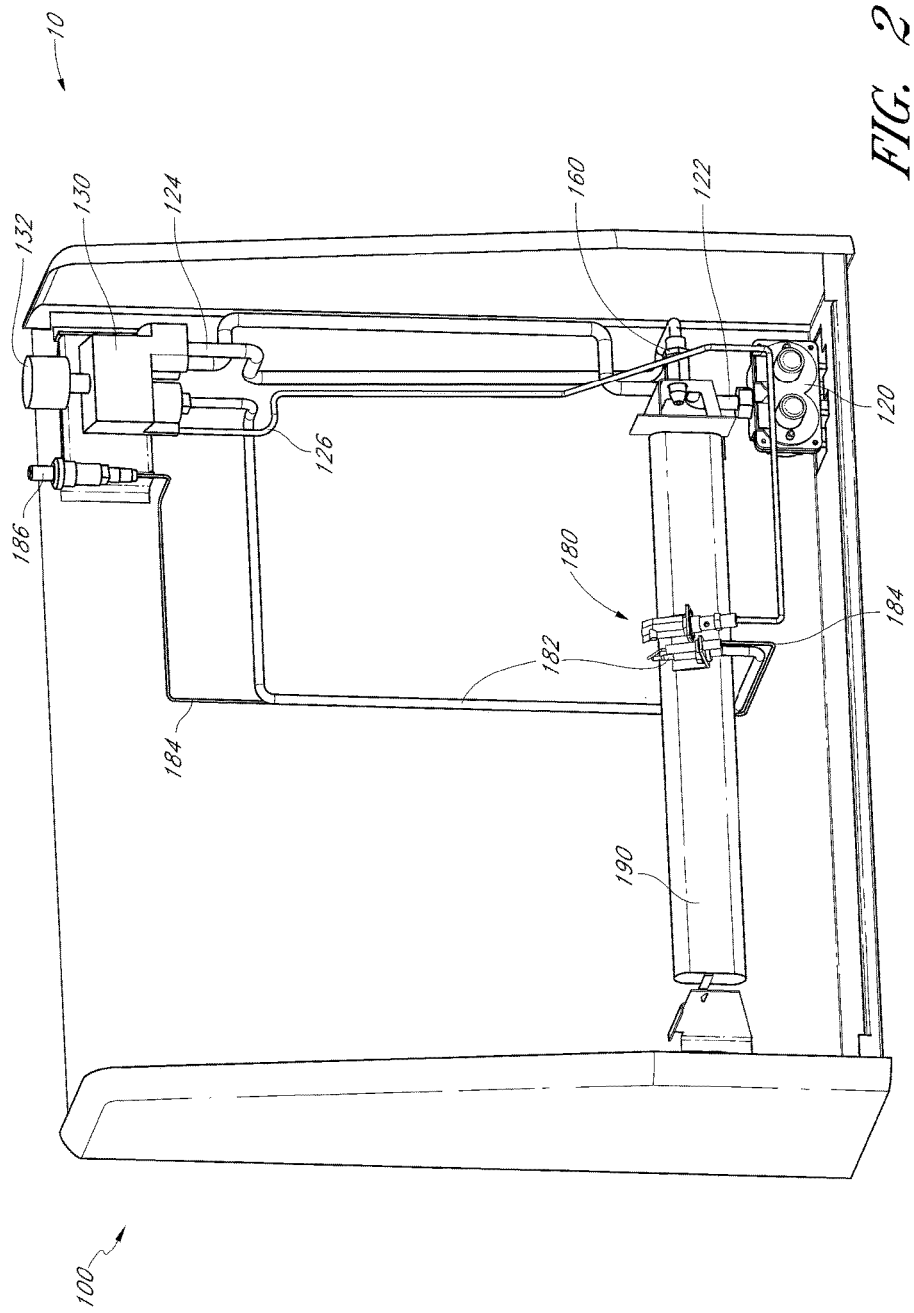

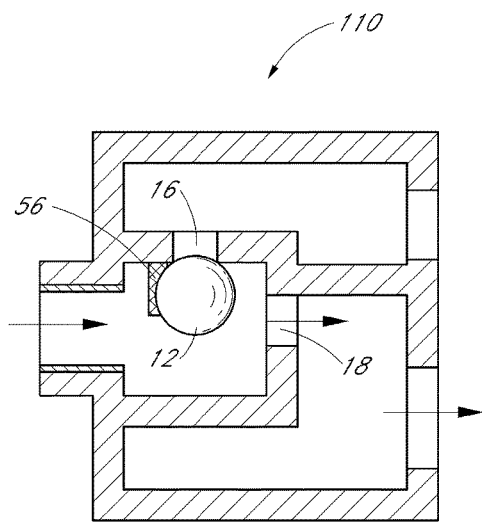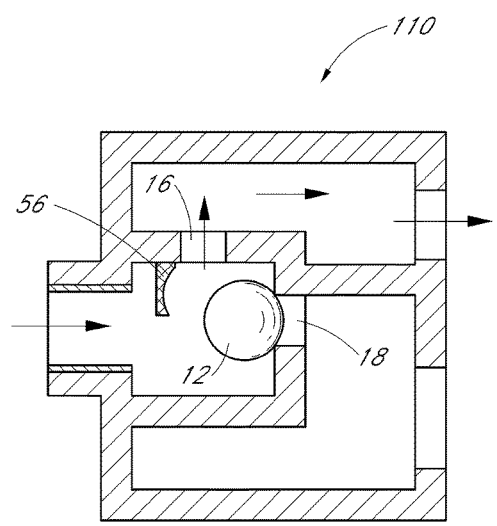
FIG. 13A    FIG. 13B
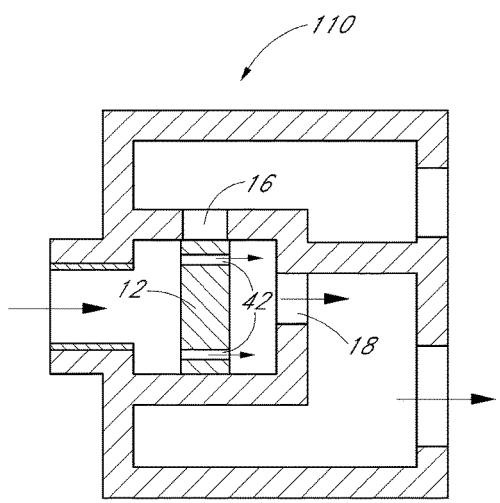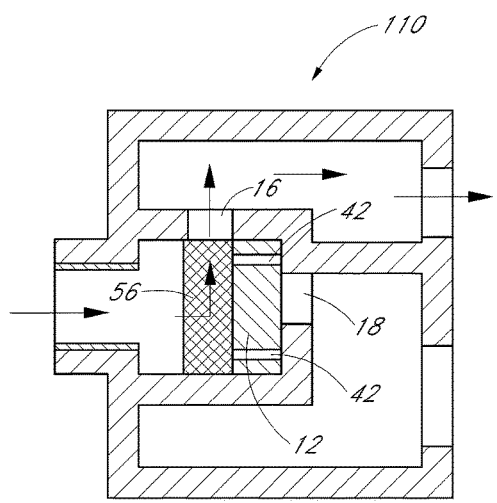
FIG. 14A    FIG. 14B

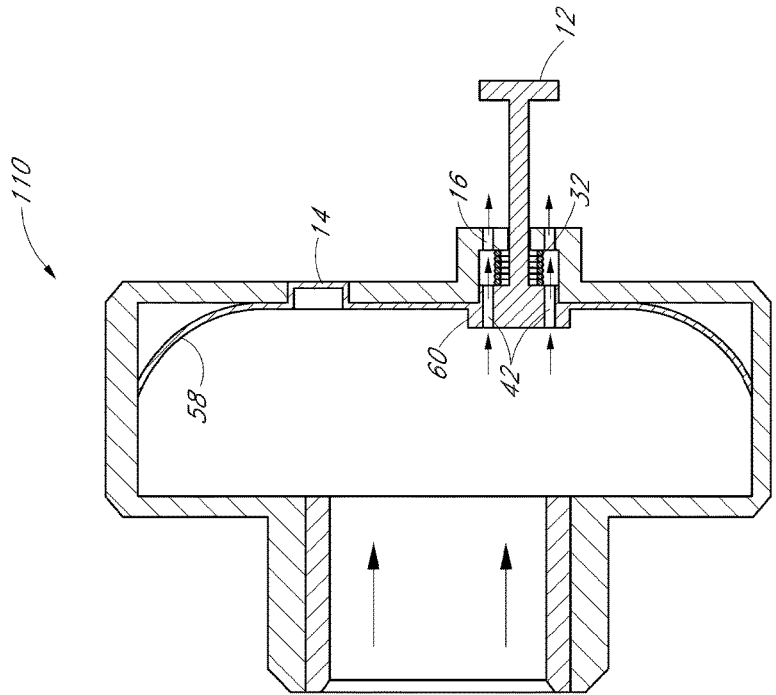
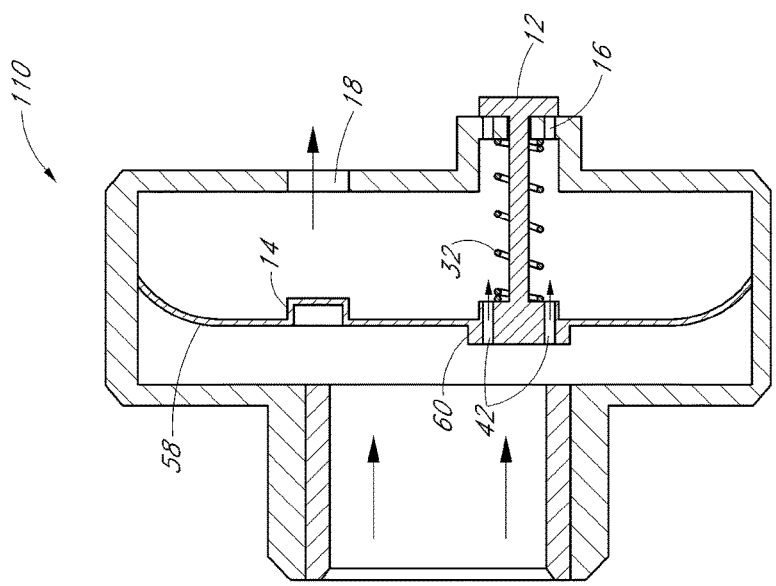

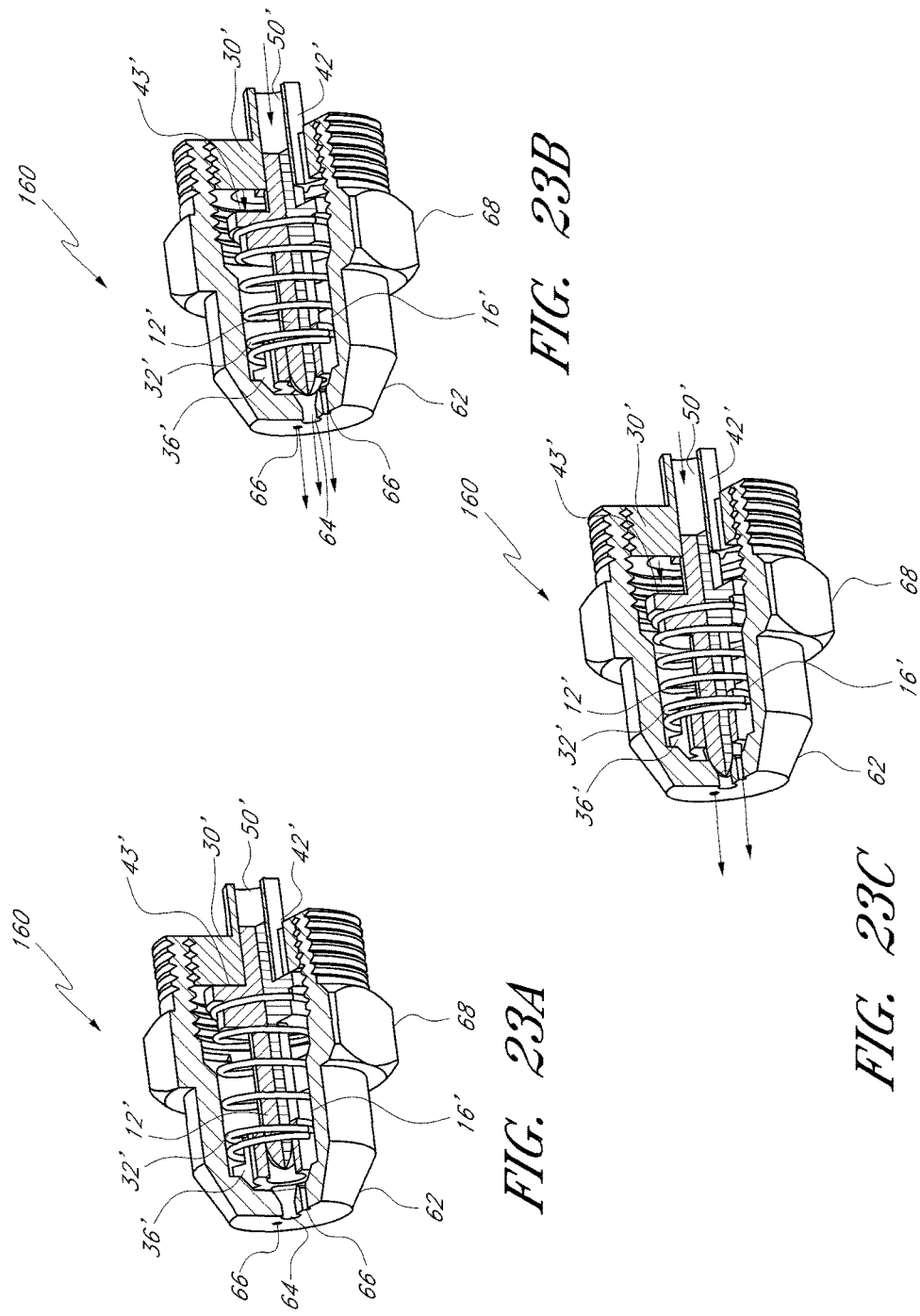

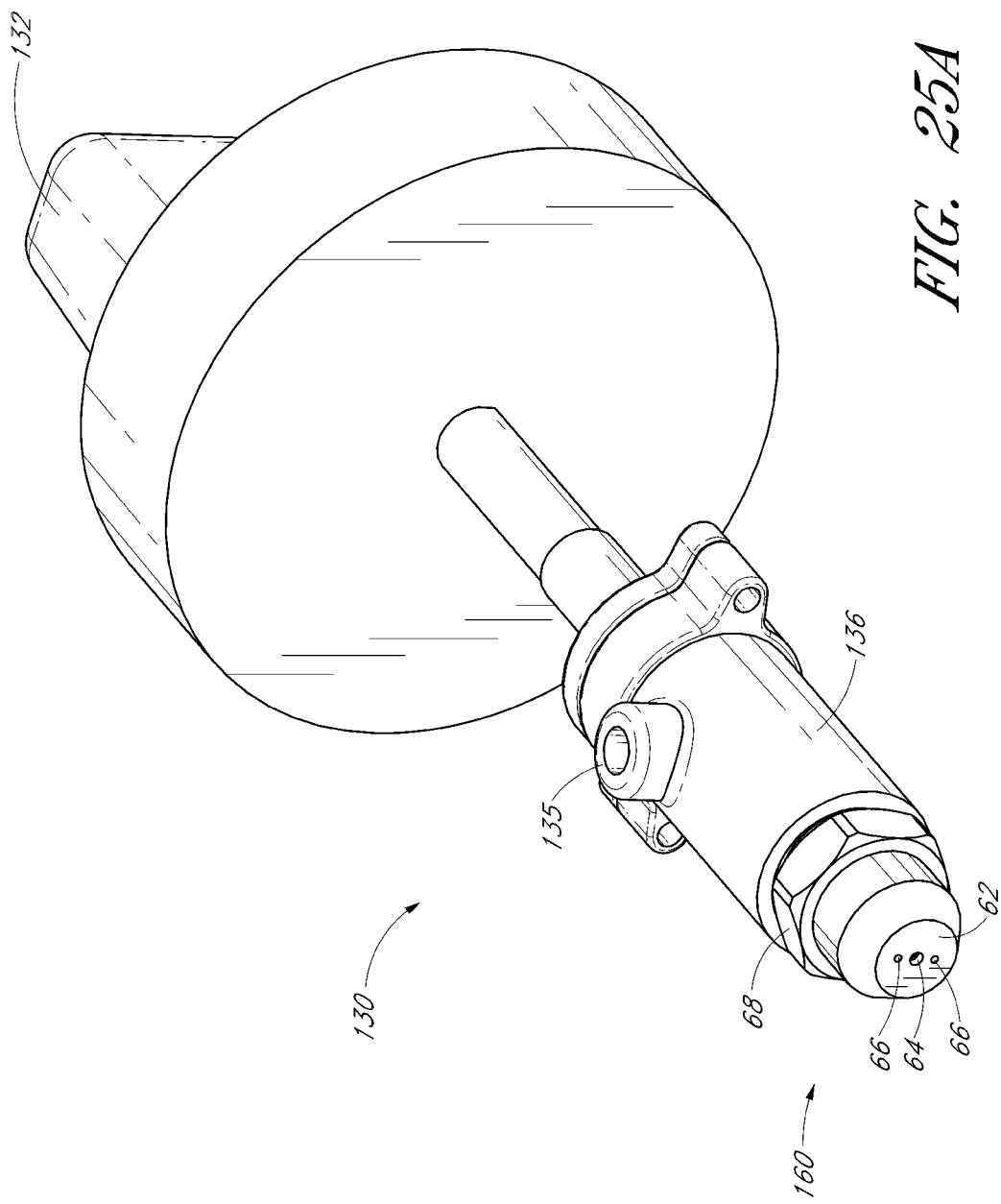

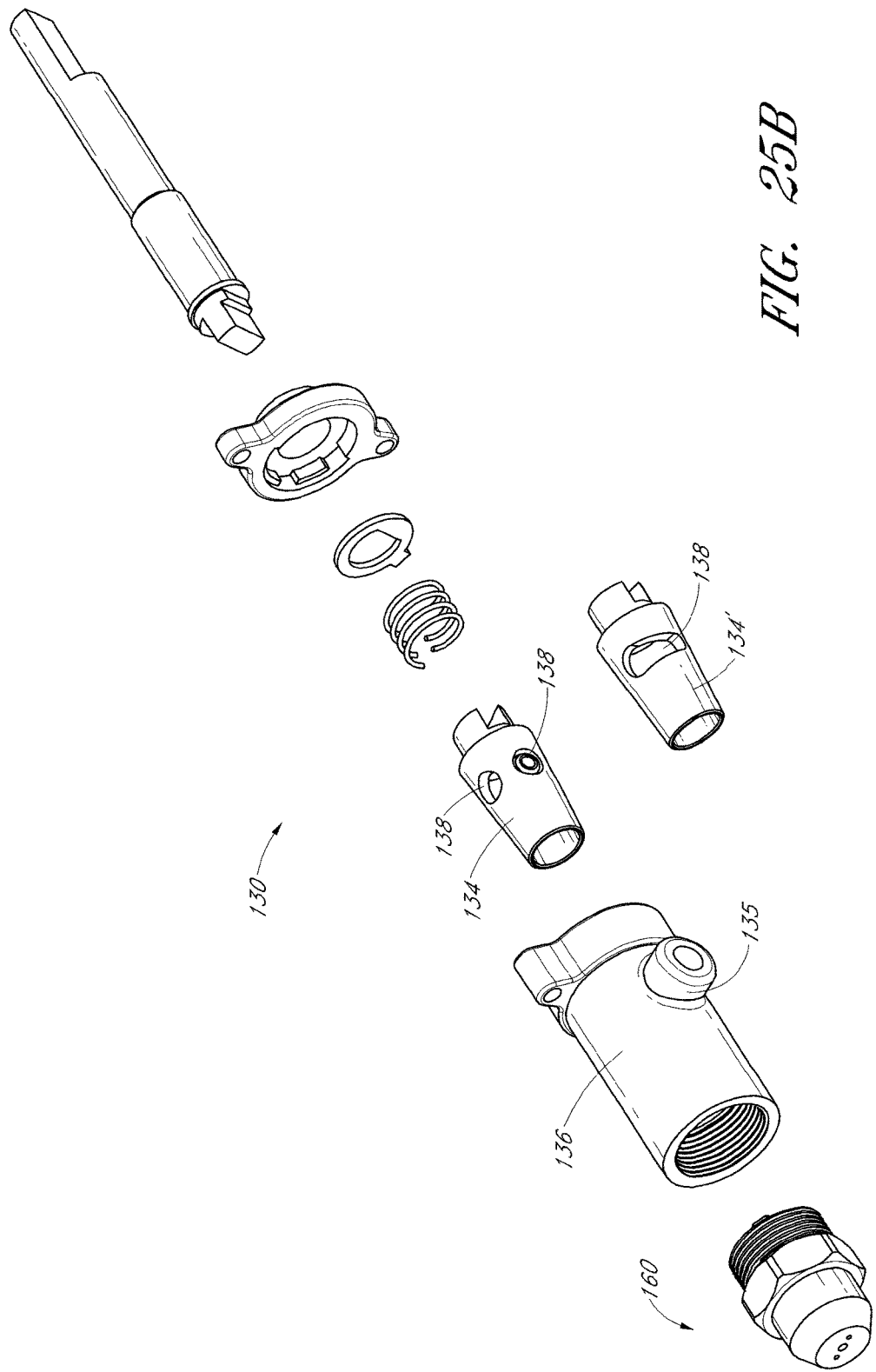

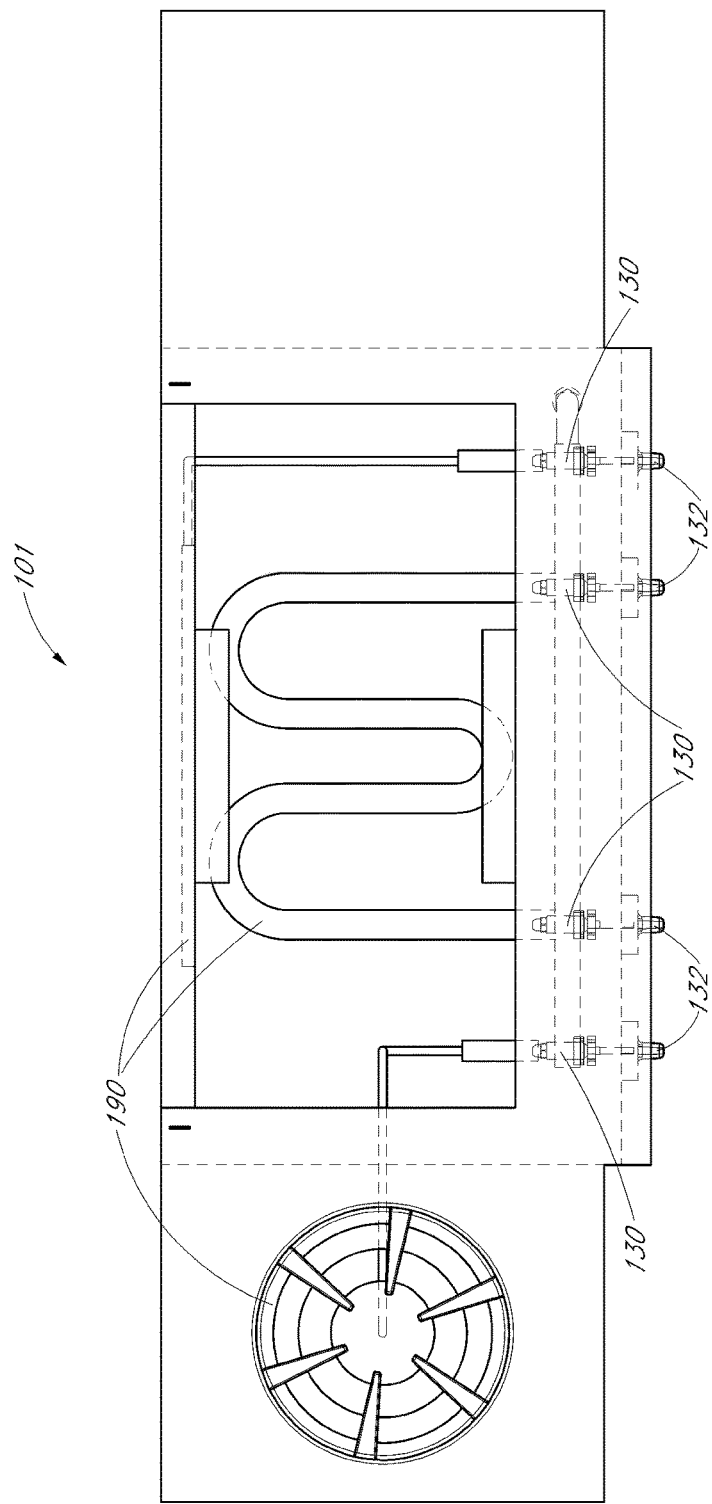

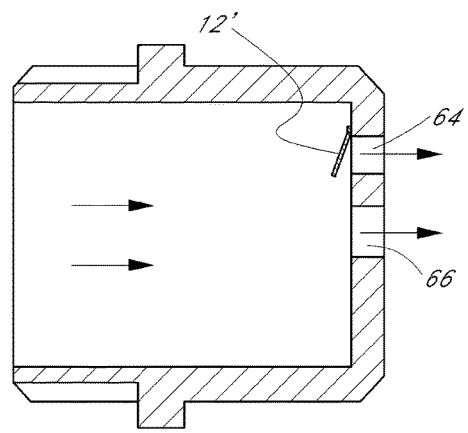
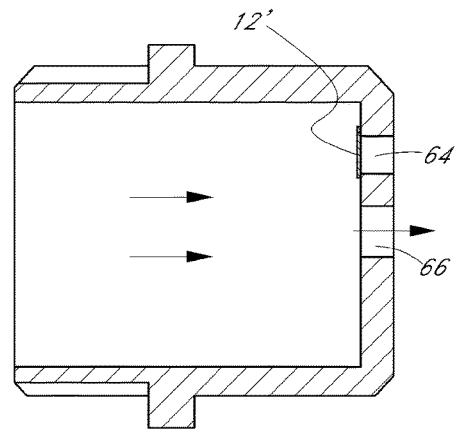
FIG. 31A        FIG. 31B
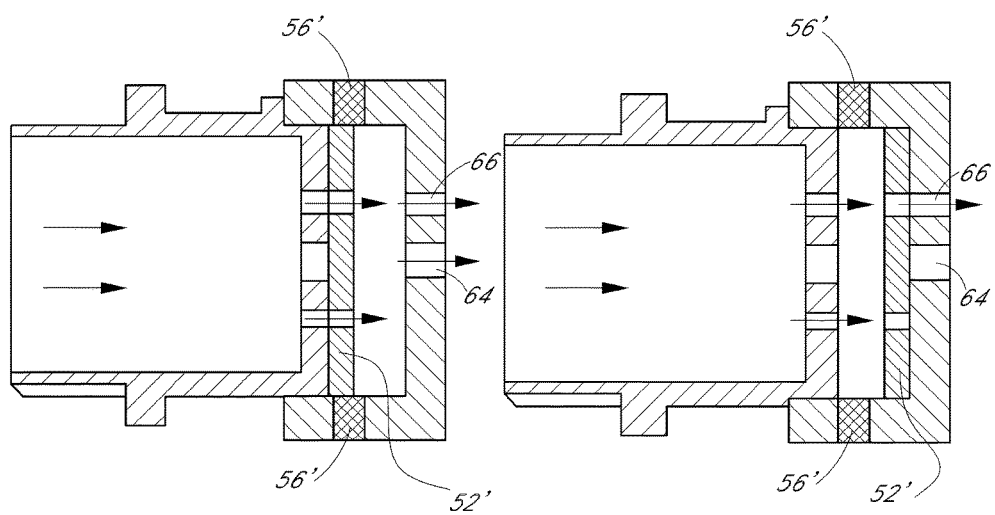
FIG. 32A        FIG. 32B

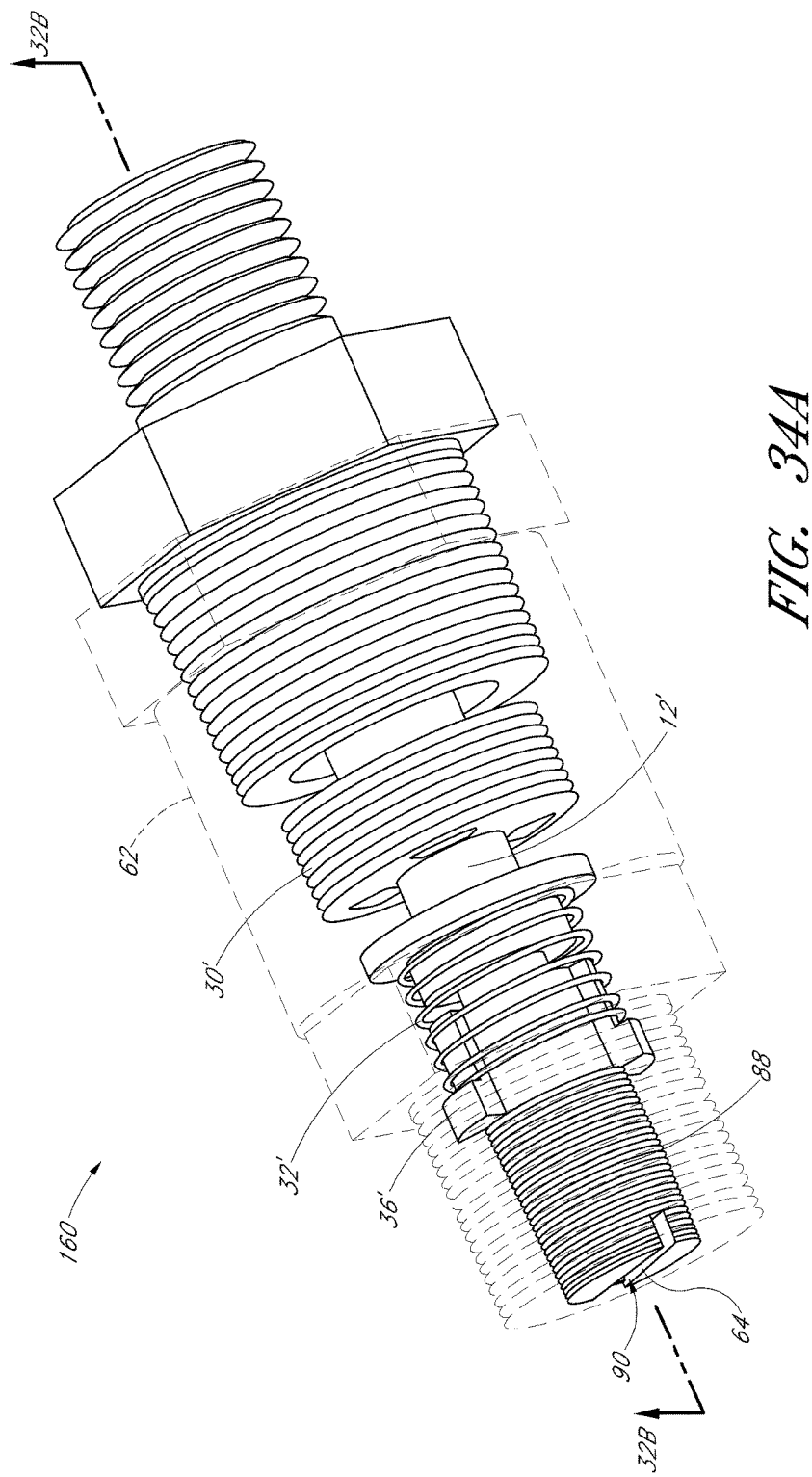

HEATING SYSTEM

CROSS-REFERENCE TO RELATED APPLICATIONS

This application is a divisional of U.S. patent application Ser. No. 13/155,348, filed Jun. 7, 2011, now U.S. Pat. No. 9,021,859, which claims priority to U.S. Provisional Application Nos. (1) 61/352,327, filed Jun. 7, 2010; (2) 61/352,329, filed Jun. 7, 2010; (3) 61/421,541, filed Dec. 9, 2010; and (4) 61/473,714, filed Apr. 8, 2011; the entire contents of all of which are hereby incorporated by reference herein and made a part of this specification.

BACKGROUND OF THE INVENTION

Field of the Invention

Certain embodiments disclosed herein relate generally to a heating source for use in a gas appliance. Aspects of certain embodiments may be particularly adapted for single fuel, dual fuel or multi-fuel use. The gas appliance can include, but is not limited to: heaters, boilers, dryers, washing machines, ovens, fireplaces, stoves, etc.

Description of the Related Art

Many varieties of heating sources, such as heaters, boilers, dryers, washing machines, ovens, fireplaces, stoves, and other heat-producing devices utilize pressurized, combustible fuels. However, such devices and certain components thereof have various limitations and disadvantages.

SUMMARY OF THE INVENTION

According to some embodiments a heating system can include any number of different components such as a fuel selector valve, a pressure regulator, a control valve, a burner nozzle, a burner, and/or an oxygen depletion sensor. In addition, a heating system can be a single fuel, dual fuel or multi-fuel heating system. For example, the heating system can be configured to be used with one or more of natural gas, liquid propane, well gas, city gas, and methane.

In some embodiments a heating system can comprise a fuel selector valve. The fuel selector valve can comprise an input, a first output, a second output, a first valve in-between the input and the first output and a second valve in-between the input and the second output. The first valve can include a first valve body and a first valve seat. The first valve can have a closed position wherein the first valve body is engaged with the first valve seat and an open position wherein the first valve body is disengaged from the first valve seat. The second valve can have a second valve body, a second valve seat and a third valve seat. The second valve can have two closed positions, a first closed position wherein the second valve body is engaged with the second valve seat and a second closed position wherein the second valve body is engaged with the third valve seat, and an open position wherein the first valve body is disengaged from both the second and third valve seats. Further, the fuel selector valve can be configured such that a pressure of a fluid entering the input determines whether either the first valve or the second valve is open.

In some embodiments, the heating system can further include a first fuel pressure regulator in communication with the first output, the first fuel pressure regulator configured to control the flow of fluid within a first predetermined pressure range and a second fuel pressure regulator in communication with the second output, the second fuel pressure regulator configured to control the flow of fluid within a second predetermined pressure range, different from the first. The fuel selector valve may further comprise first and second biasing members, the first biasing member configured to at least partially control the opening and closing of the first valve and the second biasing member configured to at least partially control the opening and closing of the second valve. In some embodiments, the first and second valve seats can be adjustable and configured to be able to calibrate the first and second valves to open and/or close at particular pressures.

In some embodiments, a fuel selector valve can comprise a housing having an input, a first output, and a second output; a first valve in-between the input and the first output, the first valve comprising a first valve body and a first valve seat, the first valve configured to have a closed position wherein the first valve body is engaged with the first valve seat and an open position wherein the first valve body is disengaged from the first valve seat; a second valve in-between the input and the second output, the second valve comprising a second valve body, and a second valve seat, the second valve configured to have a first closed position wherein the second valve body is engaged with the second valve seat and an open position wherein the first valve body is disengaged from the second valve seat; wherein the fuel selector valve is configured such that the first valve and the second valve are configured to move between their respective open and closed position based on a predetermined fluid pressure acting on the valve and the pressure of the fluid entering the input of the fuel selector valve determines whether either the first valve or the second valve is open.

In some embodiments, a fuel selector valve can comprise a housing having an inlet, an outlet, a first flow path therethrough and a second flow path therethrough different from the first flow path; at least one pressure sensitive gate within the housing, wherein the at least one pressure sensitive gate is configured to be open when a fluid within a first pressure range is flowing through the fuel selector valve and closed when a fluid within a second pressure range, different from the first, is flowing through the fuel selector valve, wherein the flow of fluid acts on the gate to either open or close the gate; wherein the fuel selector valve is configured such that when the gate is open, fluid flows through the first flow path and when the gate is closed, fluid flows through the second flow path.

A heating system of certain embodiments can comprise a fuel selector valve, a burner nozzle and a burner. A fuel selector valve can comprise a housing having an inlet, an outlet, a first flow path and a second flow path and at least one pressure sensitive gate within the housing. The at least one pressure sensitive gate can be configured to be open when a fluid within a first pressure range is flowing through the fuel selector valve and closed when a fluid within a second pressure range, different from the first, is flowing through the fuel selector valve, wherein the flow of fluid acts on the gate to either open or close the gate. Further the fuel selector valve can be configured such that when the gate is open, fluid flows through the first flow path and when the gate is closed, fluid flows through the second flow path.

According to some embodiments, the heating system further comprises a first fuel pressure regulator in communication with the output, the first fuel pressure regulator configured to control the flow of fluid within a first predetermined pressure range; and a second fuel pressure regulator in communication with second output, the second fuel pressure regulator configured to control the flow of fluid within a second predetermined pressure range, different from the first.

The at least one pressure sensitive gate of some embodiments can comprise a first and a second pressure sensitive gate. The fuel selector valve can be configured such that when the first pressure sensitive gate is open, the second pressure sensitive gate is closed and when the second pressure sensitive gate is open, the first pressure sensitive gate is closed. The fuel selector valve can be further configured such that when no fluid is flowing through the fuel selector valve both the first and the second pressure sensitive gates are closed.

According to some embodiments, the at least one pressure sensitive gate can comprise a spring-loaded valve, or a magnet and a metal ball. In some embodiments, the fuel selector valve can further comprise first and second biasing members, the first biasing member configured to at least partially control the opening and closing of the first pressure sensitive gate and the second biasing member configured to at least partially control the opening and closing of the second pressure sensitive gate.

In some embodiments a heating system can comprise a burner nozzle and a burner. The burner nozzle can include a housing defining an inlet, an outlet and an inner chamber between the inlet and the outlet. The housing can be a single or multi-piece housing. The burner nozzle may also include a movable body within the inner chamber and a biasing member. The biasing member can be configured to regulate a positional relationship between the body and a wall of the inner chamber in response to a pressure of a fluid flow, flowing through the burner nozzle.

In some embodiments, the positional relationship between the body and the wall of the inner chamber can be configured to determine the amount of fluid flow through the burner nozzle, such that a predetermined increase in pressure of the fluid flow from an at rest position results in the movable body moving closer to the wall of the inner chamber to reduce the cross-sectional area of the flow passage between the body and the wall and correspondingly, a decrease in pressure of the fluid flow results in the movable body moving farther away from the wall of the inner chamber to increase the cross-sectional area of the flow passage between the body and the wall until the rest position is achieved.

In some embodiments of heating system, the positional relationship at a constant temperature of the fluid can provide for a constant BTU value as the pressure of the fuel fluctuates.

Further, in some embodiments, an increase in pressure of the fluid flow from the at rest position can result in the movable body moving closer to the wall of the inner chamber to reduce the cross-sectional area of the flow passage between the body and the wall until the fluid flow causes the movable body to contact the inner wall and stop the flow of fluid through the burner nozzle outlet.

According to certain embodiments, the burner nozzle can further comprise a second outlet, wherein the second outlet is configured to remain open and unobstructed, independent of the position of the movable body. The movable body may further comprise a channel passing therethrough, the channel configured to sealingly connect to the second outlet when the movable body is in contact with the wall of the inner chamber.

According to certain embodiments, a burner nozzle can comprise a housing defining an inlet, a first outlet, a second outlet, and an inner chamber between the inlet and the first and second outlets; a movable body within the inner chamber; and a biasing member configured to regulate the position of the movable body within the inner chamber in response to a pressure of a fluid flow, flowing through the burner nozzle; wherein in a second position of the movable body within the inner chamber, the second outlet being closed by the movable body and the amount of flow allowed through the burner nozzle is less than in a first position and wherein the movable body is configured such that movement between the first and second positions is controlled by the pressure of the fluid flow acting on the biasing member.

In some embodiments, a nozzle can comprise a nozzle housing; an inlet; at least two outlets; a valve comprising a valve body within the nozzle housing and between the inlet and the at least two outlets; and a biasing member wherein the valve and biasing member are configured such that fluid flow of a predetermined pressure acts on the valve body to at least one of 1) open, and 2) close the valve body within the nozzle housing to control fluid flow through the nozzle, wherein independent of the position of the valve body, the nozzle being configured such that at least one of the at least two outlets remains open.

In some embodiments, the burner nozzle can comprise a housing defining an inlet, an outlet and an inner chamber between the inlet and the outlet; a movable body within the inner chamber; and a biasing member configured to regulate a positional relationship between the body and a wall of the inner chamber in response to a pressure of a fluid flow, flowing through the burner nozzle; wherein the positional relationship between the body and the wall of the inner chamber is configured to determine the amount of fluid flow through the burner nozzle, such that a predetermined increase in pressure of the fluid flow from an at rest position results in the movable body moving closer to the wall of the inner chamber to reduce the cross-sectional area of the flow passage between the body and the wall and correspondingly, a decrease in pressure of the fluid flow results in the movable body moving farther away from the wall of the inner chamber to increase the cross-sectional area of the flow passage between the body and the wall until the rest position is achieved.

In some embodiments, a burner nozzle can comprise a housing defining an inlet, an outlet and an inner chamber between the inlet and the outlet; a movable body within the inner chamber; and a biasing member configured to regulate a positional relationship between the body and a wall of the inner chamber in response to a pressure of a fluid flow, flowing through the burner nozzle; wherein in a first position of the movable body within the inner chamber, the amount of flow allowed through the burner nozzle is more than in a second position and wherein the movable body is configured such that movement between the first and second positions is controlled by the pressure of the fluid flow acting on the biasing member.

Certain embodiments of a heating system can comprise a burner and a burner nozzle. The burner nozzle can include a housing defining an inlet, an outlet and an inner chamber between the inlet and the outlet; a movable body within the inner chamber; and a biasing member. The biasing member can be configured to regulate a positional relationship between the body and a wall of the inner chamber in response to a pressure of a fluid flow, flowing through the burner nozzle. According to some embodiments, in a first position of the movable body within the inner chamber, the amount of flow allowed through the burner nozzle is more than in a second position and the movable body can be configured such that movement between the first and second positions is controlled by the pressure of the fluid flow acting on the biasing member.

According to certain embodiments, the pressure of the flow can act on the biasing member through contact with the movable body. In the second position of some embodiments, the movable body can be configured to sealingly connect to the outlet. The movable body may further comprise a channel passing therethrough. In addition, the burner nozzle may further comprise a second outlet, and when the movable body is in the second position fluid flow can be prevented through the second outlet. In some embodiments, the burner nozzle can further include a second outlet, and when the movable body is in the second position flow of fluid is prevented through either of the outlet or the second outlet.

In some embodiments, a heating system can include a burner, a nozzle and a biasing member. The nozzle can have a nozzle housing, an inlet, an outlet and a valve body within the nozzle housing and between the inlet and the outlet. The valve body and biasing member can be configured such that fluid flow of a predetermined pressure acts on the valve body to at least one of 1) move, 2) open, and 3) close the valve body within the nozzle housing to control fluid flow through the nozzle.

In some embodiments, the heating system can also include an end cap within the outlet of the nozzle housing. The end cap can have a first end configured to be manipulated so as to adjust the position of the end cap within the outlet and at least one orifice passing through the end cap. The nozzle housing can be configured such that when the valve body is in an open position, fluid flows through the nozzle entering at the inlet and exiting at the outlet through the at least one orifice. The nozzle can be configured such that adjusting the position of the end cap adjusts at least one of the predetermined pressure required to 1) move, 2) open, and 3) close the valve body within the nozzle housing.

Many different types of end caps can be used. For example, the biasing member can be between the end cap and the valve body, the end cap configured to calibrate the nozzle to adjust the pressure required to move the valve body to an open position. In some examples, the end cap is a set screw. Also, the end of the end cap can cooperate with a tool to adjust the position of the end cap relative to the valve body. This end of the end cap can include a detent. The end cap can be adjusted from outside of the nozzle. The end cap can also include an orifice and/or the at least one orifice.

In some embodiments a heating system can comprise an oxygen depletion sensor (ODS). An ODS can include an igniter, an inlet, an outlet, a first injector, a second injector, a first valve body and a first biasing member to control flow of fuel from the inlet to the first injector and a second valve body and a second biasing member to control flow of fuel from the inlet to the second injector. There maybe one or two, or more inlets and outlets. At a first predetermined fluid pressure the first valve can be open and the second valve can be closed and at a second predetermined fluid pressure, greater than the first, the first valve can be closed by the second predetermined fluid pressure acting on the first valve and the second valve can be opened by the second predetermined fluid pressure acting on the second valve.

The valves can be set such that the first biasing member is configured to open the first valve by the first predetermined fluid pressure acting on the first valve, the first predetermined fluid pressure being insufficient to open the second valve.

In some embodiments, an ODS can comprise a housing having a single inlet and a single outlet, and having a first fluid flow path and a second fluid flow path through the housing between the inlet and the outlet; a first air intake; a second air intake; a first injector within the housing and defining part of the first fluid flow path, the first injector comprising a first orifice, the first orifice configured to direct a first fuel from the inlet and towards the outlet while drawing air into the housing through the first air intake; a second injector within the housing and defining part of the second fluid flow path, the second injector comprising a second orifice, second first orifice configured to direct a second fuel from the inlet and towards the outlet while drawing air into the housing through the second air intake, wherein the first fuel is at a pressure different from the second fuel; a first valve within the housing and defining part of the first fluid flow path, the first valve configured to control the flow of fuel to the first injector; and a second valve within the housing and defining part of the second fluid flow path, the second valve configured to control the flow of fuel to the second injector.

According to some embodiments, a heating system can have a burner, a control valve, and a nozzle. The control valve can include a control valve housing, an input, an output and a first valve body within the control valve housing configured such that the position of the first valve body within the control valve housing determines whether the input is in fluid communication with the output and how much fluid can flow therebetween.

A nozzle in some embodiments can include a nozzle housing, a second valve within the nozzle housing, an inlet, at least two outlets, and a biasing member configured such that the second valve is open during fluid flow of a first predetermined pressure, and fluid flow of a second predetermined pressure causes the second valve to close one of the at least two outlets while one of the at least two outlets remains open.

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

FIG. 2 is a perspective cutaway view of the heater of FIG. 1.

FIG. 3A illustrates a dual fuel heating assembly. FIG. 3B shows another dual fuel heating assembly. FIG. 3C illustrates an unregulated heating assembly.

FIGS. 13A-B are schematic cross-sectional views of a fuel selector valve in a first position and a second position.

FIGS. 14A-B are schematic cross-sectional views of a fuel selector valve in a first position and a second position.

FIGS. 15A-B are schematic cross-sectional views of a fuel selector valve in a first position and a second position.

FIGS. 23A-C are sectional views of the nozzle of FIG. 23 in first, second and third positions, respectively.

FIG. 25A shows the nozzle of FIG. 23 and a control valve.

FIG. 25B illustrates the nozzle separated from the control valve of FIG. 25A, where control valve is shown in an exploded view including two possible internal valve bodies.

FIGS. 26A-B show perspective and top views respectively of a barbeque grill.

FIGS. 31A-B are schematic cross-sectional views of a nozzle in a first position and a second position.

FIGS. 32A-B are schematic cross-sectional views of a nozzle in a first position and a second position.

FIGS. 34A-B show perspective and cross sectional views of a nozzle.

DETAILED DESCRIPTION OF THE PREFERRED EMBODIMENT

Many varieties of space heaters, wall heaters, stoves, fireplaces, fireplace inserts, gas logs, and other heat-producing devices employ combustible fluid fuels, such as liquid propane and natural gas. The term "fluid," as used herein, is a broad term used in its ordinary sense, and includes materials or substances capable of fluid flow, such as, for example, one or more gases, one or more liquids, or any combination thereof. Fluid-fueled units, such as those listed above, generally are designed to operate with a single fluid fuel type at a specific pressure or within a range of pressures. For example, some fluid-fueled heaters that are configured to be installed on a wall or a floor operate with natural gas at a pressure in a range from about 3 inches of water column to about 6 inches of water column, while others are configured to operate with liquid propane at a pressure in a range from about 8 inches of water column to about 12 inches of water column. Similarly, some gas fireplaces and gas logs are configured to operate with natural gas at a first pressure, while others are configured to operate with liquid propane at a second pressure that is different from the first pressure. As used herein, the terms "first" and "second" are used for convenience, and do not connote a hierarchical relationship among the items so identified, unless otherwise indicated.

Certain advantageous embodiments disclosed herein reduce or eliminate various problems associated with devices having heating sources that operate with only a single type of fuel source. Furthermore, although certain of the embodiments described hereafter are presented in a particular context, the apparatus and devices disclosed and enabled herein can benefit a wide variety of other applications and appliances.

Figure 1:
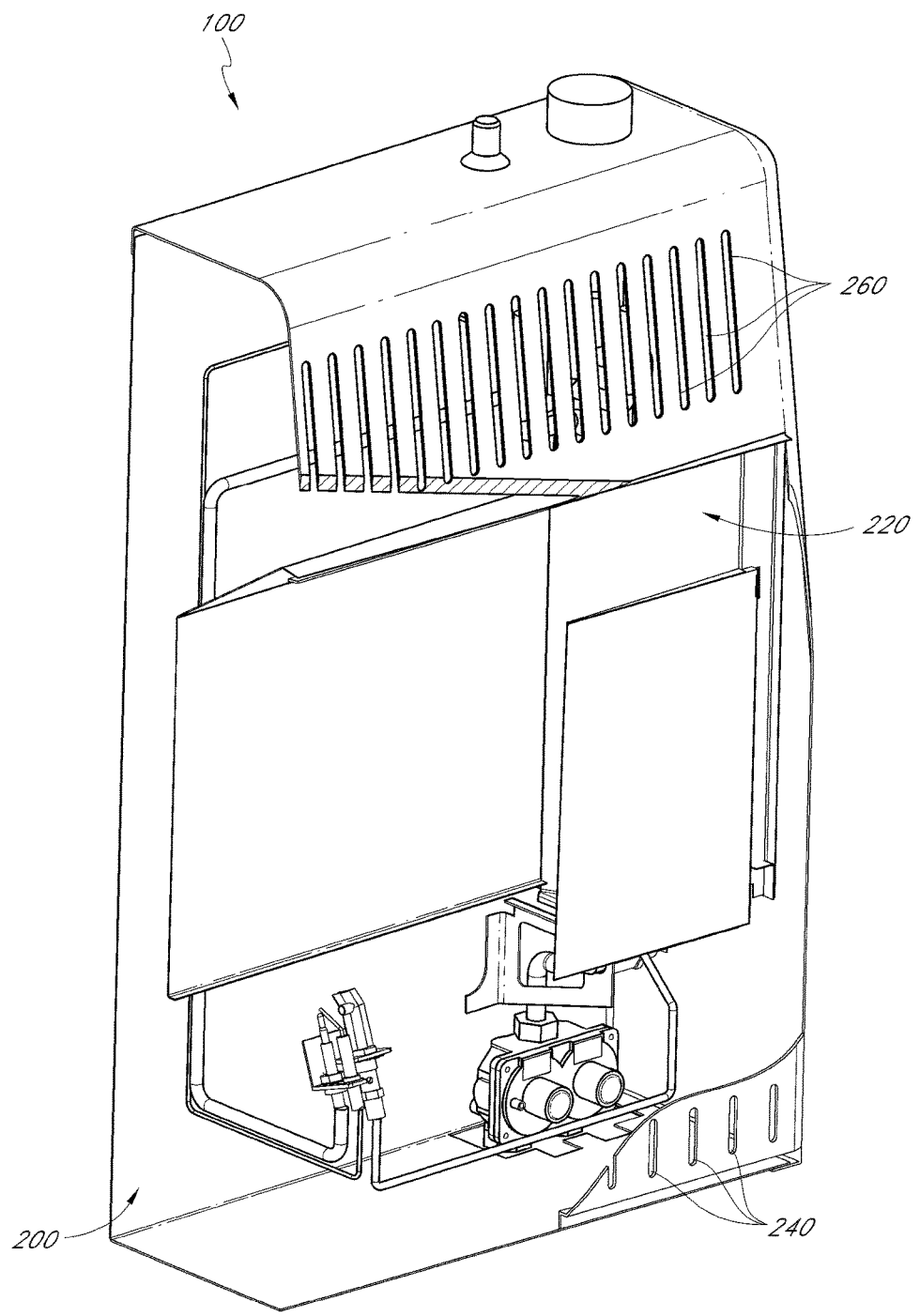
FIG. 1 is a perspective cutaway view of a portion of one embodiment of a heater configured to operate using either a first fuel source or a second fuel source.

FIG. 1 illustrates one embodiment of a heater 100. The heater 100 can be a vent-free infrared heater, a vent-free blue flame heater, or some other variety of heater, such as a direct vent heater. Some embodiments include boilers, stoves, dryers, fireplaces, gas logs, etc. Other configurations are also possible for the heater 100. In many embodiments, the heater 100 is configured to be mounted to a wall or a floor or to otherwise rest in a substantially static position. In other embodiments, the heater 100 is configured to move within a limited range. In still other embodiments, the heater 100 is portable.

The heater 100 can comprise a housing 200. The housing 200 can include metal or some other suitable material for providing structure to the heater 100 without melting or otherwise deforming in a heated environment. In the illustrated embodiment, the housing 200 comprises a window 220, one or more intake vents 240 and one or more outlet vents 260. Heated air and/or radiant energy can pass through the window 220. Air can flow into the heater 100 through the one or more intake vents 240 and heated air can flow out of the heater 100 through the outlet vents 260.

Within the housing 200, the heater 100, or other gas appliance, can include a heating assembly or heating source 10. A heating assembly 10 can include at least one or more of the components described herein.

With reference to FIG. 2, in certain embodiments, the heater 100 includes a regulator 120. The regulator 120 can be coupled with an output line or intake line, conduit, or pipe 122. The intake pipe 122 can be coupled with a control valve 130, which, in some embodiments, includes a knob 132. As illustrated, the control valve 130 is coupled to a fuel supply pipe 124 and an oxygen depletion sensor (ODS) pipe 126. The fuel supply pipe 124 can be coupled with a nozzle 160. The oxygen depletion sensor (ODS) pipe 126 can be coupled with an ODS 180. In some embodiments, the ODS comprises a thermocouple 182, which can be coupled with the control valve 130, and an igniter line 184, which can be coupled with an igniter switch 186. Each of the pipes 122, 124, and 126 can define a fluid passageway or flow channel through which a fluid can move or flow.

In some embodiments, including the illustrated embodiment, the heater 100 comprises a burner 190. The ODS 180 can be mounted to the burner 190, as shown. The nozzle 160 can be positioned to discharge a fluid, which may be a gas, liquid, or combination thereof into the burner 190. For purposes of brevity, recitation of the term "gas or liquid" hereafter shall also include the possibility of a combination of a gas and a liquid.

Where the heater 100 is a dual fuel heater, either a first or a second fluid is introduced into the heater 100 through the regulator 120. Still referring to FIG. 2, the first or the second fluid proceeds from the regulator 120 through the intake pipe 122 to the control valve 130. The control valve 130 can permit a portion of the first or the second fluid to flow into the fuel supply pipe 124 and permit another portion of the first or the second fluid to flow into the ODS pipe 126. From the control valve 130, the first or the second fluid can proceed through the fuel supply pipe 124, through the nozzle 160 and is delivered to the burner 190. In addition, a portion of the first or the second fluid can proceed through the ODS pipe 126 to the ODS 180. Other configurations are also possible.

Figures 3A, 3B, 3C:
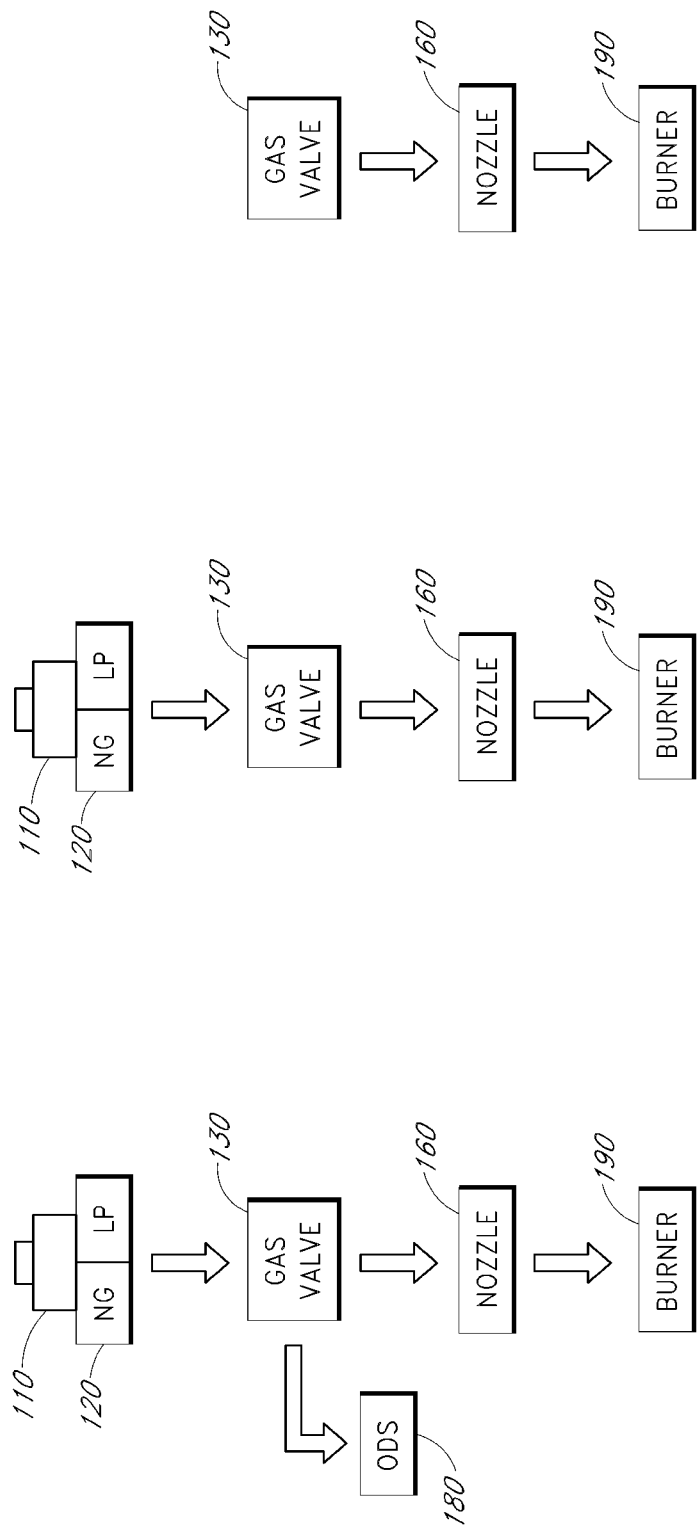
FIGS. 3A-C show some of the various possible combinations of components of a heating assembly 10.

FIGS. 3A-C show some of the various possible combinations of components of a heating assembly 10. Such heating assemblies can be made to be single fuel, dual fuel or multi-fuel gas appliances. For example, the heating assembly 10 can be made so that the installer of the gas appliance can connect the assembly to one of two fuels, such as either a supply of natural gas (NG) or a supply of propane (LP) and the assembly will desirably operate in the standard mode (with respect to efficiency and flame size and color) for either gas.

FIG. 3A illustrates a dual fuel system, such as a vent free heater. In some embodiments, a dual fuel heating assembly can include a fuel selector valve 110, a regulator 120, a control valve or gas valve 130, a nozzle 160, a burner 190 and an ODS 180. The arrows indicate the flow of fuel through the assembly. As can be seen in FIG. 3B, a dual fuel heating assembly, such as a regulated stove or grill, can have similar components to the heating assembly shown in FIG. 3A, but without the ODS. Still further heating assemblies, such as shown in FIG. 3C, may not have a fuel selector valve 110 or a regulator 120. This gas system is unregulated and can be an unregulated stove or grill, among other appliances. The unregulated system can be single fuel, dual fuel or multi-fuel. In some embodiments, and as described in more detail below, one or more of the fuel selector valve, ODS and nozzle, in these and in other embodiments can function in a pressure sensitive manner.

Figure 4A:
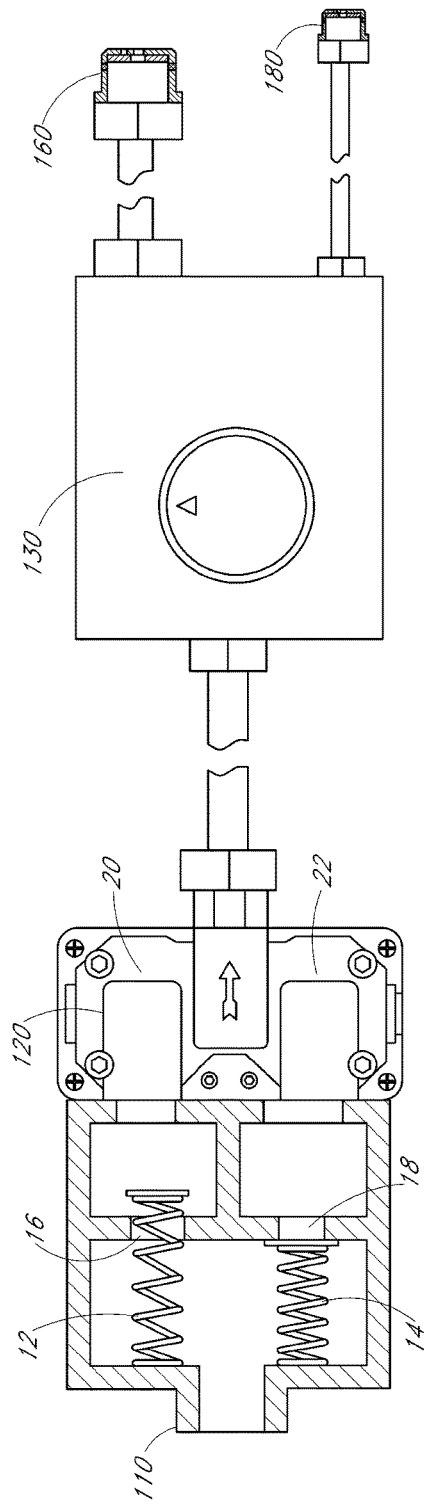
FIGS. 4A-B illustrate an embodiment of a heating assembly in schematic, showing a first configuration for liquid propane and a second configuration for natural gas.
Figure 4B:
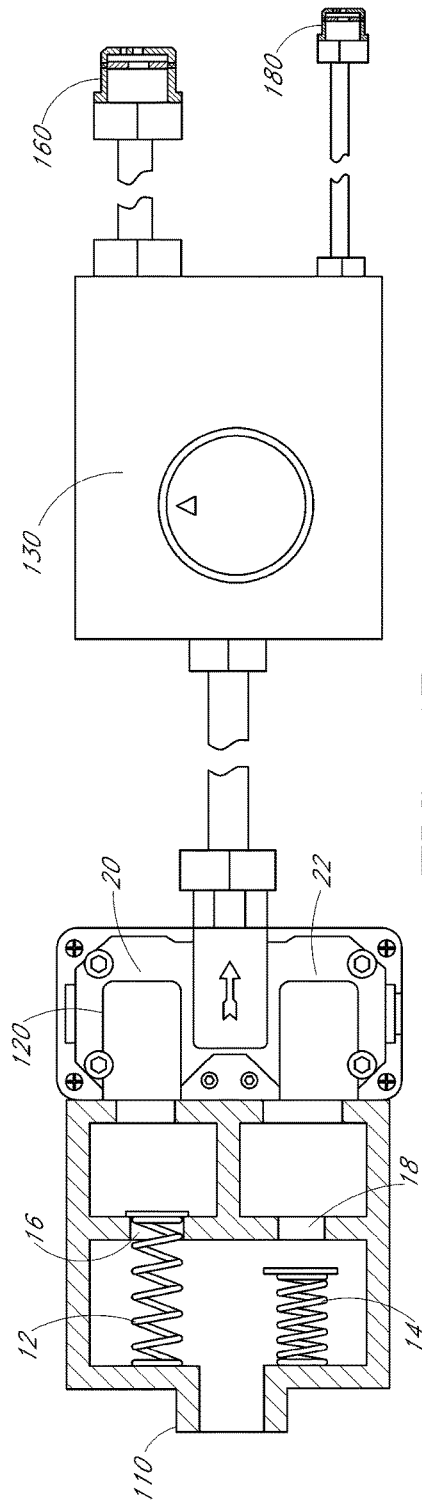

For example, turning to FIGS. 4A-B, a schematic representation of a heating assembly is shown first in a state for liquid propane (FIG. 4A) and second in a state for natural gas (FIG. 4B). Looking at the fuel selector valve 110, it can be seen that the pressure of the fluid flow through the valve 110 can cause the gate, valve or door 12, 14 to open or close, thus establishing or denying access to a channel 16, 18 and thereby to a pressure regulator 20, 22. The gate, valve or door 12, 14 can be biased to a particular position, such as being spring loaded to bias the gate 12 to the closed position and the gate 14 to the open position. In FIG. 4A, the gate 12 has been forced to open channel 16 and gate 14 has closed channel 18. This can provide access to a pressure regulator 20 configured to regulate liquid propane, for example. FIG. 4B shows the fuel selector valve 110 at a rest state where the pressure of the flow is not enough to change to state of the gates 12, 14 and channel 18 is open to provide access to pressure regulator 22, which can be configured to regulate natural gas, for example. As will be described herein after, the nozzle 160 and the ODS 180 can be configured to function in similar ways so that the pressure of the fluid flow can determine a path through the component. For example, the natural gas state (FIG. 4B) can allow more fluid flow than the liquid propane state (FIG. 4A) as represented by the arrows.

Figure 5:
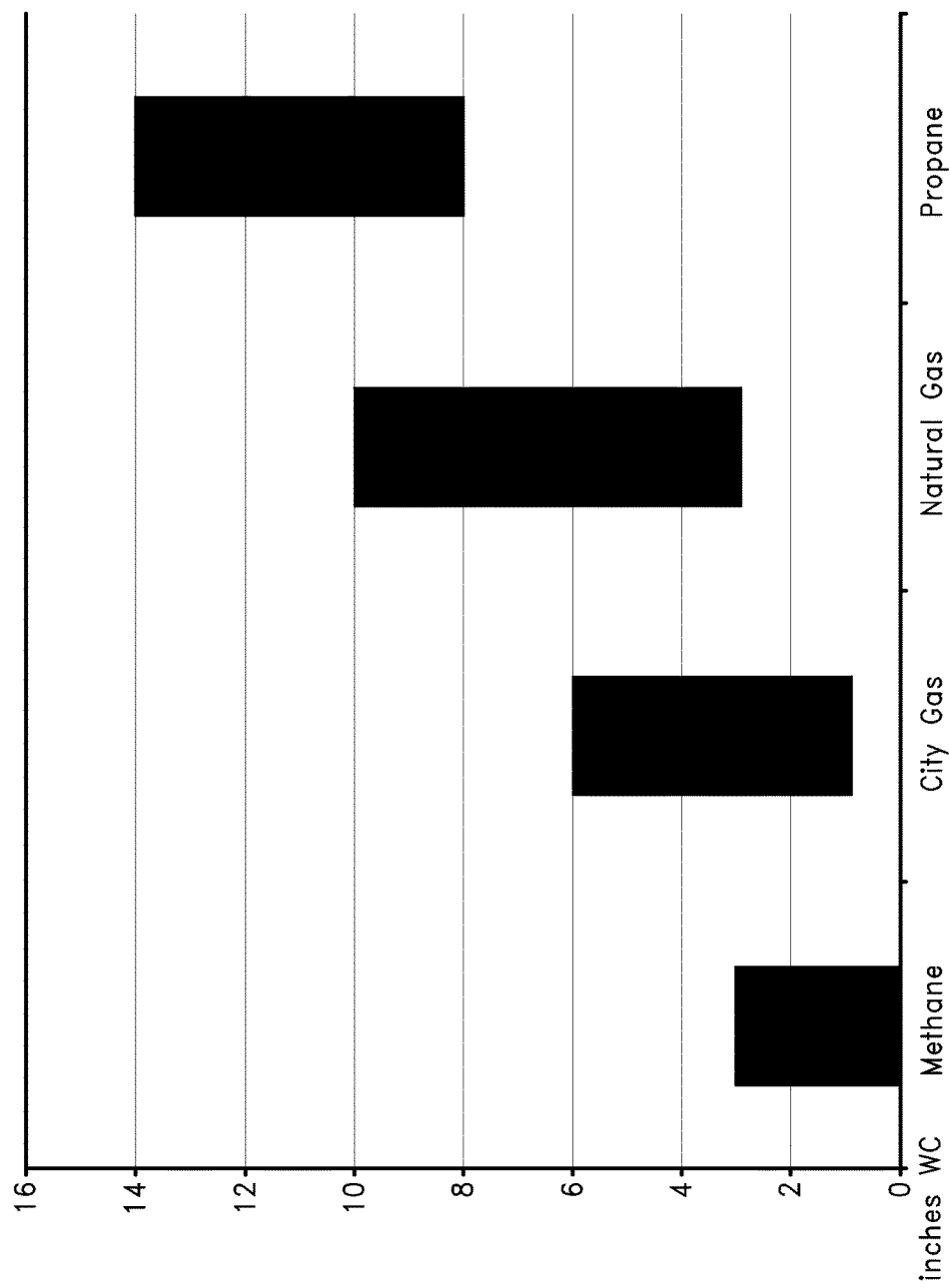
FIG. 5 is a chart showing typical gas pressures of different fuels.

Different fuels are generally run at different pressures. FIG. 5 shows four different fuels: methane, city gas, natural gas and liquid propane; and the typical pressure range of each particular fuel. The typical pressure range can mean the typical pressure range of the fuel as provided by a container, a gas main, a gas pipe, etc. and for consumer use, such as the gas provided to an appliance. Thus, natural gas may be provided to a home gas oven within the range of 3 to 10 inches of water column. The natural gas can be provided to the oven through piping connected to a gas main. As another example, propane may be provided to a barbeque grill from a propane tank with the range of 8 to 14 inches of water column. The delivery pressure of any fuel may be further regulated to provide a more certain pressure range or may be unregulated. For example, the barbeque grill may have a pressure regulator so that the fuel is delivered to the burner within the range of 10 to 12 inches of water column rather than within the range of 8 to 14 inches of water column.

As shown in the chart, city gas can be a combination of one or more different gases. As an example, city gas can be the gas typically provided to houses and apartments in China, and certain other countries. At times, and from certain sources, the combination of gases in city gas can be different at any one given instant as compared to the next.

Because each fuel has a typical range of pressures that it is delivered at, these ranges can advantageously be used in a heating assembly to make certain selections in a pressure sensitive manner. Further, certain embodiments may include one or more pressure regulators and the pressure of the fluid flow downstream of the pressure regulator can be generally known so as to also be able to make certain selections or additional selections in a pressure sensitive manner.

Figure 6:
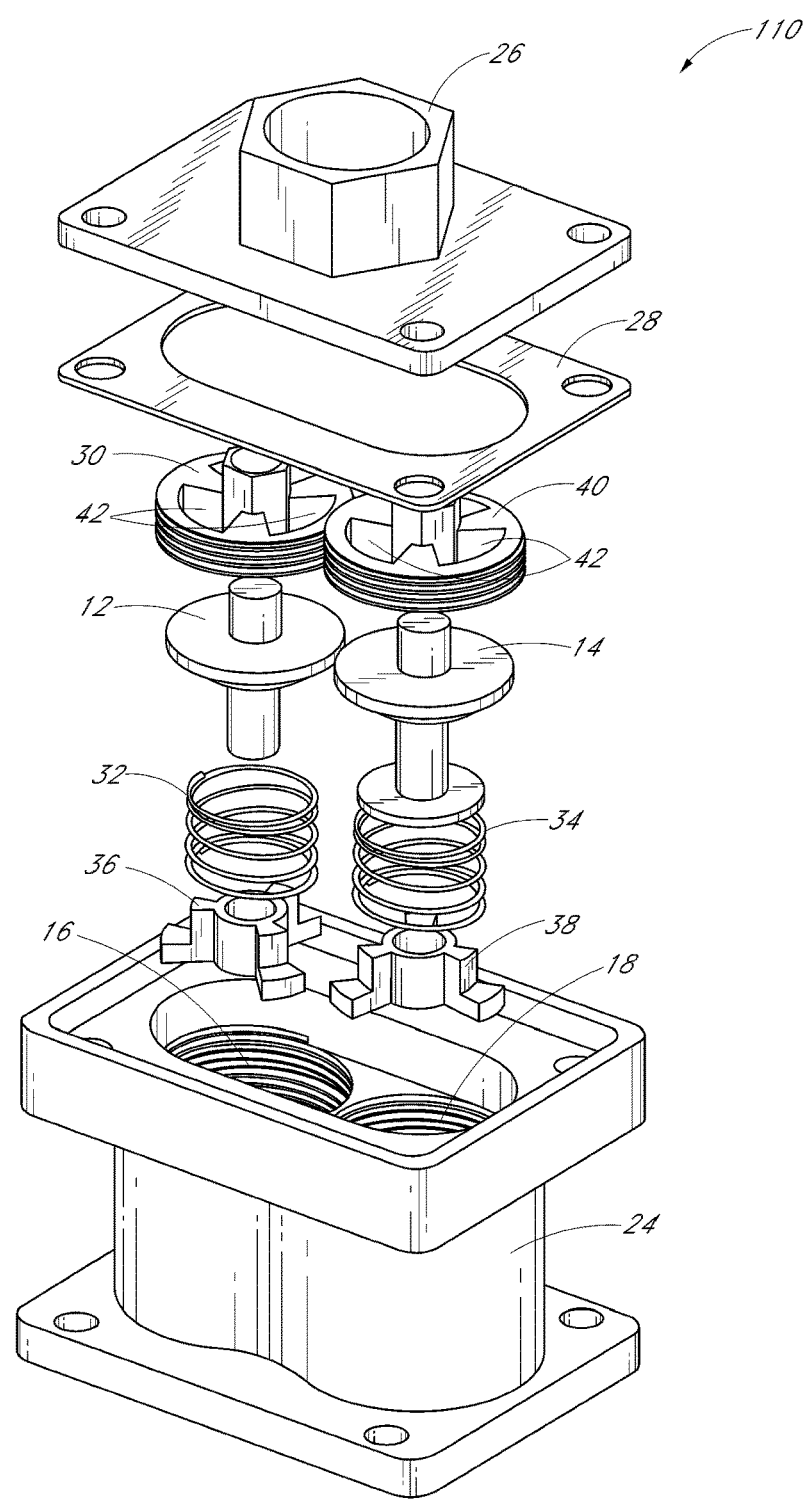
FIG. 6 is an exploded view of an embodiment of a fuel selector valve.

FIG. 6 illustrates the components of an embodiment of a fuel selector valve 110. The fuel selector valve 110 can be for selecting between two different fuels. The fuel selector valve 110 can have a first mode configured to direct a flow of a first fuel (such as natural gas or NG) in a first path through the fuel selector valve and a second mode configured to direct a flow of a second fuel (such as liquid propane or LP) in a second path through the fuel selector valve. This can be done in many different ways such as the opening and/or closing of one or more valves, gates, or doors 12, 14 to establish various flow paths through the fuel selector valve 110. The opening and/or closing of one or more valves, gates, or doors can be performed in a pressure sensitive manner, as explained below.

As illustrated, the fuel selector valve 110 of FIGS. 6-8B includes a main housing 24, a fuel source connection 26, a gasket 28 and valves 12, 14. A heating assembly 10 can connect to a fuel source at the fuel source connection 26. The fuel source connection 26 can be threaded or otherwise configured to securely connect to a fuel source. The main housing 24 can define channels 16, 18 and the valves 12, 14 can reside within the channels 16, 18 in the main housing 24. The housing 24 can be a single piece or a multi-piece housing.

Figures 8A, 8B:
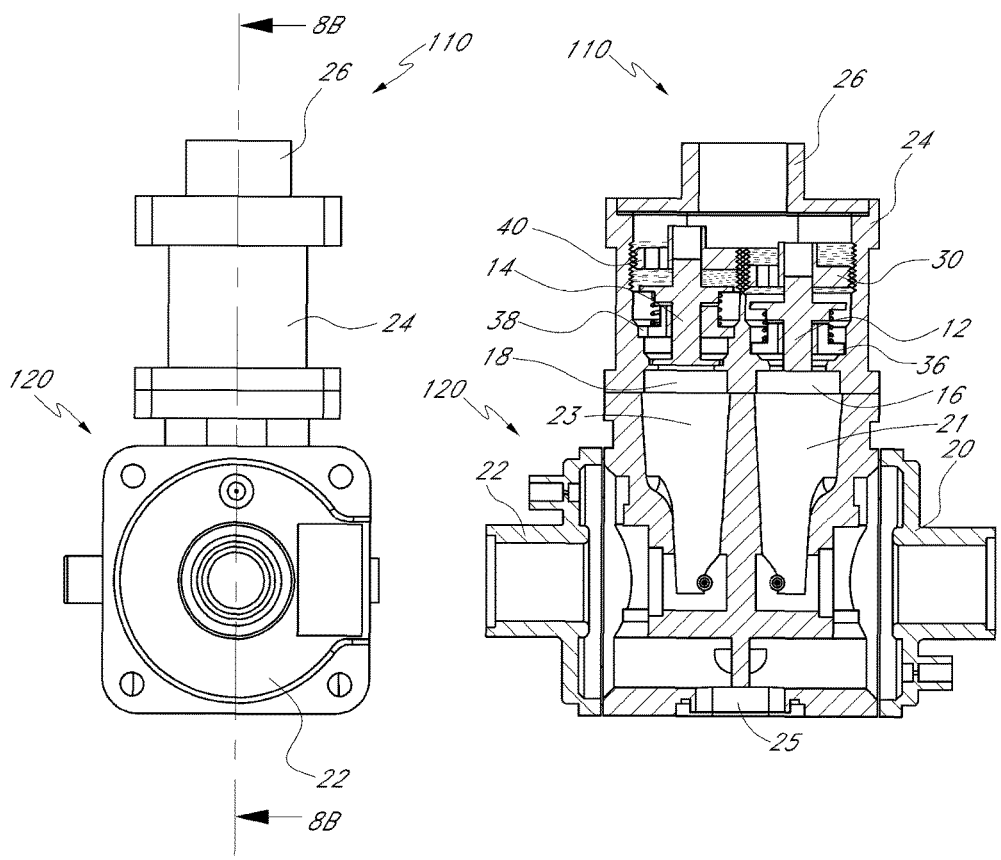
FIG. 8A is a side view of an embodiment of a fuel selector valve and pressure regulator.
FIG. 8B is a cross-section of the fuel selector valve and pressure regulator of FIG. 8A.

As will be shown hereafter, in the various embodiments, there can be one or more valves, gates, or doors 12, 14 that can function in different ways, as well as one or more channels 16, 18 within the housing 24. The gates, doors or valves 12, 14 can work in many different ways to open or close and to thereby establish or deny access to a channel 16, 18. The channels 16, 18 can direct fluid flow to an appropriate flow passage, such as to the appropriate pressure regulator 20, 22, if pressure regulators are included in the heating assembly (FIGS. 8A-B). For example, channel 16 can direct flow to a first inlet 23 on a regulator 120 that connects to pressure regulator 22 and channel 18 can direct flow to a second inlet 21 that connects to pressure regulator 20. Both pressure regulators 20, 22 can direct flow to the outlet 25. Though a regulator 120 is shown that combines the two pressure regulators 20, 22 into one housing other configurations are also possible.

The shown fuel selector valve 110 of FIGS. 6-8B further includes, biasing members 32, 34, front portions 30, 40 and rear portions 36, 38. Biasing members 32, 34 can be metal springs, elastic, foam or other features used to bias the valves 12, 14 to a particular position, such as being spring loaded to bias both valves 12, 14 to the closed position. Further, the fuel selector valve 110 can be set such that each valve 12, 14 will open and/or close at different pressures acting on the valve. In this way, the fuel selector valve 110 can use fluid pressure to select a flow pathway through the valve. In some embodiments, this can be a function of the spring force of each individual spring, as well as the interaction of the spring with the valve. In some embodiments, the position of the spring and the valve can be adjusted to further calibrate the pressure required to open the valve 12, 14.

For example, the front portions 30, 40 can be threadedly received into the channels 16, 18. This can allow a user to adjust the position of the front portions 30, 40 within the channels and thereby adjust the compression on the spring, as can best be seen in FIG. 7A. In this illustrated embodiment, the spring 32, 34 is located between the valve 12, 14 and the respective rear portion 36, 38. The spring biases the valve to the closed position where it contacts the front portion 30, 40. Each front portion 30, 40 has holes 42 passing therethrough that are blocked by the valve when the valve is in contact with the front portion. Thus, the adjustment of the position of the front portion with respect to the valve can affect the amount of pressure required to move the valve away from the front portion to open the valve. In some embodiments, the front portions 30, 40 can be adjustable from outside the housing 24. This can allow for the valve 110 to be calibrated without having to disassemble the housing 24. In other embodiments, such as that shown, the front portions 30, 40 can be preset, such as at a factory, and are not accessible from outside the housing 24. This can prevent undesired modification or tampering with the valve 110. Other methods and systems of calibration can also be used.

Figure 7A:
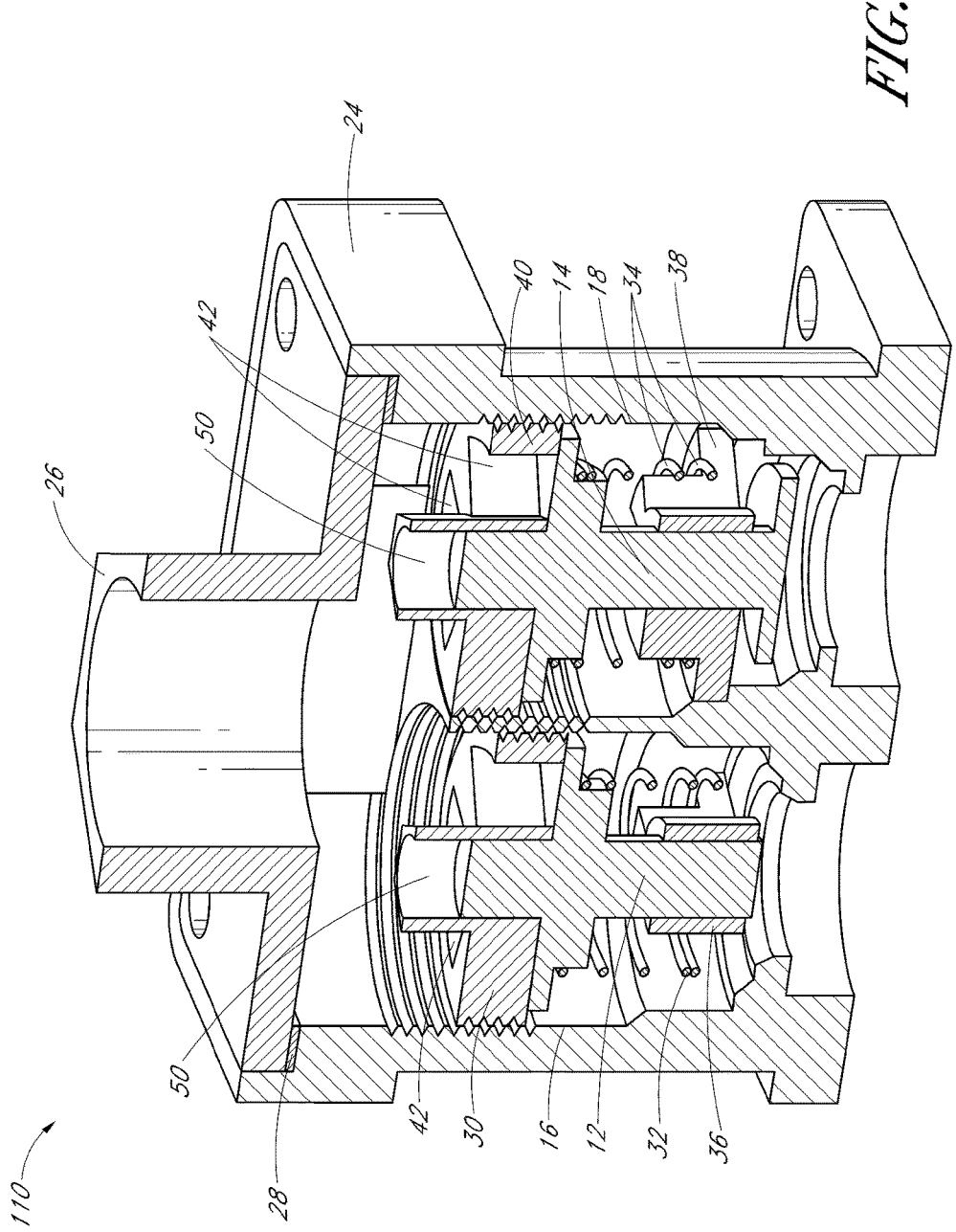
FIGS. 7A-C are cross-sectional views of the fuel selector valve of FIG. 6 in first, second and third positions, respectively.
Figure 7B:
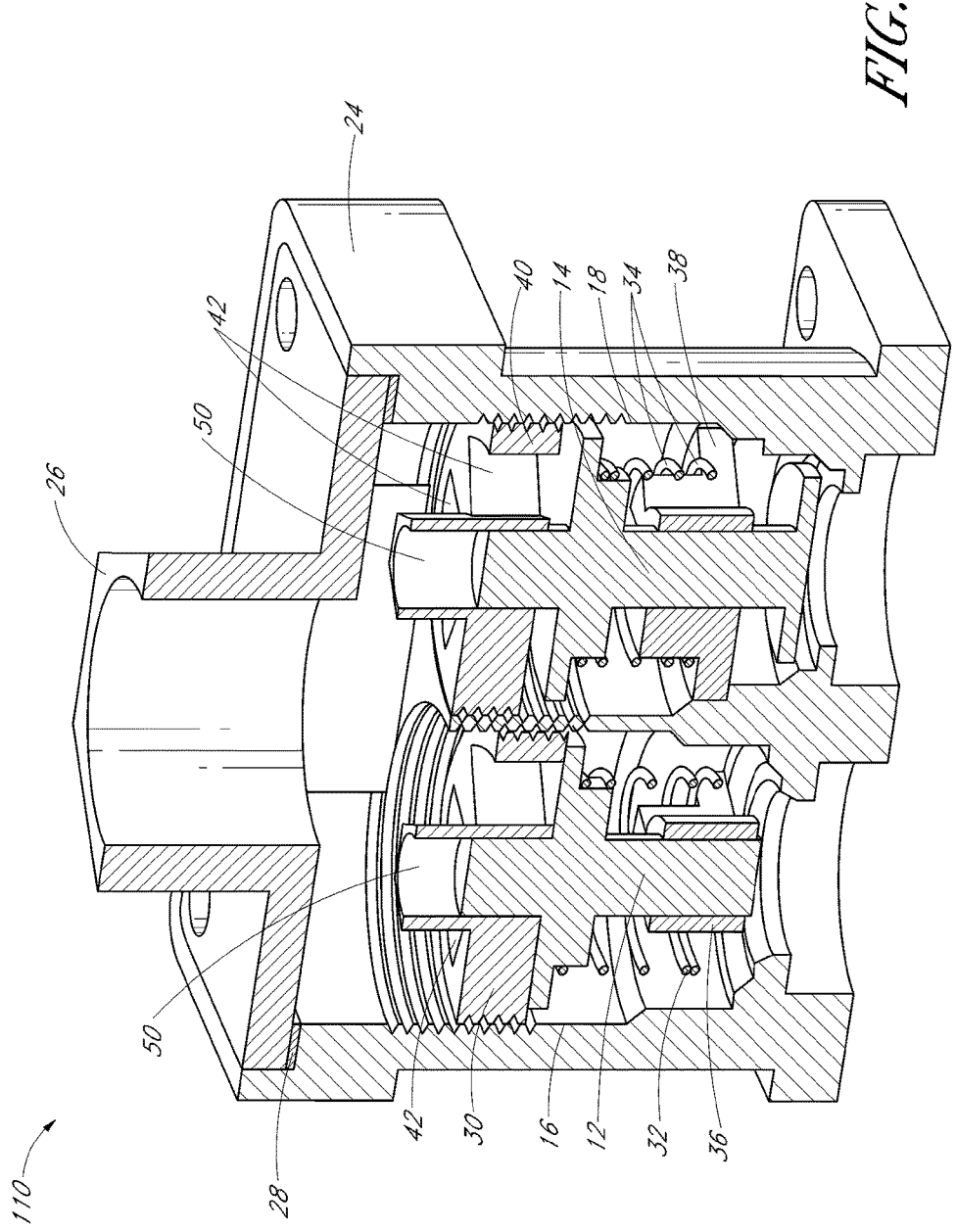

Fluid pressure acting on the valve 12, 14, such as through the holes 42 can force the valve to open. FIG. 7A shows a first open position where a threshold amount of pressure has been achieved to cause the valve 14 to open, while valve 12 still remains closed. FIG. 7B illustrates a second open position where a second threshold pressure has been reached to close valve 14 at the rear end of the valve, and a third threshold pressure has been achieved to open valve 12. In some embodiments, the second and third threshold pressures can be the same. In some embodiments, the third threshold pressure can be greater than the second and the first threshold pressures. Of course, this may change for different configurations, such as where the springs interact and bias the valves in different ways and to different positions.

In some embodiments, the fuel selector valve 110 can be used in a dual fuel appliance, such as an appliance configured to use with NG or LP. In this situation, the first threshold pressure to open valve 14 may be set to be between about 3 to 8 inches of water column, including all values and sub-ranges therebetween. In some embodiments, the first threshold pressure is about: 3, 4, 5, 6, 7 or 8 inches of water column. The second threshold pressure to close valve 14 may be set to be between about 5 to 10 inches of water column, including all values and sub-ranges therebetween. The third threshold pressure to open valve 12 can be set to be between about 8 to 12 inches of water column, including all values and sub-ranges therebetween. In some embodiments, the third threshold pressure is about: 8, 9, 10, 11 or 12 inches of water column. In a preferred embodiment, the first and second threshold pressures are between about 3 to 8 inches of water column, where the second is greater than the first and the third threshold pressure is between about 10 to 12 inches of water column. In this embodiment, as in most dual fuel embodiments, the ranges do not overlap.

Returning now to calibration, for certain springs, as the spring is compressed it can require a greater force to further compress the spring. Thus, moving the front portion 30, 40 away from the respective valve 12, 14 would decrease the force required to initially compress the spring, such as to move the valve 14 from a closed position (FIG. 7A) to an open position (FIG. 7B). The reverse would also be true, moving the front portion closer to the valve would increase the force required to initially compress the spring.

In some embodiments, a spring can be used that has a linear spring force in the desired range of movement, compression or extension, used in the fuel selection valve. The spring force for a particular use of a particular spring can be based on many different factors such as material, size, range of required movement, etc.

Figure 7C:
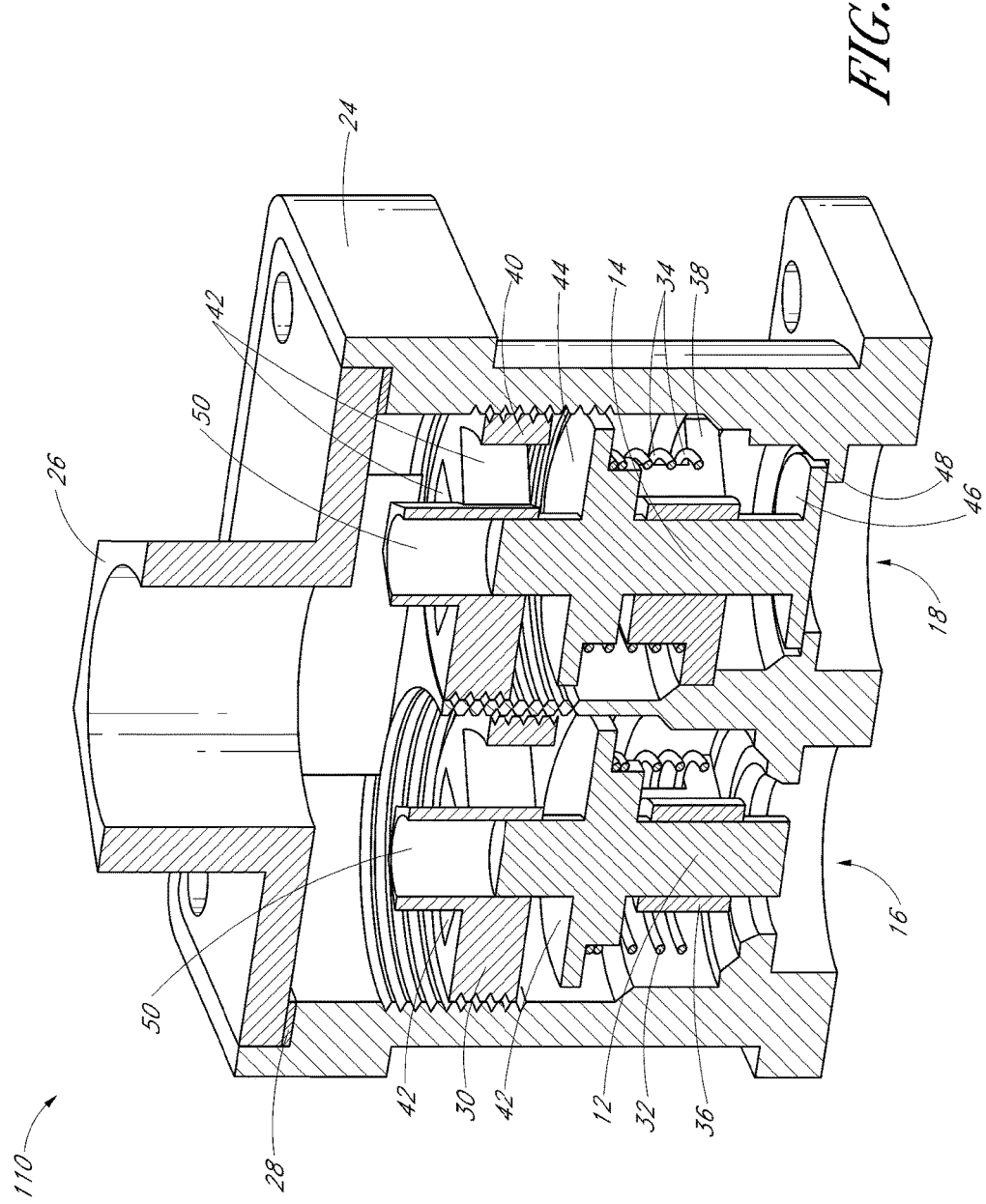

Turning now to FIG. 7C, the valves 12, 14 will now be discussed in more detail. Each valve 12, 14 can form one of more valve seats to prevent fluid flow from passing the valve or to redirect fluid flow in a particular manner. For example, valve 12 has a forward ledge portion 43 and valve 14 has a forward ledge portion 44 and a rearward ledge portion 46, all of which are used to seat the valve 12, 14 against another surface and close the valve. As shown, the forward ledge portions 43, 44 seat with the front portions 30, 40 and the rearward ledge portion 46 seats with a ledge 48 within the outer housing 24. Other configurations are also possible, such as a valve with a portion that seats in multiple locations within the outer housing, for example to have a first closed position, on open position and a second closed position. A front face and a back face of a ledge on a valve could be used to seat the valve, as one further example.

The front 30, 40 and rear 36, 38 portions can be used to position the valve 12, 14 within the housing 24. For example, the rear portions 36, 38 can surround a central region of the valve and the valve can move or slide within the rear portion. Further the spring 32, 34 can be between the valve and the rear portion. The front portions 30, 40 can have one or more holes 42 passing therethrough. Fluid pressure acting on the valve 12, 14, such as through the holes 42 can force the valve to open. In some embodiments, the front portions 30, 40 can have a channel 50. The channel 50 can be used to guide movement of the valve. In addition, the channel can direct fluid flow at the valve to open the valve. Because there are no exits in the channel, fluid flow does not pass around the valve but rather remains constantly acting against the valve as long as there is flow through the fuel selector valve 110.

In other embodiments, the front and/or rear portions can be permanently or integrally attached to the housing 24. Some embodiments do not have either or both of a front or rear portion.

FIGS. 9-22 show schematic representations of various other designs for a fuel selector valve 110. Each set of figures "A" & "B" represent the fuel selector valve in a first state (A) and a second state (B) where a fluid flow pressure would preferably be greater in the second state.

Figure 9A:
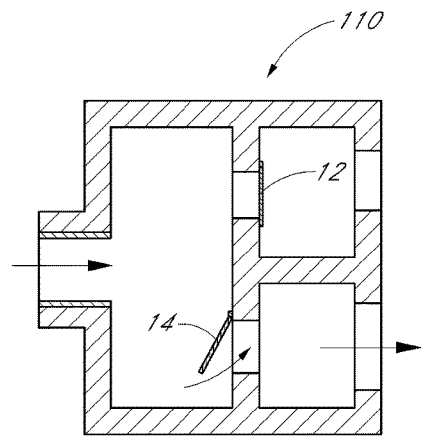
FIGS. 9A-B are schematic cross-sectional views of a fuel selector valve in a first position and a second position.
Figure 9B:
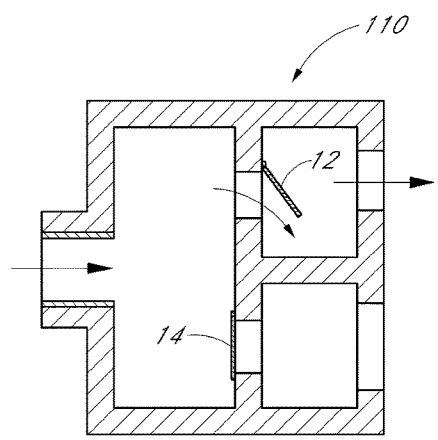

FIGS. 9A-B show a series of gates 12, 14. In the initial position and at the first fluid flow, gate 14 is open and gate 12 is closed. An increased fluid pressure acts on the gates to close gate 14 and to open gate 12. The gates can be resilient and can act as springs. Thus, once the pressure is decreased, the gates can return to their initial positions.

Figure 10A:
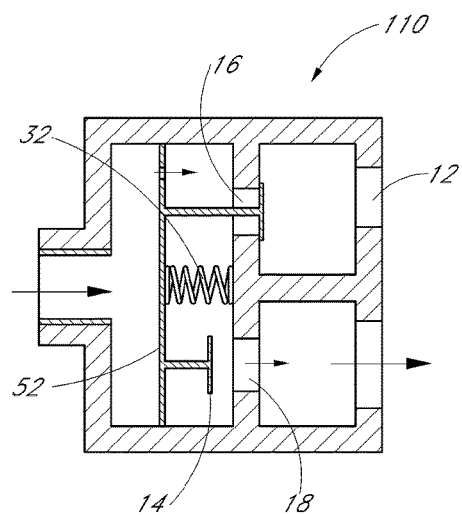
FIGS. 10A-B are schematic cross-sectional views of a fuel selector valve in a first position and a second position.
Figure 10B:
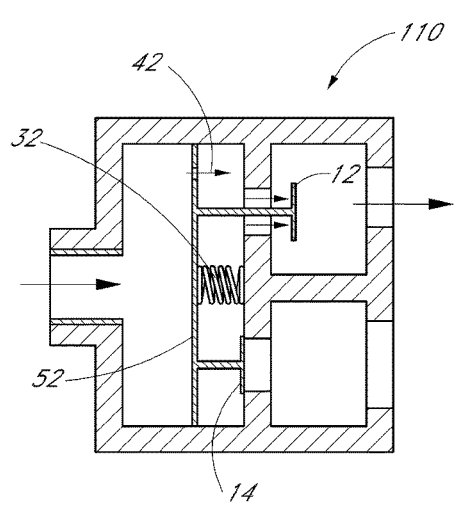

FIGS. 10A-B includes a pressure plate 52 and a spring 32, where fluid pressure can act on the pressure plate 52 to move it from the initial position where one channel 18 is open to the second position where the original channel 18 is closed and a second channel 16 is open. The pressure plate 52 can have one or more holes 42 to allow fluid to flow through the plate 52 in some locations. In some embodiments the plate 52 can be smaller than the internal chamber so that fluid can flow around the plate instead or in addition to through the plate.

Figure 11A:
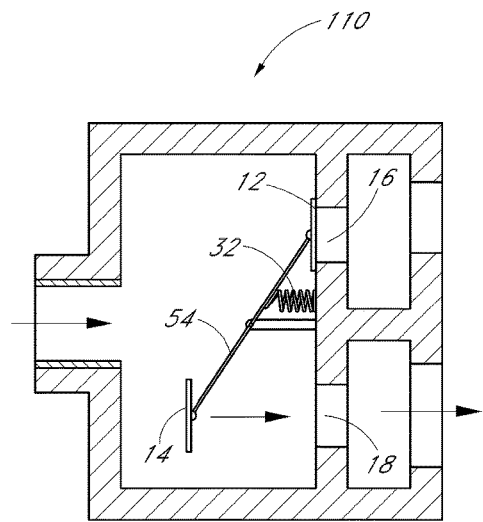
FIGS. 11A-B are schematic cross-sectional views of a fuel selector valve in a first position and a second position.
Figure 11B:
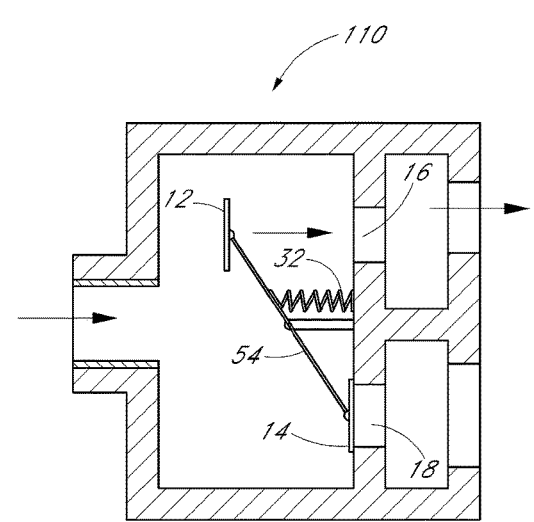

FIGS. 11A-B show a series of gates 12, 14 in a teeter-totter configuration and a spring 32. Gate 14 has an increased surface area compared to gate 12 so that more of the fluid flow and pressure will act on gate 14. In the initial position and at the first fluid flow, gate 14 is open and gate 12 is closed. An increased fluid pressure acts on gate 14 to close channel 18 while expanding the spring 32. This also opens gate 12 because the gates are connected by connecting rod 54.

Figure 12A:
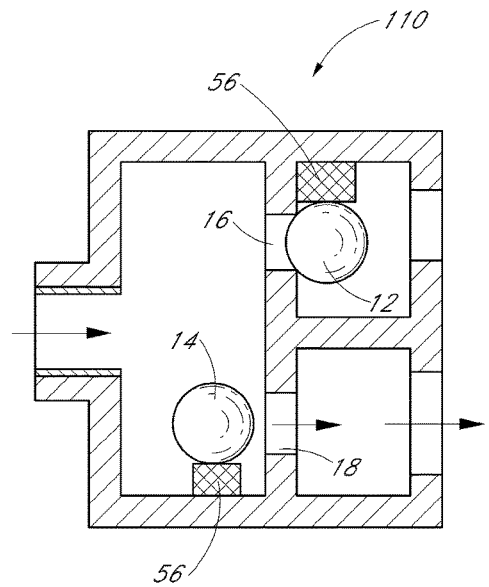
FIGS. 12A-B are schematic cross-sectional views of a fuel selector valve in a first position and a second position.
Figure 12B:
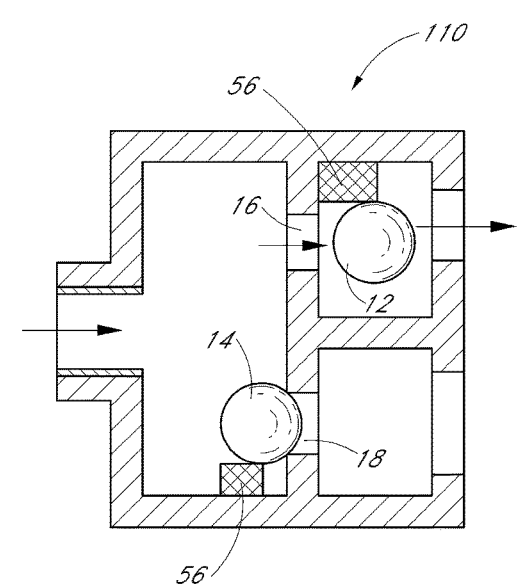
Figure 16A:
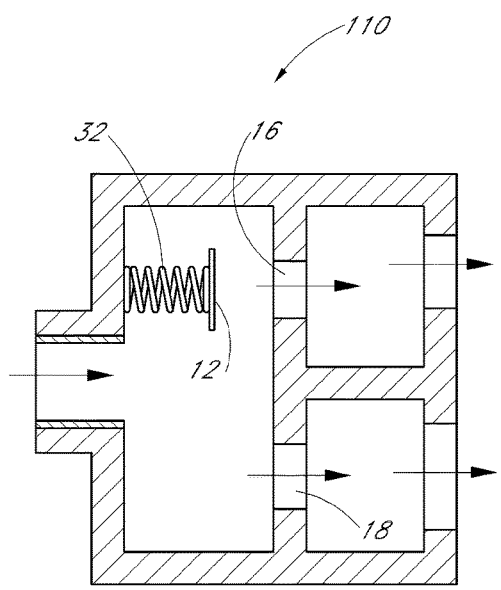
FIGS. 16A-B are schematic cross-sectional views of a fuel selector valve in a first position and a second position.
Figure 16B:
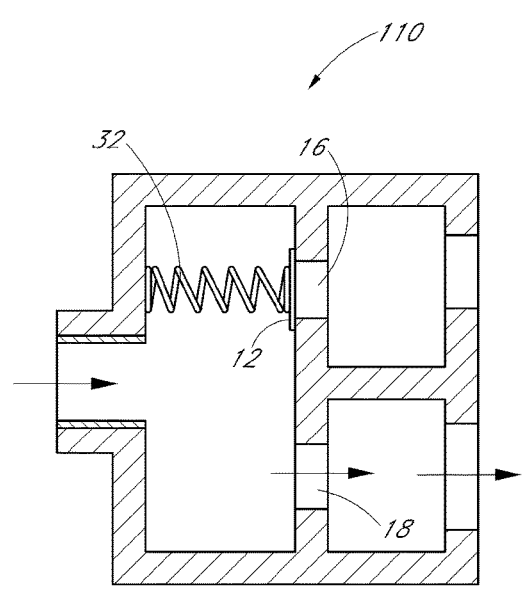
Figure 17A:
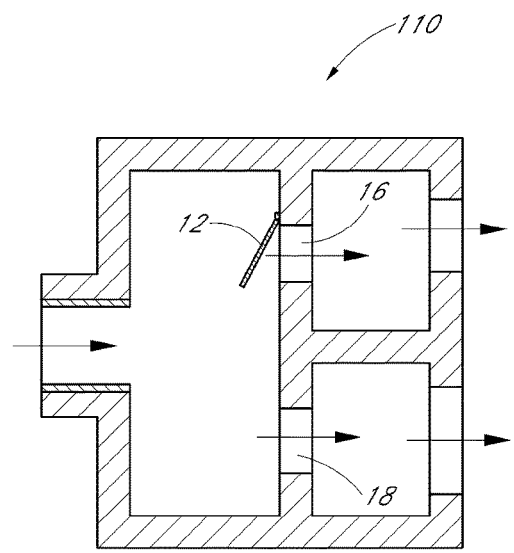
FIGS. 17A-B are schematic cross-sectional views of a fuel selector valve in a first position and a second position.
Figure 17B:
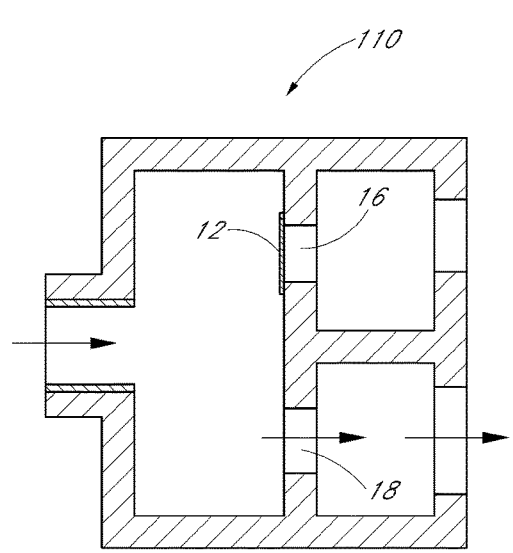
Figures 18A, 18B:
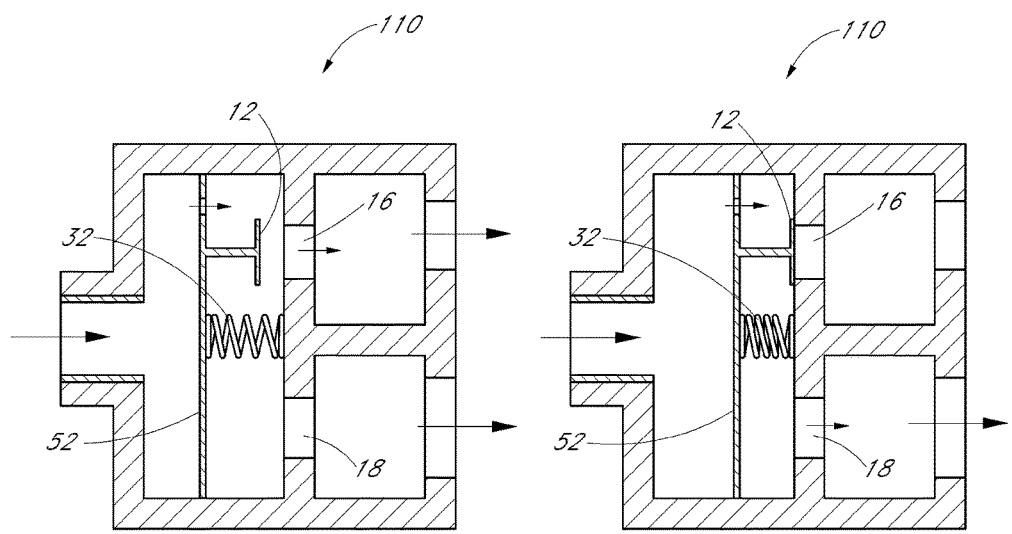
FIGS. 18A-B are schematic cross-sectional views of a fuel selector valve in a first position and a second position.
Figures 19A, 19B:
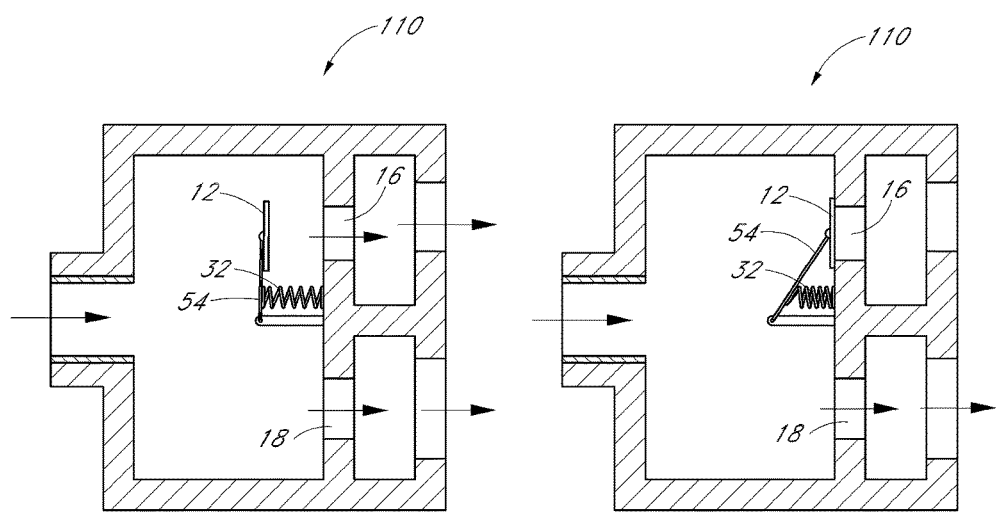
FIGS. 19A-B are schematic cross-sectional views of a fuel selector valve in a first position and a second position.
Figure 20A:
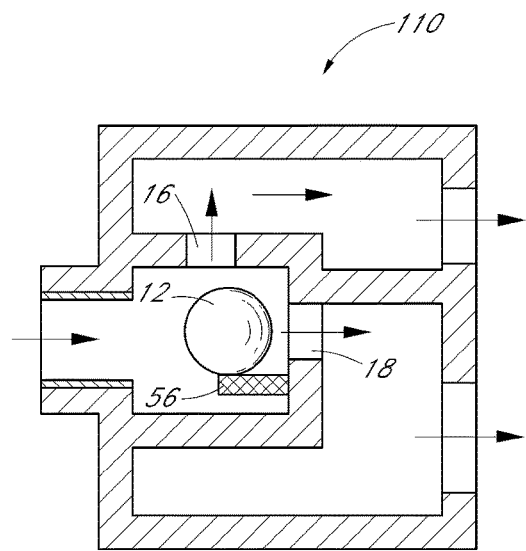
FIGS. 20A-B are schematic cross-sectional views of a fuel selector valve in a first position and a second position.
Figure 20B:
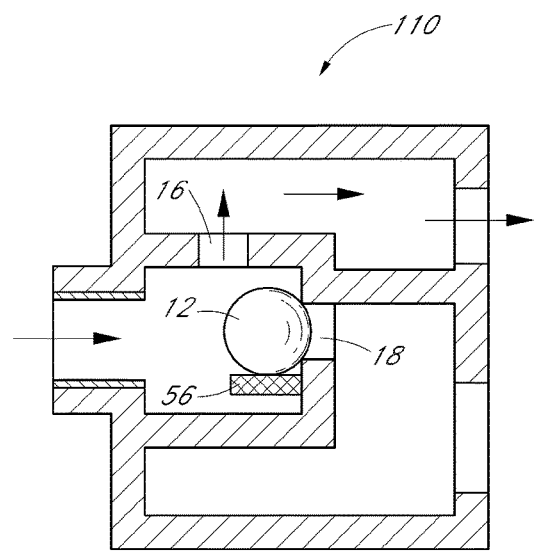
Figure 21A:
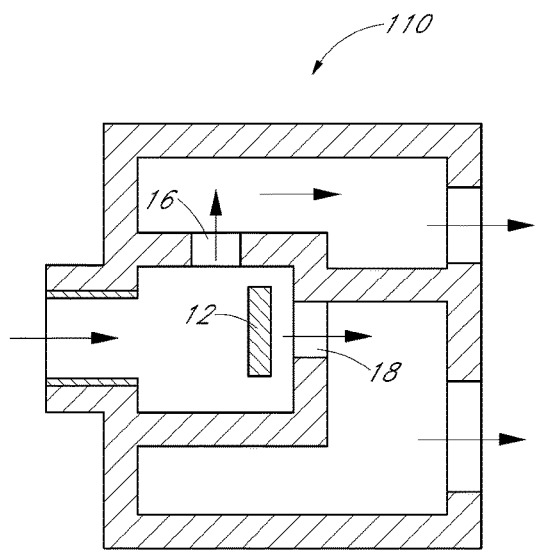
FIGS. 21A-B are schematic cross-sectional views of a fuel selector valve in a first position and a second position.
Figure 21B:
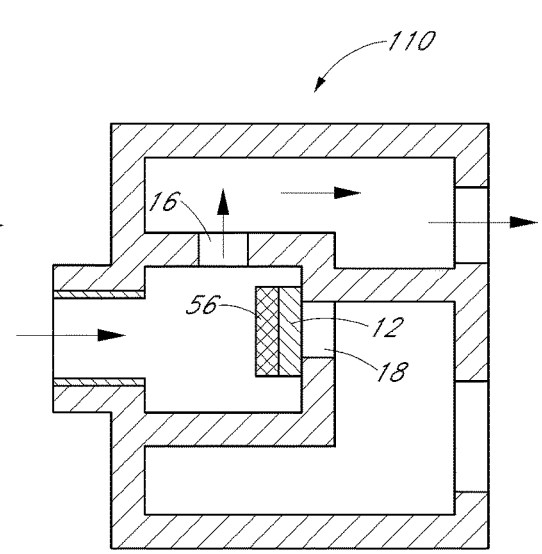
Figure 22A:
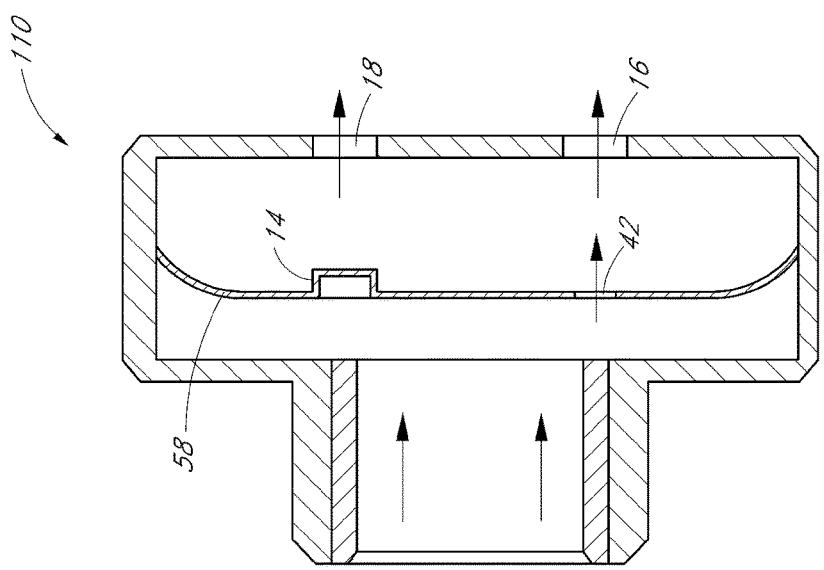
FIGS. 22A-B are schematic cross-sectional views of a fuel selector valve in a first position and a second position.
Figure 22B:
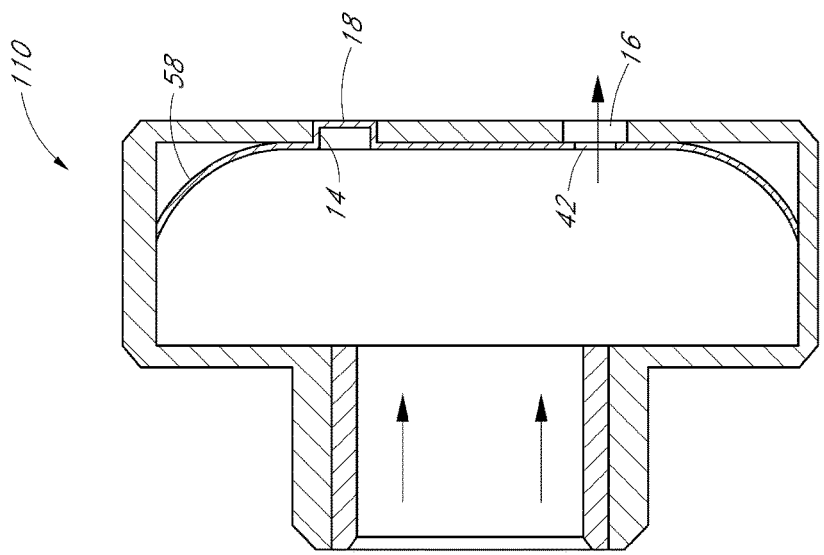

FIGS. 12A-B show a series of gates 12, 14 in the form of steel balls connected to magnets 56. The initial fluid flow pressure is not enough to overcome the magnetic attraction between the steel balls 12, 14 and the magnets 56. Thus, gate 14 remains open and gate 12 remains closed. Increased fluid pressure overcomes the attraction and the steel balls move from their initial position to close gate 14 and to open gate 12. Once the pressure is decreased, the magnet 56 will cause the ball to return to the initial position.

FIGS. 13A-B is very similar to FIGS. 12A-B except that only one steel ball and a magnet are used instead to two and the ball blocks one path in the first position and blocks another path in the second. FIGS. 14A-B show a magnet and sliding gate 12, similar to the single steel ball and magnet in FIGS. 13A-B. Holes 42 passing through the gate 12 allow fluid to flow through the gate in the initial position but are blocked in the second position.

FIGS. 15A-B show a diaphragm that works in a similar manner to the pressure plate of FIGS. 10A-B. An increased pressure causes the diaphragm to move. In the initial position and at the first fluid flow, channel 18 open and channel 16 is closed. An increased fluid pressure acts on the diaphragm to plug channel 18 with gate 14 and to open gate 12. Gate 12 can be part of a tension rod 60 which may also include a spring 32. The tension rod can have holes 42 therethrough to allow flow past the diaphragm. Moving the diaphragm advances the rod and the gate 12 is moved away from channel 16 to allow flow therethrough. Once the pressure is decreased, the gates can return to their initial positions.

Each of FIGS. 9-15 illustrates a fuel selector valve 110 that makes a selection between one of two exits. FIGS. 16-22 show other embodiments with two or more exits where generally all of the exits can be open, and then one or more of the exits can be blocked. As will be readily apparent to one skilled in the art, the fuel selector valves of FIGS. 16-22 function is similar ways to the fuel selector valves shown in FIGS. 9-15 and described above.

It will be understood that any of the pressure sensitive valves described herein, whether as part of a fuel selector valve, nozzle, or other component of the heating assembly, can function in one of many different ways, where the valve is controlled by the pressure of the fluid flowing through the valve. For example, many of the embodiments shown herein comprise helical or coil springs. Other types of springs, or devices can also be used in the pressure sensitive valve. Further, the pressure sensitive valves can operate in a single stage or a dual stage manner. Many valves described herein both open and close the valve under the desired circumstances (dual stage), i.e. open at one pressure for a particular fuel and close at another pressure for a different fuel. Single stage valves may also be used in many of these applications. Single stage valves may only open or close the valve, or change the flow path through the valve in response to the flow of fluid. Thus for example, the fuel selector valve 110 shown in FIG. 7A is shown with a single stage valve 12 and a dual stage valve 14. The dual stage valve 14 can be modified so that the valve is open in the initial condition and then closes at a set pressure, instead of being closed, opening at a set pressure and then closing at a set pressure. In some instances, it is easier and less expensive to utilize and calibrate a single stage valve as compared to a dual stage valve. In some embodiments, the valve can include an offset. The offset can offset the valve away from the front or rear portion, so that the valve cannot be closed at either the front or back end respectively. Offsets can also be used to ensure the valve does not move beyond a certain position. For example, an offset can be used that allows the valve to close, but that prevents the valve from advancing farther, such as to prevent damage to the valve housing or housing wall.

As discussed previously, the fuel selector valve 110 can be used to determine a particular fluid flow path for a fluid at a certain pressure or in a pressure range. Some embodiments of heating assembly can include first and second pressure regulators 20, 22. The fuel selector valve 110 can advantageously be used to direct fluid flow to the appropriate pressure regulator without separate adjustment or action by a user.

In some embodiments, the first and second pressure regulators 20, 22 are separate and in some embodiments, they are connected in a regulator unit 120, as shown in FIGS. 4A-B & 8A-B. A regulator unit 120 including first and second pressure regulators 20, 22 can advantageously have a two-in, one-out fluid flow configuration, though other fluid flow configurations are also possible including one-in or two-out.

The pressure regulators 20, 22 can function in a similar manner to those discussed in U.S. application Ser. No. 11/443,484, filed May 30, 2006, now U.S. Pat. No. 7,607,426, incorporated herein by reference and made a part of this specification; with particular reference to the discussion on pressure regulators at columns 3-9 and FIGS. 3-7 of the issued patent.

The first and second pressure regulators 20, 22 can comprise spring-loaded valves or valve assemblies. The pressure settings can be set by tensioning of a screw that allows for flow control of the fuel at a predetermined pressure or pressure range and selectively maintains an orifice open so that the fuel can flow through spring-loaded valve or valve assembly of the pressure regulator. If the pressure exceeds a threshold pressure, a plunger seat can be pushed towards a seal ring to seal off the orifice, thereby closing the pressure regulator.

The pressure selected depends at least in part on the particular fuel used, and may desirably provide for safe and efficient fuel combustion and reduce, mitigate, or minimize undesirable emissions and pollution. In some embodiments, the first pressure regulator 20 can be set to provide a pressure in the range from about 3 to 6 inches of water column, including all values and sub-ranges therebetween. In some embodiments, the threshold or flow-terminating pressure is about: 3, 4, 5, or 6 inches of water column. In some embodiments, the second pressure regulator 22 can be configured to provide a second pressure in the range from about 8 to 12 inches of water column, including all values and sub-ranges therebetween. In some embodiments, the second threshold or flow-terminating pressure is about: 8, 9, 10, 11 or 12 inches of water column.

The pressure regulators 20, 22 can be preset at the manufacturing site, factory, or retailer to operate with selected fuel sources. In many embodiments, the regulator 120 includes one or more caps to prevent consumers from altering the pressure settings selected by the manufacturer. Optionally, the heater 100 and/or the regulator unit 120 can be configured to allow an installation technician and/or user or customer to adjust the heater 100 and/or the regulator unit 120 to selectively regulate the heater unit for a particular fuel source.

Returning now to FIGS. 3A-4B, fuel selector valves 110 and regulators 120 have been discussed above. As can be seen in the Figures, a heating source may or may not include a fuel selector valve 110 and/or a regulator 120. In some embodiments, a fuel source can be connected to a control valve 130, or the fuel selector valve and/or regulator can direct fuel to a control valve 130. The control valve 130 can comprise at least one of a manual valve, a thermostat valve, an AC solenoid, a DC solenoid and a flame adjustment motor. The control valve 130 can direct fuel to the burner 190 through a nozzle 160. The control valve 130 may also direct fuel to an ODS 180.

The control valve 130 can control the amount of fuel flowing through the control valve to various parts of the heating assembly. The control valve 130 can manually and/or automatically control when and how much fuel is flowing. For example, in some embodiments, the control valve can divide the flow into two or more flows or branches. The different flows or branches can be for different purposes, such as for an oxygen depletion sensor (ODS) 180 and for a burner 190. In some embodiments, the control valve 130 can output and control an amount of fuel for the ODS 180 and an amount of fuel for the burner 190.

Figure 23:
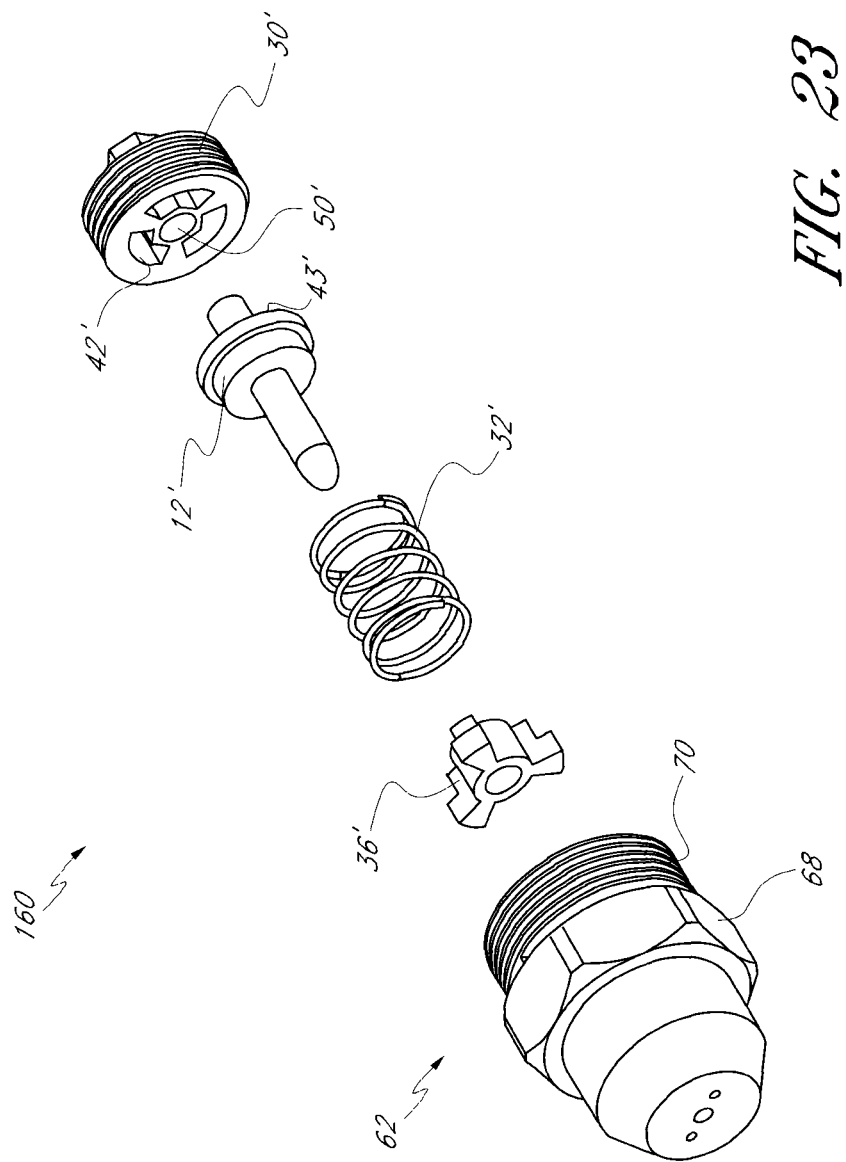
FIG. 23 shows an exploded view of an embodiment of a nozzle.

Turning now to the nozzle 160, one embodiment of a nozzle 160 is shown in FIGS. 23-23C. The nozzle 160 used in a heating assembly can be a pressure sensitive nozzle similar to the fuel selector valves 110 described herein. FIGS. 23-23C illustrate a nozzle 160 with an internal structure very similar to the fuel selector valve 110 shown in FIGS. 6-8B. The illustrated nozzle includes a front portion 30', a valve 12', a spring 32', and a rear portion 36'. All of which can be positioned inside a nozzle body 62. The nozzle body 62 can be a single piece or a multi-piece body.

The nozzle body can include a flange 68 and threads 70. The flange and threads can be used to attach the nozzle to another structure, such as a pipe or line running from the control valve. In some embodiments, the flange 68 is configured to be engaged by a tightening device, such as a wrench, which can aid in securing the nozzle 160 to a nozzle line. In some embodiments, the flange 68 comprises two or more substantially flat surfaces, and in other embodiments, is substantially hexagonal as shown.

The nozzle body 62 can define a substantially hollow cavity or pressure chamber 16'. The pressure chamber 16' can be in fluid communication with an inlet and an outlet. In some embodiments, the outlet defines an outlet area that is smaller than the area defined by the inlet. In preferred embodiments, the pressure chamber 16' decreases in cross-sectional area toward a distal end thereof.

Figure 24B:
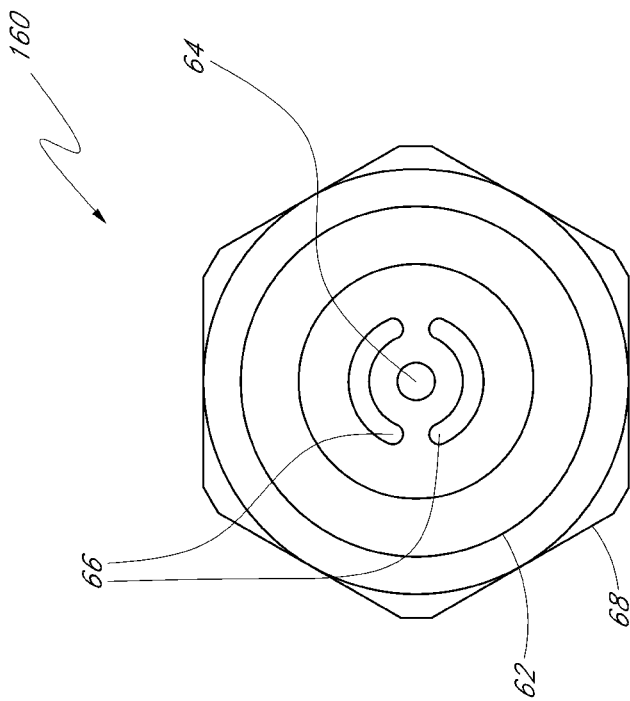
FIGS. 24A-B illustrate different configurations for an end of a nozzle.
Figure 24A:
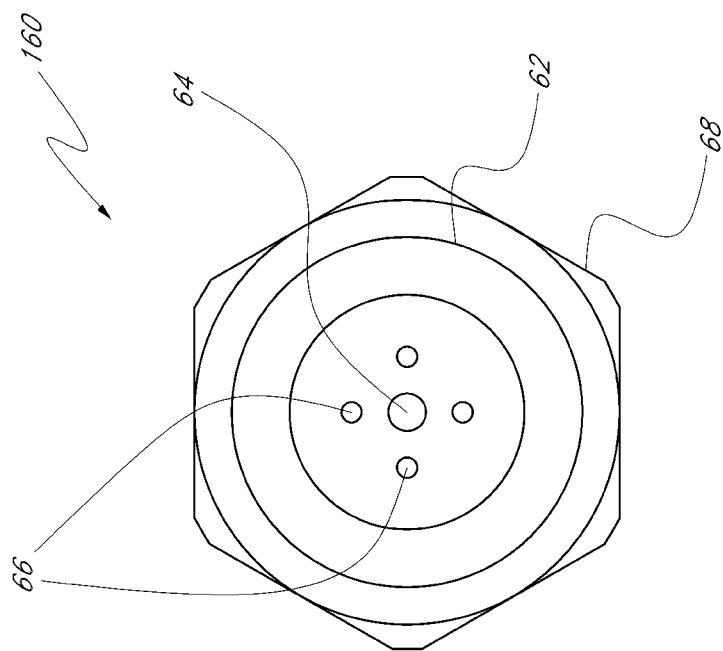

As can be seen, a front ledge 43' on the valve 12' can contact the front portion 30' such that the flow passages or holes 42' are blocked, when the nozzle is in the initial "off" position (FIG. 23A). The flow passages or holes 42' can define the inlet. Fluid flow into the nozzle 160 and acting on the valve 12', such as acting on the valve 12' by flowing through the holes 42' and the channel 50', can force the valve to compress the spring 32' and move such that fluid can flow through the nozzle 160. FIG. 23B shows the nozzle 160 in a first open position. Fluid is flowing through the nozzle and out the outlet holes or orifices 64, 66. Under certain fluid flows the pressure can cause the valve to advance farther within the nozzle 160 further compressing the spring 32'. In this situation, the valve 12' can reduce or block flow through the nozzle 160. As shown in FIG. 23C, flow through orifice 64 can be blocked by the valve 12', while one or more orifices 66 remain open. The orifices 66 can have one of many different configurations, such as comprising two, three, four, or more holes or slots as shown in FIGS. 23-24B. The orifice 64 can also have many different configurations.

The nozzle 160 can be used in single fuel, dual fuel or multi-fuel appliances. For example, the nozzle 160 can be used in a dual fuel appliance, such as an appliance configured for use with either of NG or LP. In this situation, the first threshold pressure to open valve 12' may be set to be between about 3 to 8 inches of water column (for NG), including all values and sub-ranges therebetween. In some embodiments, the first threshold pressure is about: 3, 4, 5, 6, 7 or 8 inches of water column. The second threshold pressure to close orifice 64 may be set to be above about 8 inches of water column (for LP). In some embodiments, the second threshold pressure is about: 8, 9, 10, 11 or 12 inches of water column. In this way the nozzle 160 can be used with different fuels and yet provide an amount of fuel to the burner 190 that will create similar size of flames and/or BTU values.

Similar to the fuel selector valve 110, the front portion 30' of the nozzle 160 can be adjusted to calibrate the threshold pressures. In some embodiments, the spring 32', as well as, other single or dual stage springs discussed herein, can have a spring constant (K) of about 0.0067 N/mm, between about 0.006-0.007 N/mm, or between about 0.005-8.008 N/mm. The spring can be approximately 7 mm, or between approximately 6-8 mm long. The spring can have an outer diameter between approximately 5-9 mm. The spring can be made from wire that is approximately 0.15 mm, 0.2 mm, or between approximately 0.1-0.3 mm in diameter. Other sizes, lengths and spring constants can also be used.

The nozzle 160 is shown together with a control valve 130 in FIG. 25A. Referring back to FIGS. 3A-C, it was pointed out that a heating assembly can have various different combinations of components and can be made to be single fuel, dual fuel or multi-fuel. The control valve 130, shown in FIG. 25A can be used in many different heating assemblies including those discussed with reference to FIGS. 3B-C. For example, the control valve can be a manual valve such as to adjust a flame height on a grill. The control valve 130 can direct fuel to the burner 190 through the nozzle 160. The control valve 130 could also be modified to control fuel flow to an ODS but such modifications are not shown.

Figure 25C:
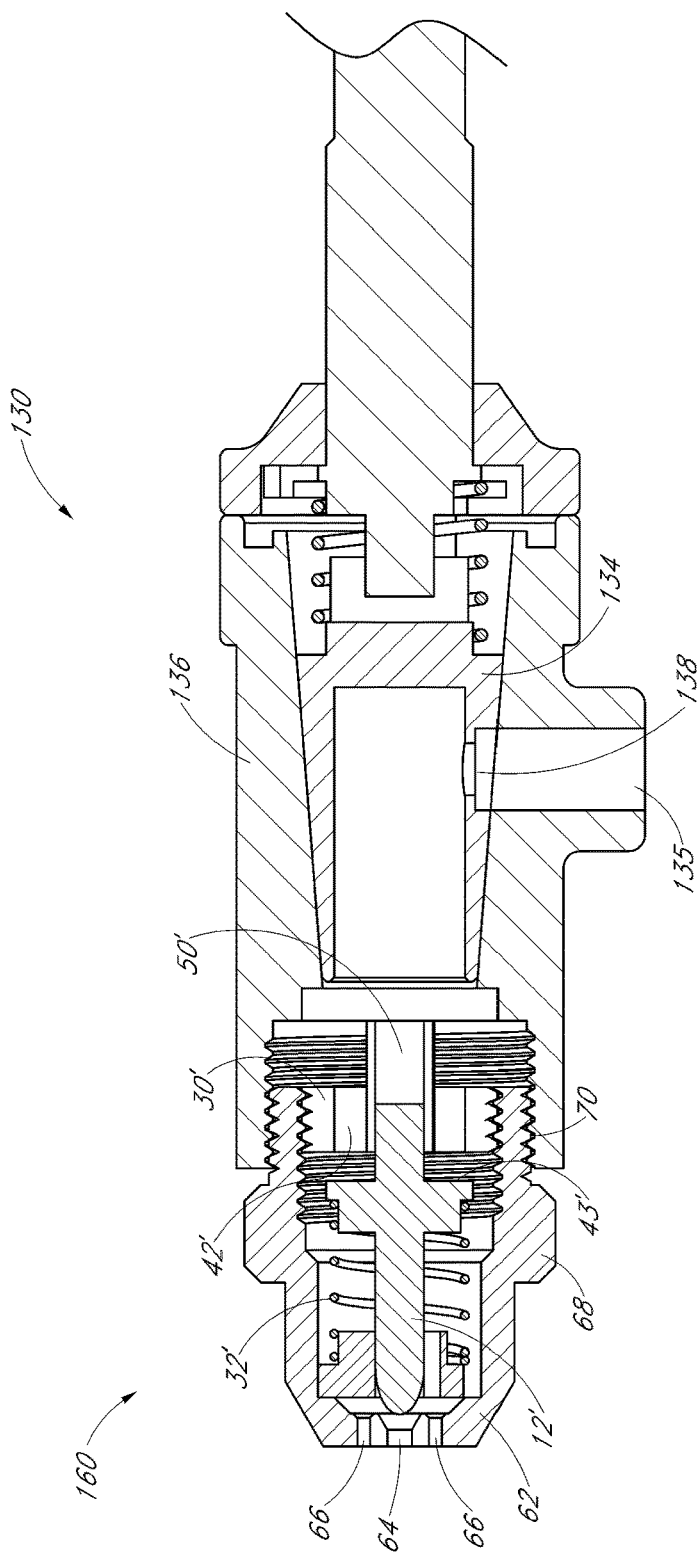
FIG. 25C is a cross-sectional view of the nozzle and control valve of FIG. 25A.
Figure 26A:
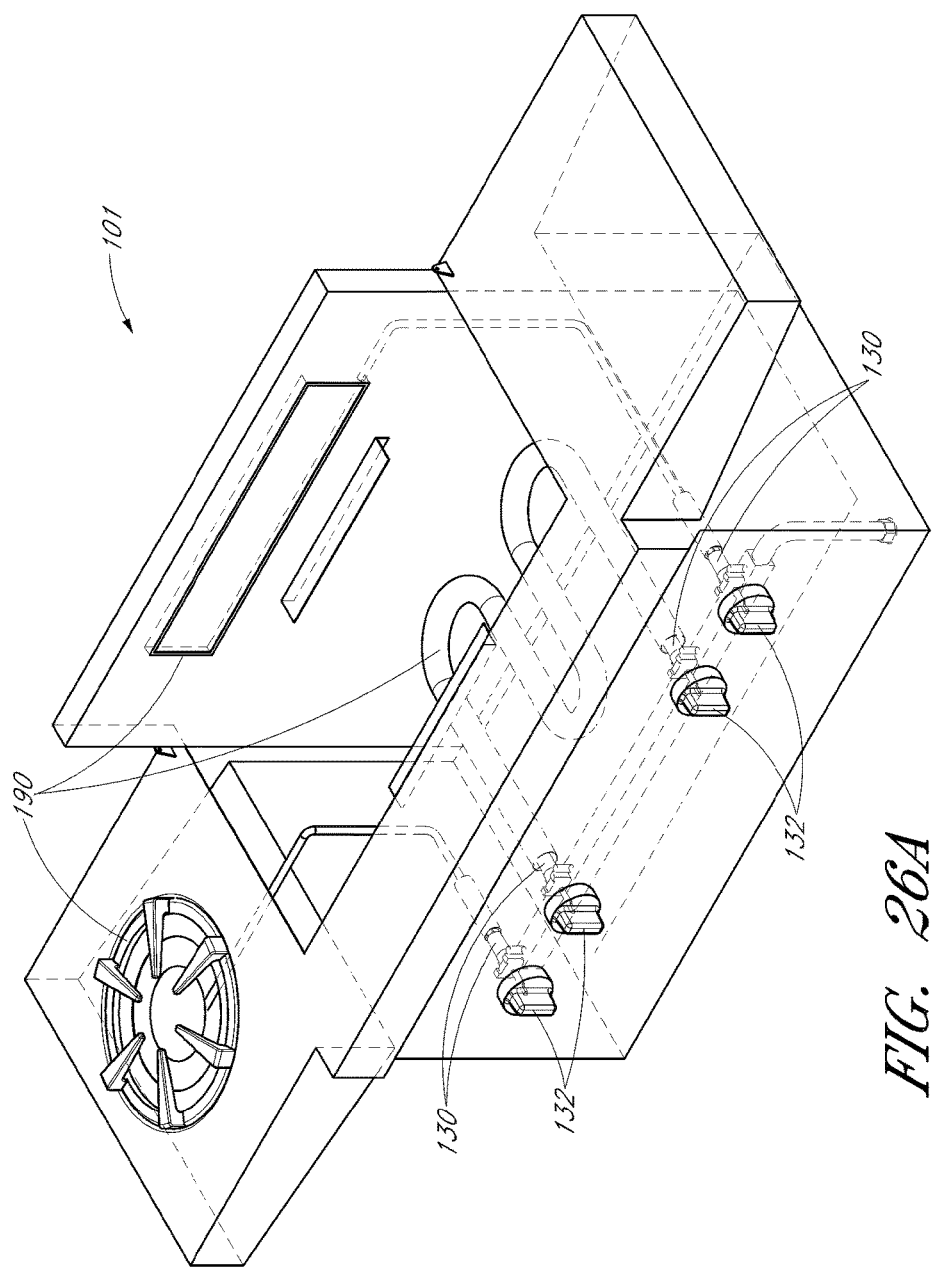
Figure 27A:
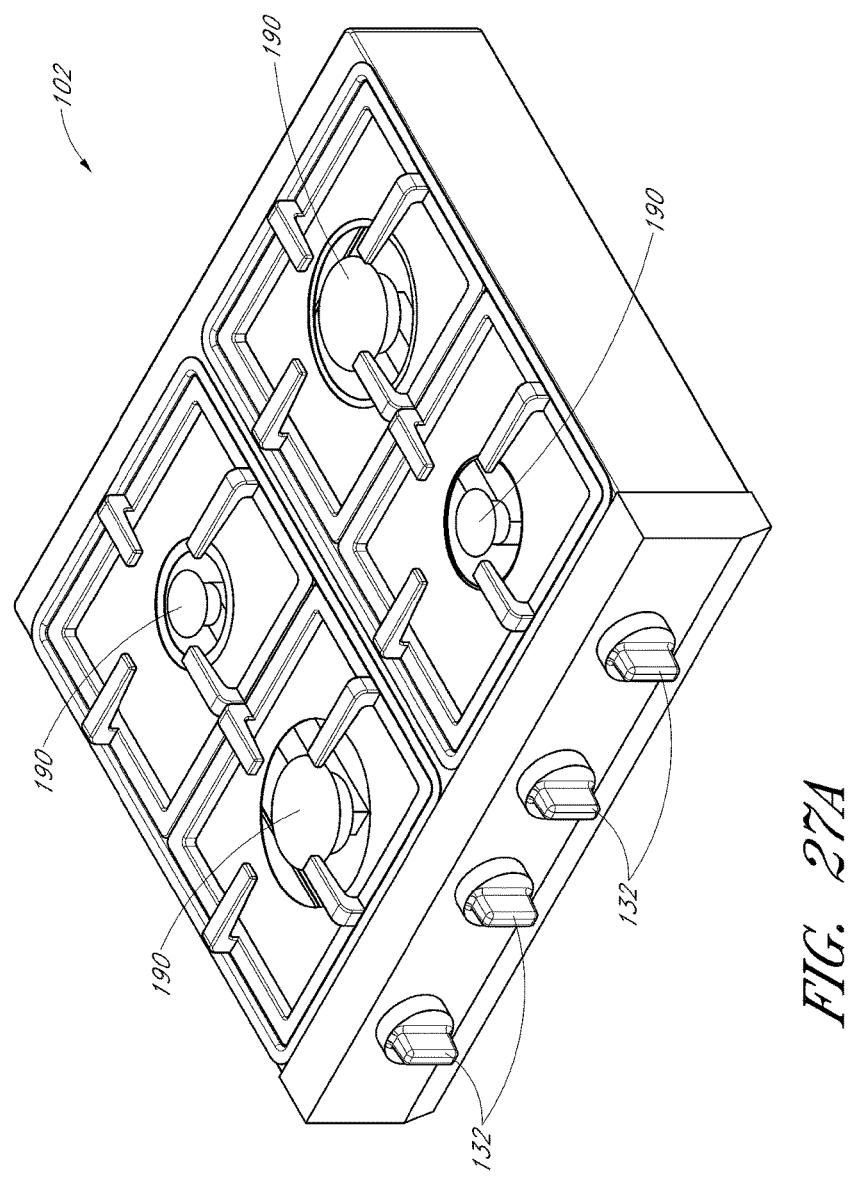
FIGS. 27A-B show perspective and bottom views respectively of a stove top.
Figure 27B:
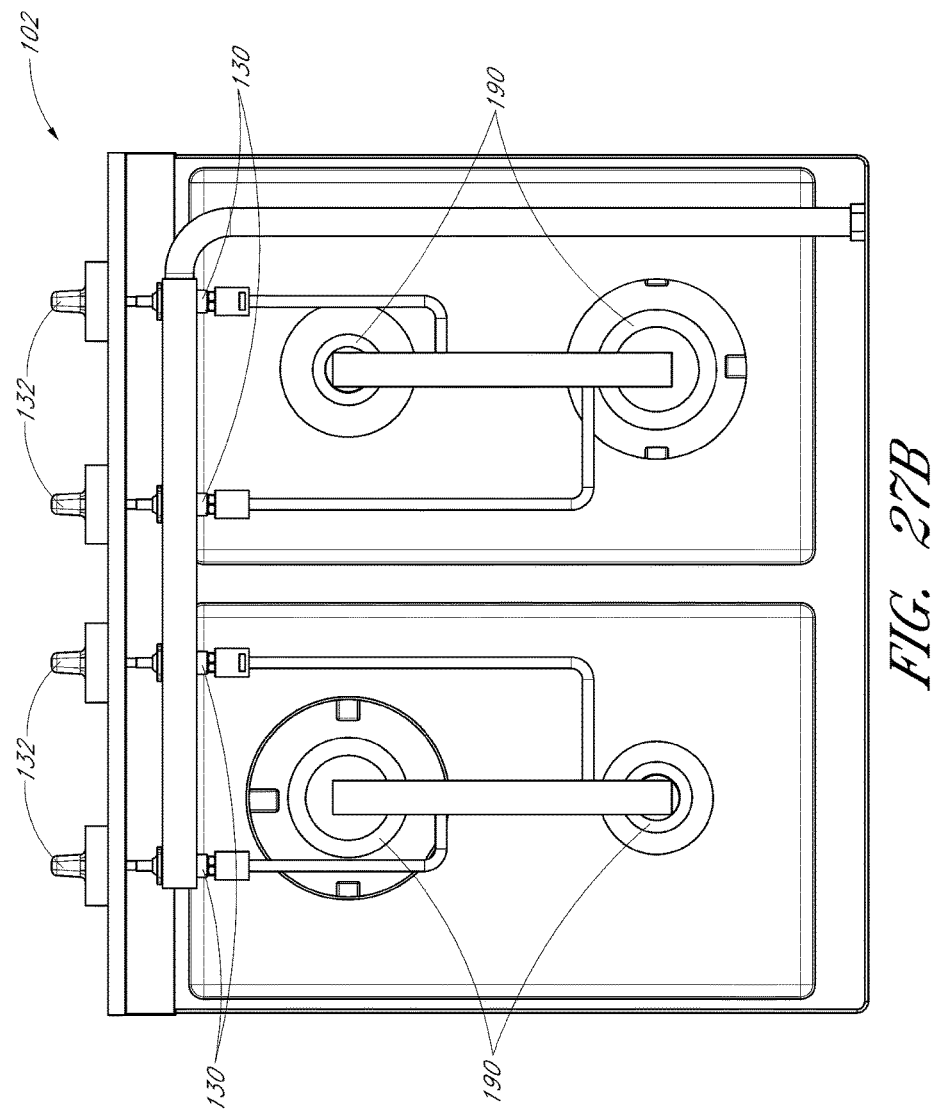

Two examples are shown in FIGS. 26A-27B. FIGS. 26A-B illustrate a barbeque grill 101 having a heating assembly utilizing the nozzle 160 and control valve 130 shown in FIG. 25A. The barbeque grill 101 is shown with three different types of burners, namely a side burner, an infrared burner, and a recessed burner. FIGS. 27A-B similarly show a gas stove top/range having a heating assembly utilizing the nozzle 160 and control valve 130 shown in FIG. 25A. The barbeque grill 101 and gas stove top can be dual fuel appliances. For example, they can be used with either propane or natural gas. If using propane, an external pressure regulator may also be used.

Returning now to FIGS. 25A-C, a control valve 130 can be connected to a nozzle 160. The nozzle 160 can be one of many different types of nozzles, including those discussed herein. The control valve 130 can have a knob or other control feature 132 to move a valve body 134 within the control valve housing 136 to the desired position. FIG. 25B shows two different internal valve bodies 134, 134' that could be used, though other configurations are also possible.

The first valve body 134 can be used to provide an "OFF" position and two "ON" positions. The two "ON" positions can be a high flow position and a low flow position. The flow of fuel into the control valve can be greater in the high flow position then in the low flow position. The valve body 134 can control the flow by providing two or more different size holes 138 through which the fuel can flow.

The second valve body 134' can be used to provide an "OFF" position and an "ON" position. The "ON" position can be adjustable to provide different amounts of fuel depending on the position of the valve body within the control valve housing. For example, the valve body 134' can have low and high positions and can be adjustable between those two positions. Thus, the amount of fuel flow can be adjusted to a desired setting that may include, low, high, medium, or something in-between those positions.

The different "ON" positions in the valve bodies 134, 134' can be facilitated by one or more holes or slots 138. The holes/slots can be different sizes, and/or can change size along their length. Valve body 134 has two different sized holes 138 and valve body 134' has a slot 138 that changes size along its length. The control valve housing 136 can have an inlet 135. The position of the valve body within the housing 136 determines whether the hole or slot 138 is in fluid communication with the inlet 135 and how much fuel can flow through the control valve 130.

The cross-section in FIG. 25C shows the control valve 130 in one of the "ON" positions. As has been discussed, the nozzle 160 shown is a pressure sensitive nozzle. The pressure sensitive nozzle can be single or dual stage. With a dual stage pressure sensitive nozzle, the pressure of the fluid flow opens the internal valve 12'. Independent of whether the pressure sensitive nozzle is dual stage or single stage, the pressure of the fluid flow controls whether the exit orifice 64 is open or closed and thereby controls the amount of flow through the nozzle.

For example, the nozzle 160 and control valve 130 can be set such that one fuel that flows at a known pressure opens the valve 12' and allows the exit orifice 64 to remain open while a second fuel opens the valve 12' yet closes the exit orifice 64. The second fuel flow would only pass through the exit orifices 66. The nozzle 160 and control valve 130 can be set so that this is the case independent of the position of the control valve 130. In other words, whether the control valve 130 is set to a high "ON" position or a low "ON" position the nozzle 160 would operate with a predetermined exit orifice configuration based on the type of fuel used (based on the expected pressure range of that fuel).

FIGS. 28-34B illustrate various additional embodiments of a nozzle 160. The nozzles are similar to the nozzle described above and illustrate additional ways that one or more orifices can be opened, closed or modified in a pressure sensitive manner.

Figure 28B:
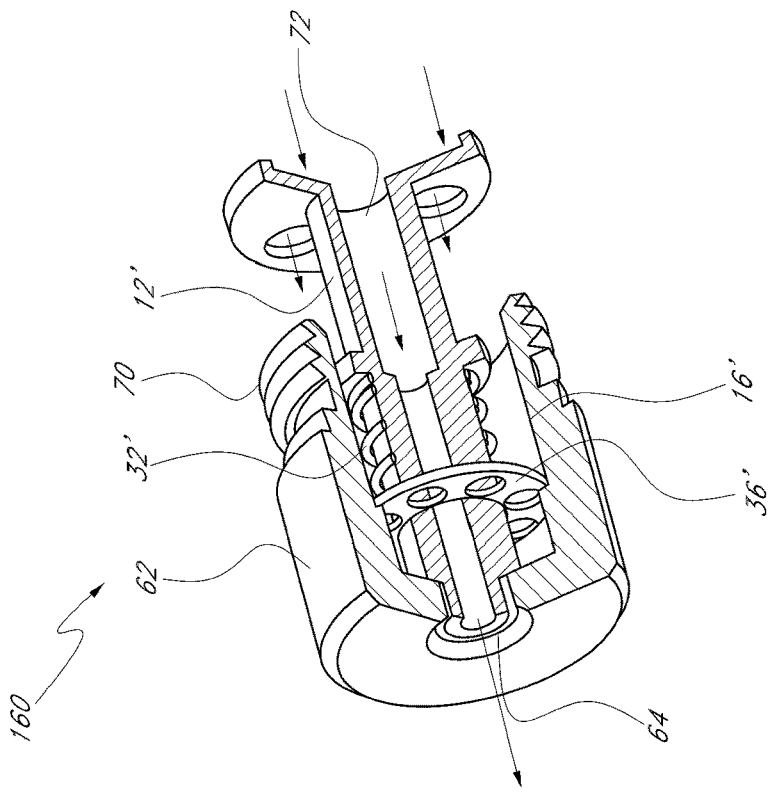
FIGS. 28A-B are sectional views of an embodiment of a nozzle in first and second positions, respectively.
Figure 28A:
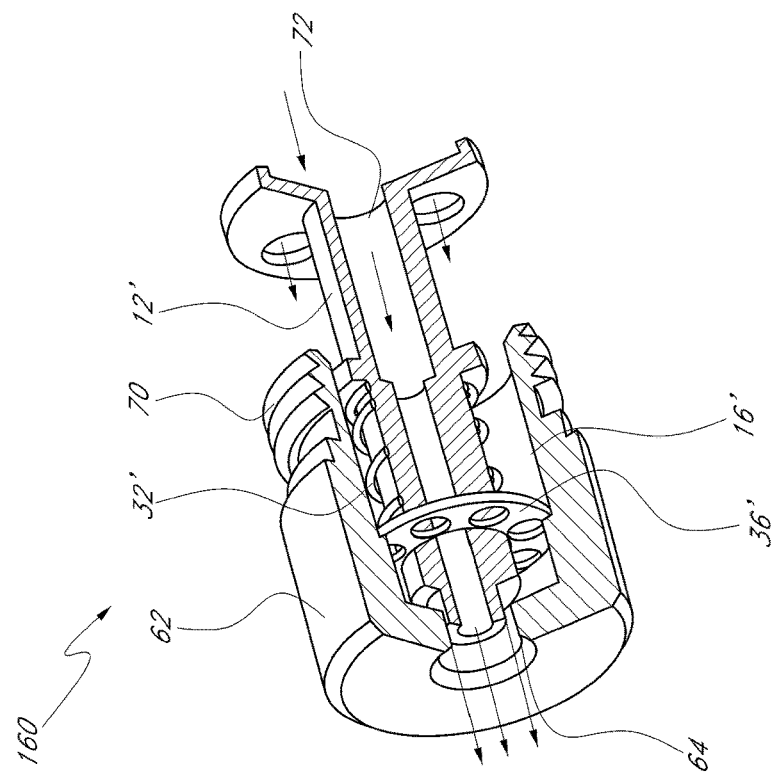

FIGS. 28A-B show a nozzle 160 with one orifice 64 and a channel 72 in the valve 12'. Fluid can flow around the through the valve 12'. As the pressure increases, the valve 12' can contact the orifice 64 and decrease the effective size of the orifice 64. For example, the valve 12 can contact and seal the orifice 64 such that only flow from the channel 72 can leave the nozzle 160 through the orifice. As the channel 72 can have a smaller diameter than the orifice 64, this can decrease the amount of fluid flow through the nozzle 160. In some embodiments, the valve 12' can fit inside the orifice 64 as shown (FIG. 28B).

Figure 29A:
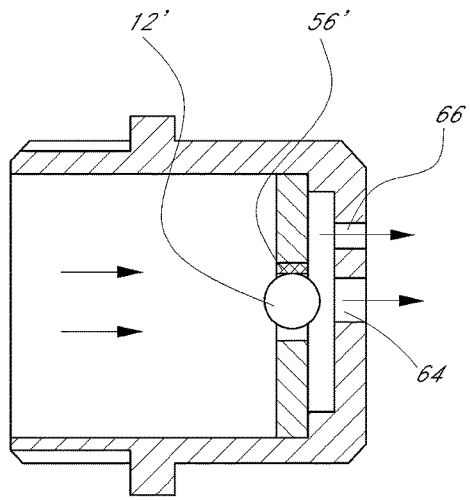
FIGS. 29A-B are schematic cross-sectional views of a nozzle in a first position and a second position.
Figure 29B:
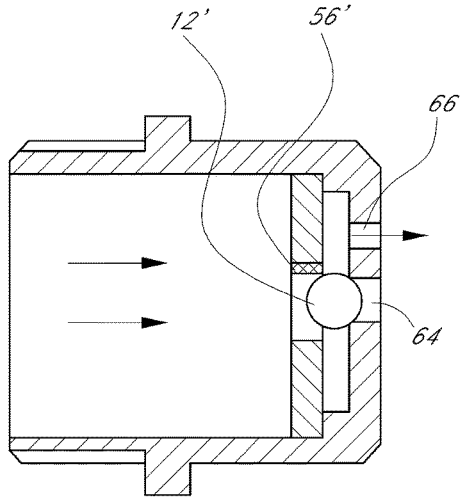
Figure 30A:
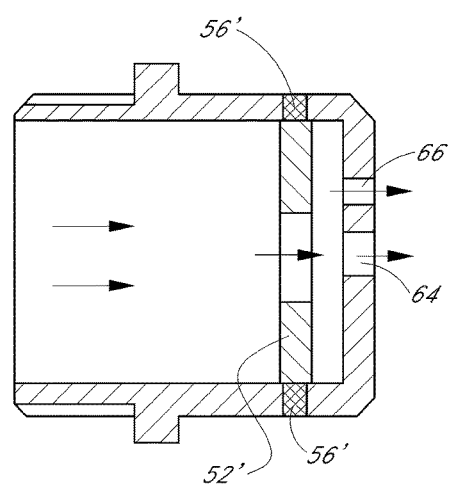
FIGS. 30A-B are schematic cross-sectional views of a nozzle in a first position and a second position.
Figure 30B:
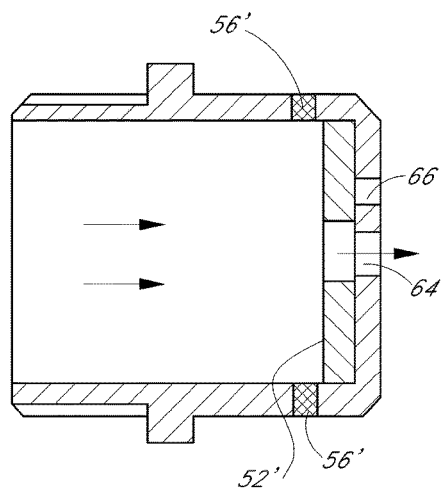

FIGS. 29A-32B all show additional nozzles 160 where the fluid flow at a certain pressure can dislodge or move another piece of material to block or close one or more exit orifices 64. FIGS. 29A-B show a steel ball 12' and a magnet 56'. FIGS. 30A-B show a force plate 52' and a magnet 56'. FIGS. 31A-B show a resilient gate 12'. FIGS. 32A-B show a force plate 52' and a magnet 56'. The arrows illustrate the fuel flow paths through the various nozzles.

Now looking to FIGS. 33A-D, another embodiment of a nozzle 160 is shown. The nozzle show can be pressure sensitive such that it can be used interchangeably with different fuels, but can also advantageously be self regulating while in use with a single fuel. This is because the nozzle can be configured such that the volume of fluid flowing through the nozzle can be directly related to the fluid pressure. In other words, the nozzle can be configured to control the flow such that as the pressure increases, the volume of fuel flowing through the nozzle decreases. Thus, for a fuel at a constant temperature, the nozzle can provide a varying volume of fuel as the pressure of the fuel fluctuates while maintaining a constant BTU value.

This is a result of the ideal gas law:

$$PV = nRT \qquad (1)$$

where "P" is the absolute pressure of the gas, "V" is the volume, "n" is the amount of substance; "R" is the gas constant, and "T" is the absolute temperature. Where amount and temperature remain constant, pressure and volume are inversely related. Thus, as the pressure increases, less volume of fuel is needed to provide the same amount of fuel. The amount is typically recorded in number of moles. A set number of moles of fuel will provide a particular BTU value. Therefore, the pressure sensitive nozzle shown in FIGS. 33A-D can advantageously provide a constant amount of fuel for a constant BTU value for a particular fuel, even as the fuel pressure fluctuates.

Figure 33A:
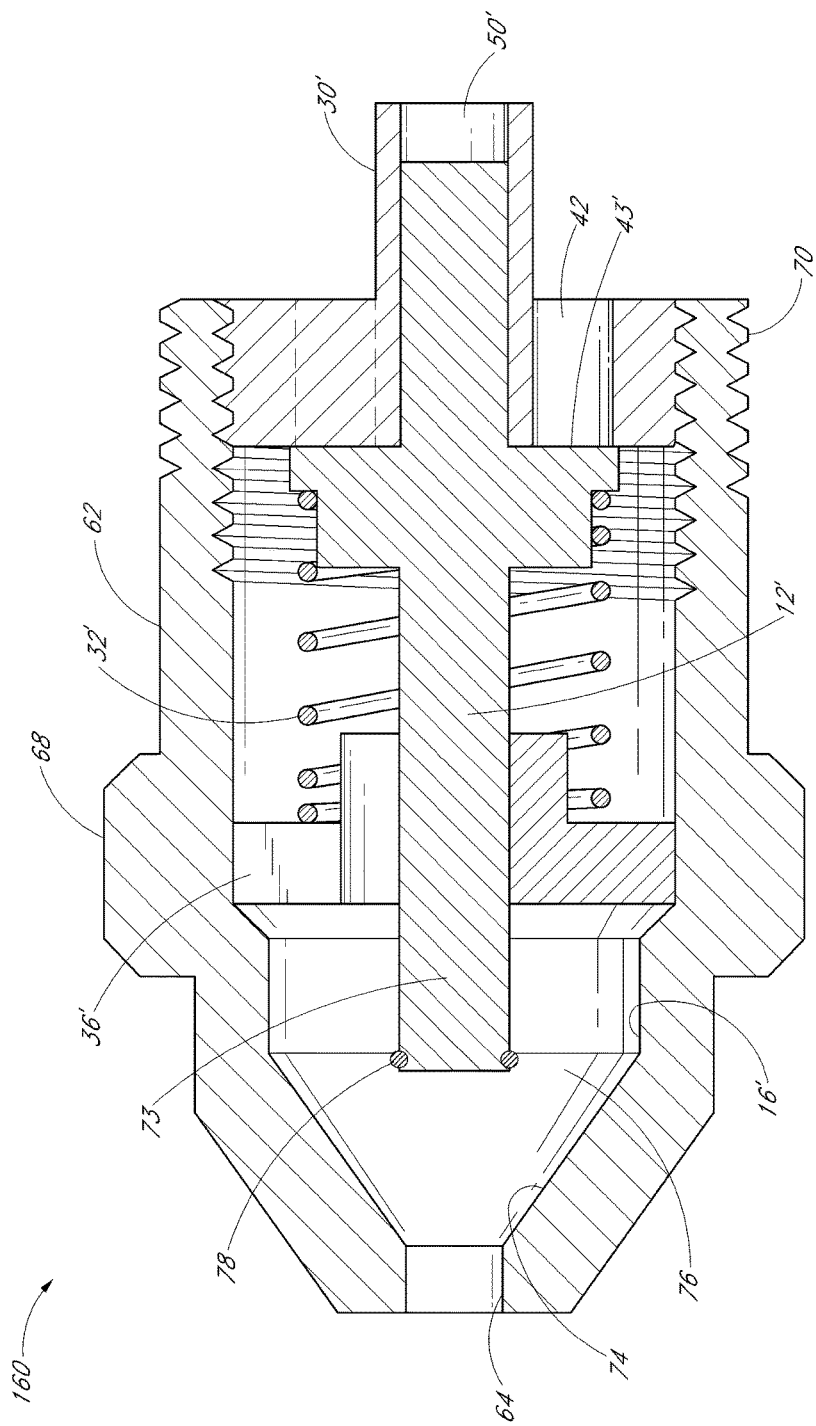
FIGS. 33A-D are sectional views of an embodiment of a nozzle in first, second, third and fourth positions, respectively.
Figure 33B:
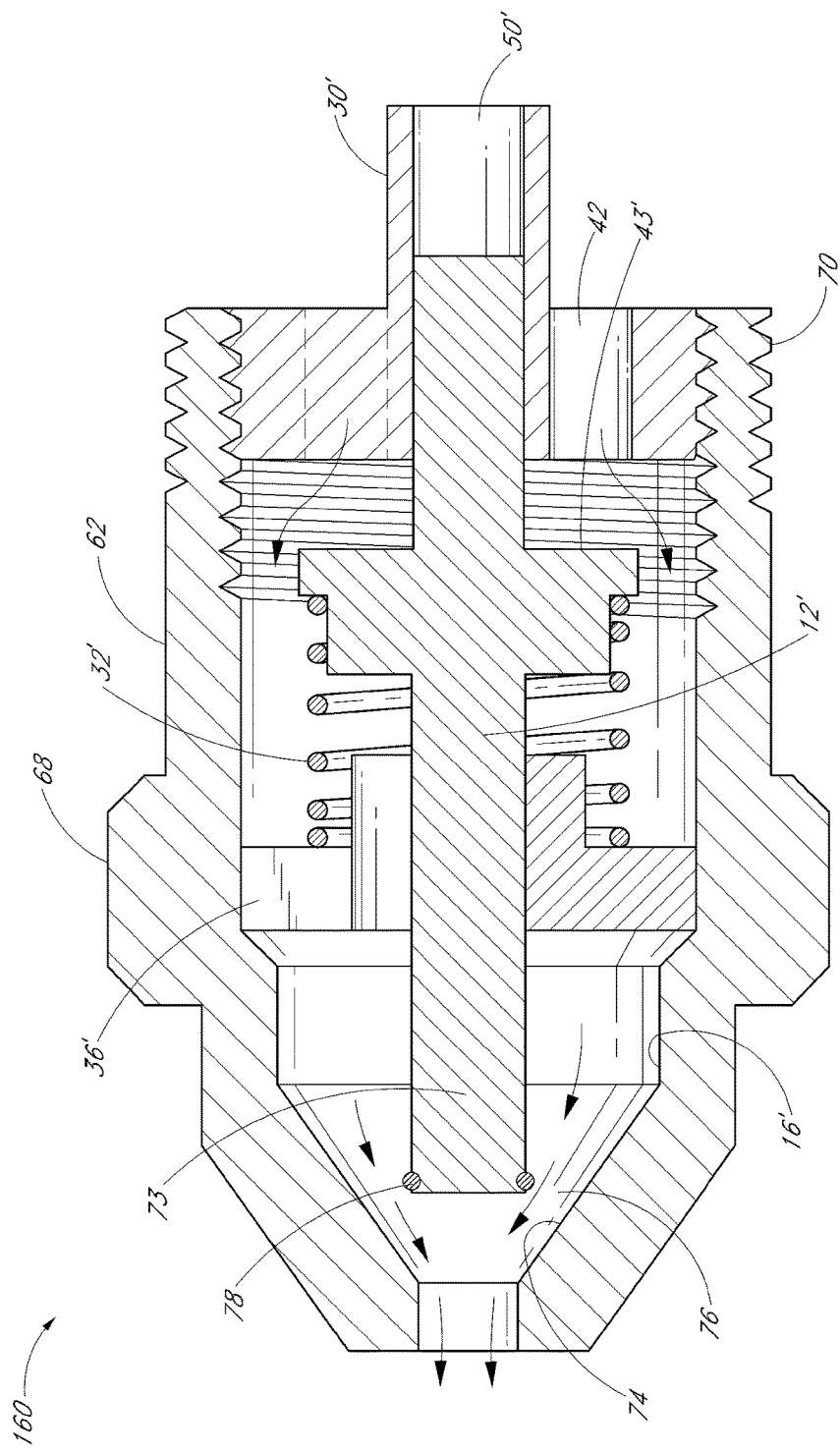
Figure 33C:
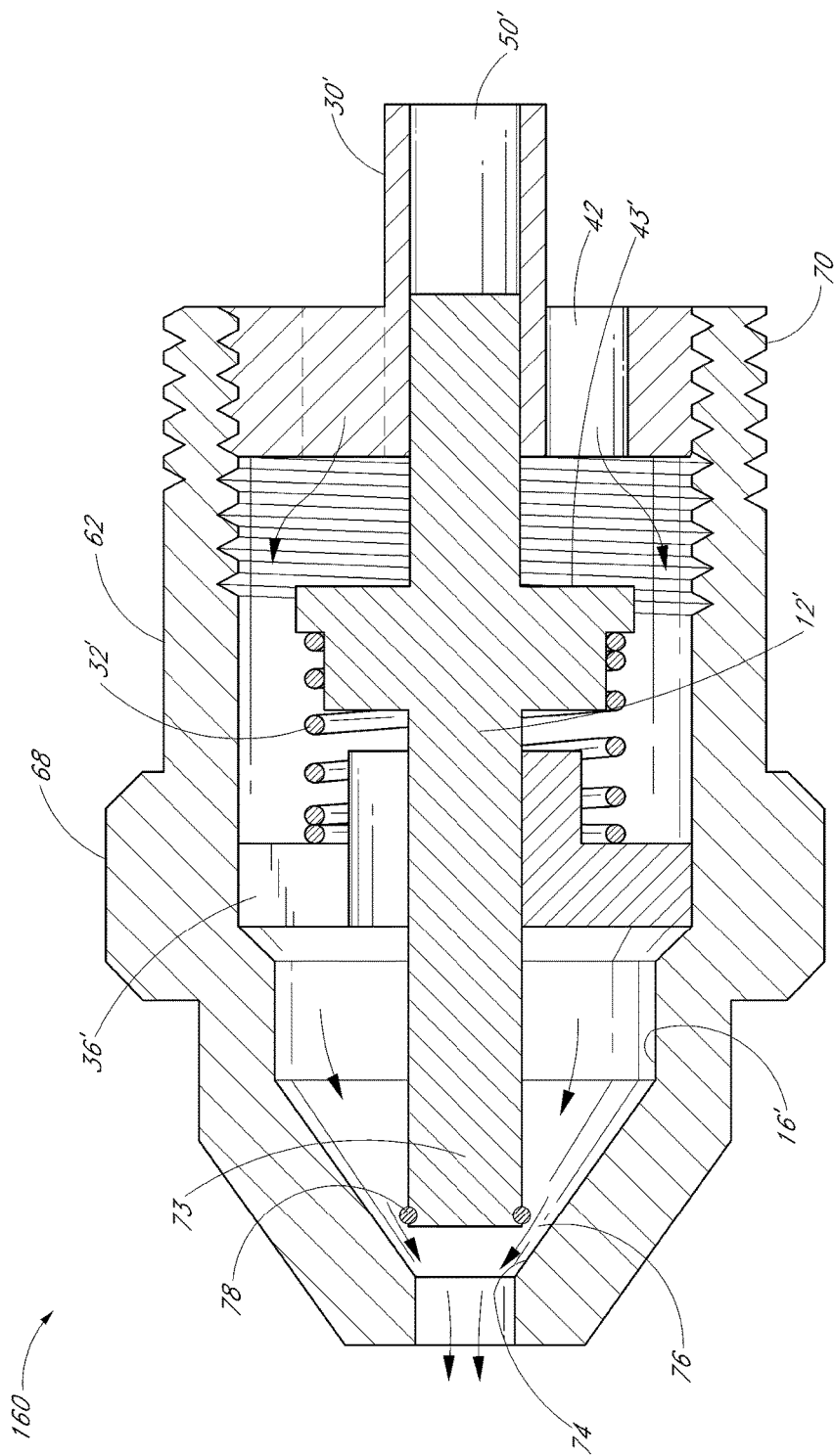
Figure 33D:
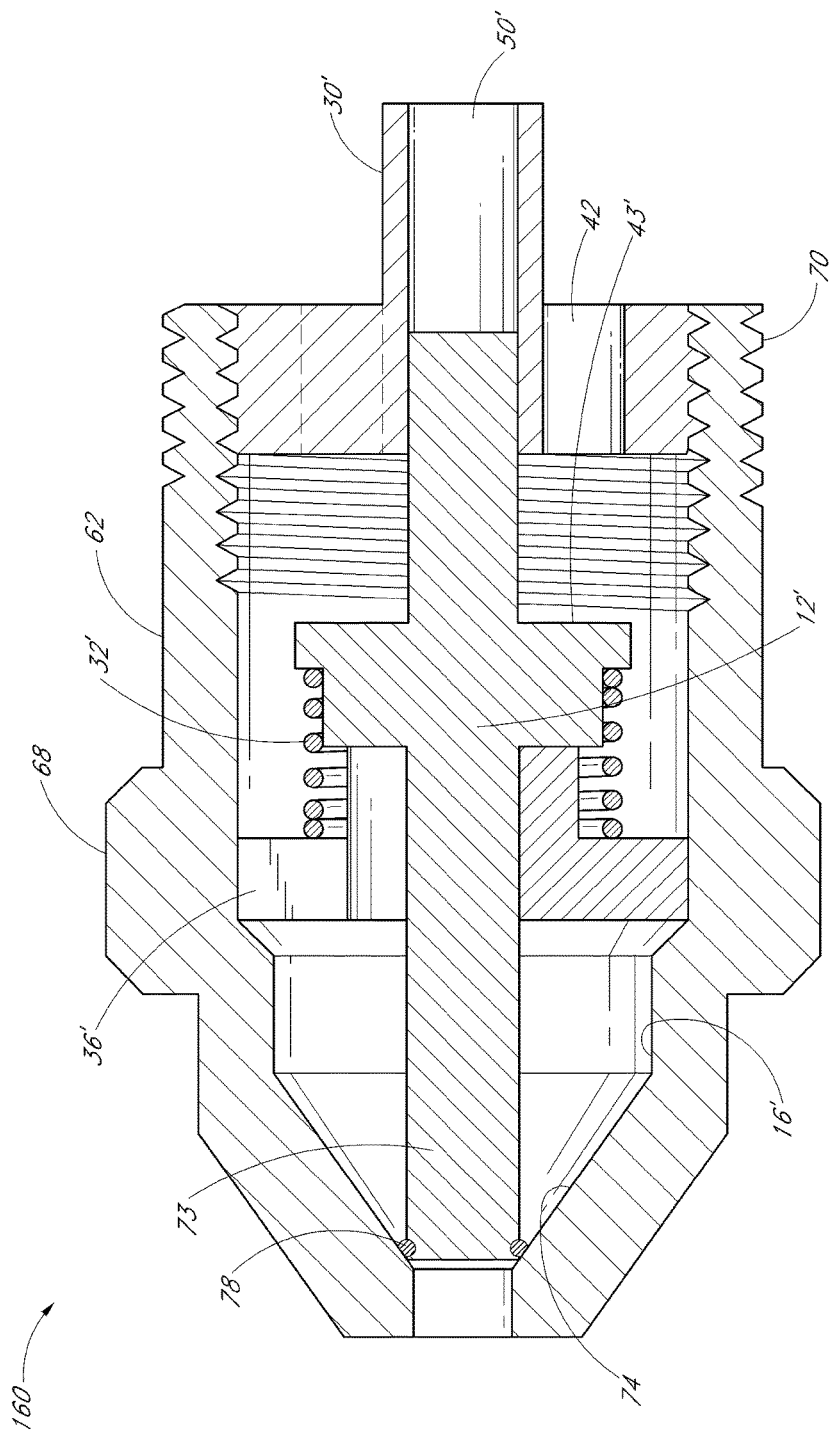

In some embodiments, the valve 12' can have an end 73 that cooperates with the internal chamber 16' to determine the volume of fluid that can flow through the valve 12'. For example, the valve end 73 can be cylindrical while a surface 74 of the internal chamber 16' can be frustoconical. Thus, as the cylinder valve end 73 approaches the frustoconical surface 74 the gap 76 between the two surfaces can slowly decrease, thus a smaller volume of fuel can pass through the gap 76. FIGS. 33A, B, C, and D illustrate how the gap can change as the pressure increases and the valve moves closer to the surface, until it contacts the surface and prevents flow through the valve 12'. In some embodiments, the valve end 73 includes a gasket 78 to sealingly close the gap 76.

In some embodiments, the nozzle 160 shown in FIGS. 33A-D can include one or more additional orifices 66. In some embodiments, the valve 12' can have a channel running through the valve 12' similar to that shown in FIGS. 28A-B.

In the various embodiments of valves, including those within a nozzle, adjustments can be made to calibrate the valve. For example, in FIGS. 33A-D, similar to the discussion with respect to the valve in FIG. 7A, the front portion 30' can be threadedly received into the interior of the nozzle. Calibrating the valve adjusts force required to move the valve 12' within the valve body or housing 62. This can be done in many ways, such as by adjusting the position of the valve 12' within the valve body or housing 62 and adjusting the compression or tension on a spring. Here, calibration can adjust the position of the valve body 12' in relation to the front portion 30' while adjusting the amount of force required to act on the spring to move the valve a desired amount. In the example of FIGS. 33A-D, the spring biases the valve to the closed position and adjusting the position of the front portion can increase or decrease the amount of pressure required to further compress the spring and open the valve to allow flow therethrough.

In some embodiments, the position of the rear portion 36', as well as, or in addition to the front portion 30' can be adjusted to calibrate the nozzle. For example, the rear portion 36' can be threadedly received into the interior of the nozzle. Further, the front and rear portions can be adjustable from either or both of inside and outside the housing 62. In some embodiments, the heating assembly can allow for calibration of one or more of the various valves without disassembly of the heating assembly.

Figure 34B:
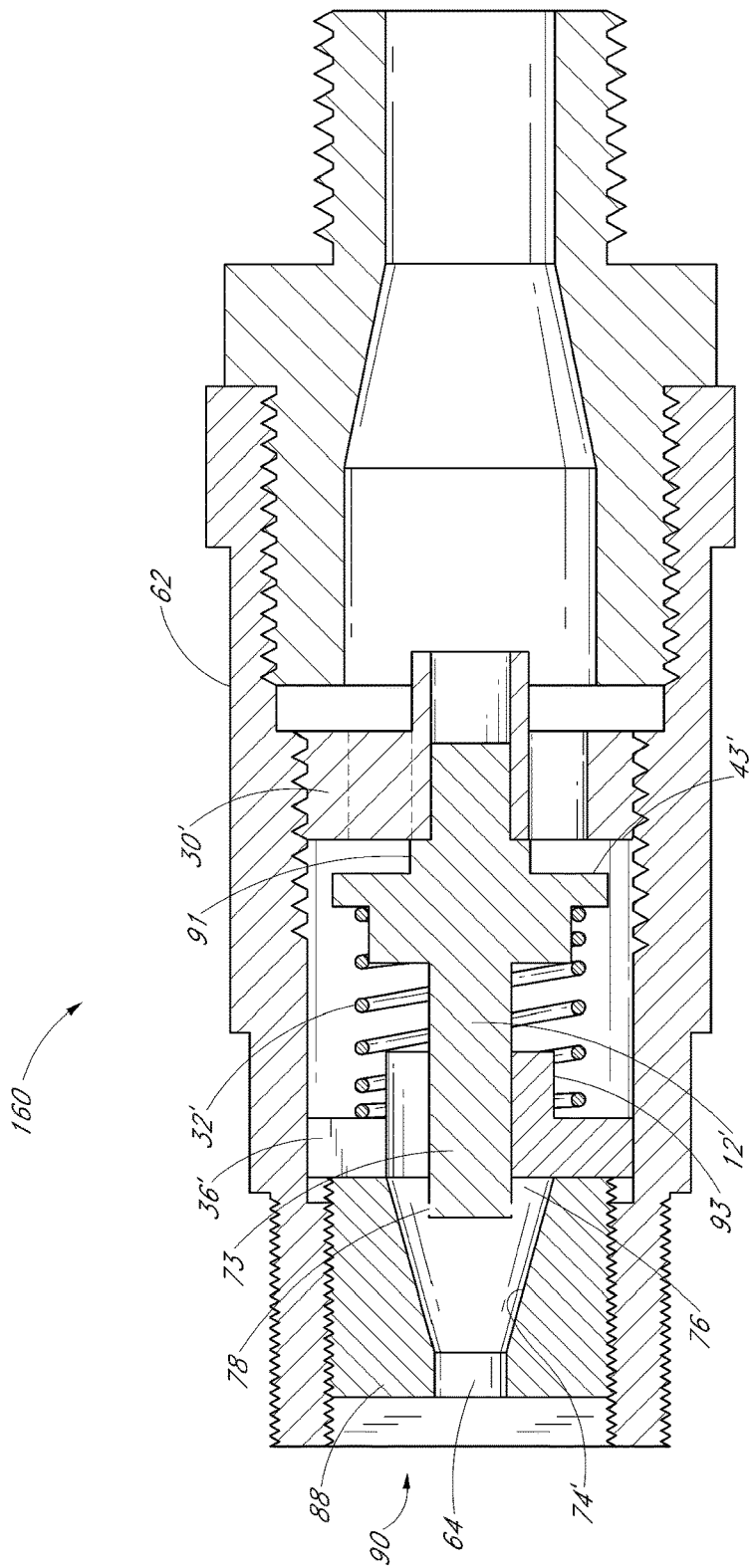

Turning now to FIGS. 34A-B, an embodiment of a nozzle 160 is shown. In this nozzle 160, the position of both the front 30' and rear 36' portions can be adjusted. Further, at least the position of the rear portion 36' can be adjusted from outside the nozzle body or housing 62. The nozzle 160 can comprise an adjustment feature 88. The adjustment feature 88 can be threadedly received into the housing. The adjustment feature 88 can comprise an end cap. The adjustment feature 88 can comprise a set screw. Adjustment of the position of the set screw can adjust the position of the rear portion 36' and the pressure of the spring 32' acting on the rear portion 36'. The set screw can have a detent 90, for example, to receive the head of a screw driver, Allen wrench or other tool. The tool can be used to adjust the position of the set screw from outside the nozzle housing 62. The set screw can include one or more holes that pass through the set screw. The one or more holes can comprise exit orifices 64, 66. As shown, the exit orifice 64 connects to the detent 90, other configurations are also possible. In some embodiments, the adjustment feature can be a part of the rear portion, or be integrally formed with the rear portion.

As illustrated, the adjustment feature 88 can have a frustoconical interior surface 74' similar to the valve interior of FIGS. 33A-D. The valve end 73 can cooperate with the surface 74' to determine the volume of fluid that can flow through the valve 12'. Thus, as the cylinder valve end 73 approaches the frustoconical surface 74' the gap 76 between the two surfaces can slowly decrease, thus a smaller volume of fuel can pass through the gap 76.

The adjustment feature 88 can also be used with other valves and/or nozzles, for example, the nozzles shown in FIGS. 23-25C, 28A-B. The adjustment feature 88 can also be used in such as way so as not to be within or form part of the flow path of fuel through the valve or nozzle.

FIG. 34B also illustrates two offsets 91, 93. The offset 91 can be used to prevent the valve 12' from contacting the front portion 30' in such a way as to close the valve completely at the front end. Offsets or similar structures can be used along the valve to prevent closing the valve on either or both of the front and the back sides of the valve. In some embodiments, an offset can be used with a single stage valve. Offsets can be part of the valve, or part of other structures. For example, the front or rear portion can include an offset. Offsets can also be used to ensure the valve does not move beyond a certain position. For example, an offset 93 can be used that allows the valve to close, but that prevents the valve from advancing farther, such as to prevent damage to the valve housing or housing wall.

Figure 35:
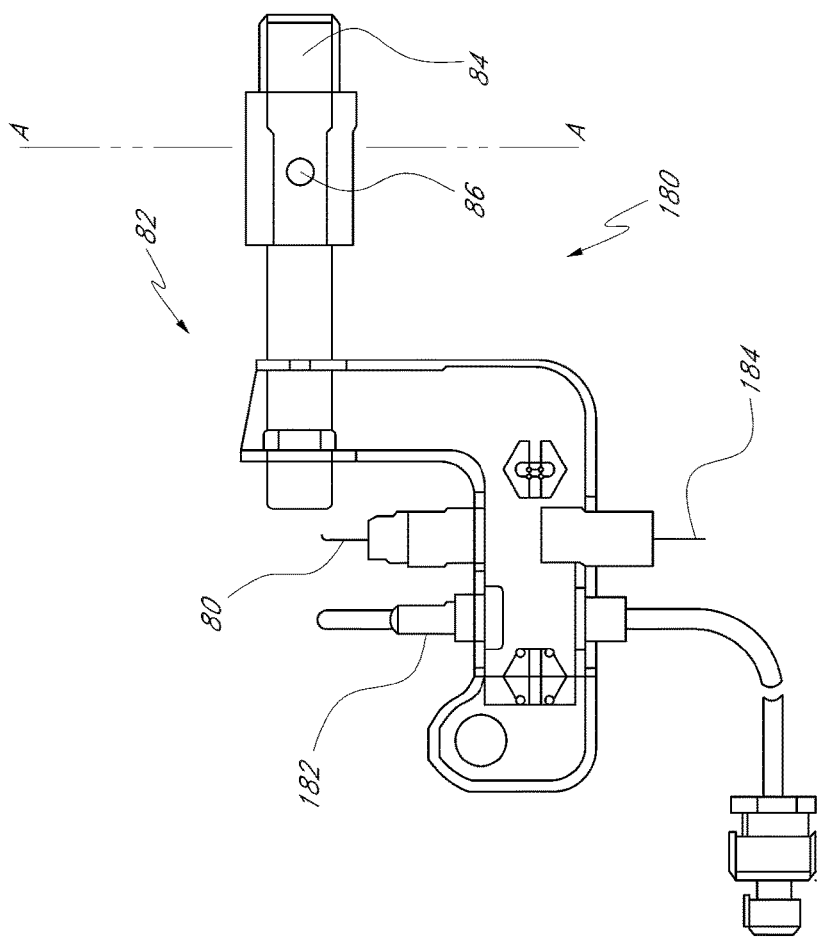
FIG. 35 shows an embodiment of an oxygen depletion sensor.

FIG. 35 shows one embodiment of an oxygen depletion sensor (ODS) 180. An ODS 180 or pilot light (not shown) can include a nozzle similar to the burner nozzles 160 shown and/or described herein and can be used in some heating assemblies.

The ODS 180 shown includes a thermocouple 182, an electrode 80 and an ODS nozzle 82. The ODS nozzle 82 can include an injector 84 and an air inlet 86. A fuel can flow from the ODS line 143 through the ODS nozzle 82 and toward the thermocouple 182. The fuel flows near the air inlet 86, thus drawing in air for mixing with the fuel.

In some embodiments, the injector 84 can be a pressure sensitive injector and can include any of the features of the pressure sensitive nozzles described herein. For example, the exit orifices 64 and/or 66 can be located along line A-A of FIG. 35 within the ODS nozzle 82. The air inlet 86 can also be adjustable so that the air fuel combination is appropriate for the particular type of fuel used.

The electrode 80 can be used to ignite fuel exiting the ODS nozzle 82. In some embodiments, a user can activate the electrode 80 by depressing the igniter switch 186 (see FIG. 2). The electrode can comprise any suitable device for creating a spark to ignite a combustible fuel. In some embodiments, the electrode is a piezoelectric igniter. Igniting the fluid flowing through the nozzle 82 can create a pilot flame. In preferred embodiments, the nozzle 82 directs the pilot flame toward the thermocouple such that the thermocouple is heated by the flame, which permits fuel to flow through the control valve 130.

In various embodiments, the ODS 180 provides a steady pilot flame that heats the thermocouple 182 unless the oxygen level in the ambient air drops below a threshold level. In certain embodiments, the threshold oxygen level is between about 18 percent and about 18.5 percent. In some embodiments, when the oxygen level drops below the threshold level, the pilot flame moves away from the thermocouple, the thermocouple cools, and the control valve 130 closes, thereby cutting off the fuel supply to the heater.

Figure 36A:
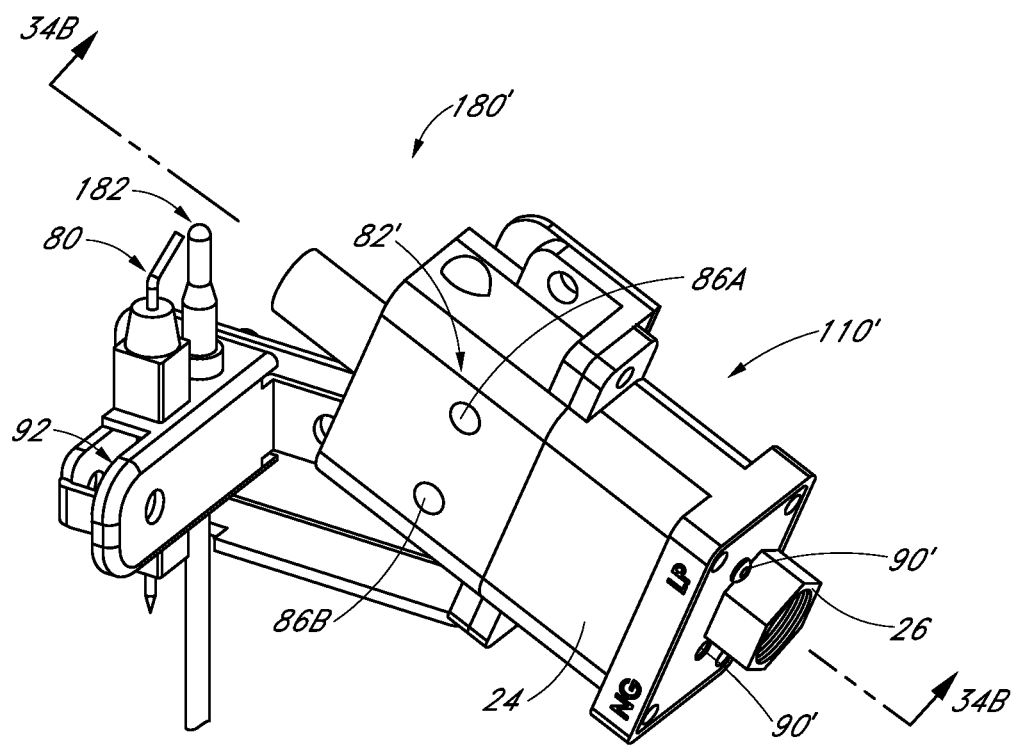
FIGS. 36A-B show perspective and cross sectional views of an oxygen depletion sensor.

FIGS. 36A-38B show various additional embodiments of an ODS. The ODS can include or can be connected to a valve. The valve can be user selectable or pressure selectable. For example, FIGS. 36A-B illustrate an ODS 180' connected to a pressure selectable valve 110' similar to that shown in FIGS. 6-7C. Any of the pressure selectable valves shown here connected to an ODS can also be used to connect to a pressure regulator or other component of a heating assembly. In addition, other types of user selectable or pressure selectable valves can also be connected to an ODS.

Figure 36B:
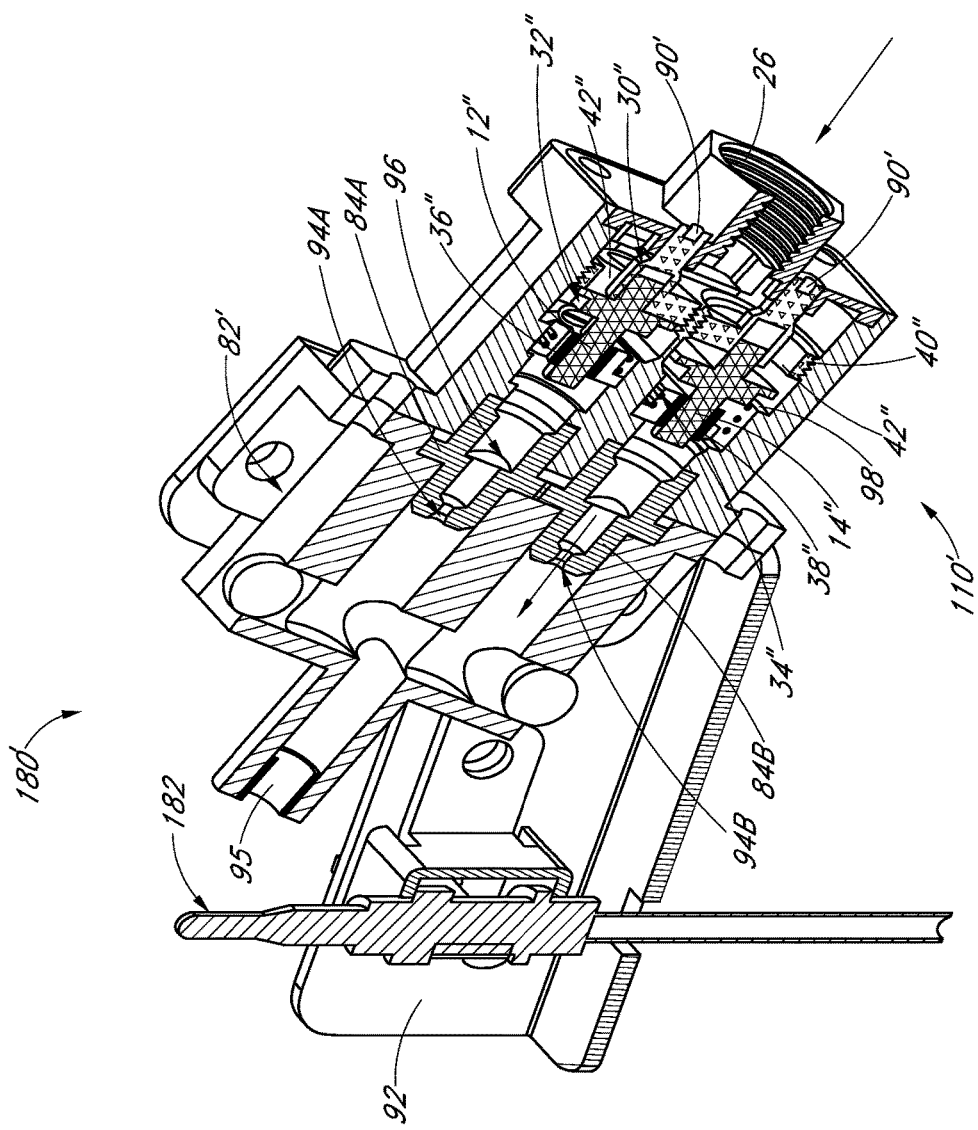

Referring first to FIGS. 36A-B, an ODS 180' with pressure selectable valve 110' is shown. The ODS 180' can include a thermocouple 182, an electrode 80, a mounting bracket 92, and an ODS nozzle 82'. The ODS nozzle 82' can include injectors 84A, 84B and air inlets 86A, 86B. The injectors can each have an exit orifice 94A, 94B. The exit orifices 94A, 94B can the same or different sizes. The air inlets 86A, 86B can also be the same or different sizes, and in some embodiments are adjustable.

The valve 110' can be similar to those described herein, such as that in FIGS. 6-7C. The valve 110' can allow for at least two different flow paths through the valve depending on the pressure of the flow. The valve 110' can include a main housing 24, a fuel source connection or inlet 26, valves 12", 14", biasing members 32", 34", front portions 30", 40" and rear portions 36", 38".

Looking to FIG. 36B, a first flow path is shown indicated by the arrows. Fuel at a first pressure can then pass through valve 14" into injector 84B and thereby fuel can flow through the ODS. In a dual stage configuration, the fuel at the first pressure can also cause valve 14" to open, while valve 12" remains closed to allow the fuel to flow through the valve 110'. When fuel at a higher pressure is introduced into the valve 110', the higher pressure fuel can cause the valve 14" to close by contacting the interior surface of the valve 110' at 98. Valve 12" can be opened by the higher pressure fuel which can then direct the flow to injector 84A and thereby higher pressure fuel can flow through the ODS. The ODS can have one outlet 95 (FIGS. 36A-B), or two outlets 95 (FIGS. 37A-38B). The outlets can direct fuel towards the thermocouple.

In some embodiments with two outlets 95, the outlets can be located the same or different distances away from the thermocouple. Also, the ODS can include one or more thermocouples 182 and igniters 80. In some embodiments, the ODS can have one or more flame directors 97. The flame directors 97 can be used to position the flame in a predetermined relationship to the thermocouple. Further, the embodiments shown in FIGS. 37A-B and FIGS. 38A-B including at least some of these features will be understood as functioning in a similar manner to the description of FIGS. 36A-B.

Figure 37A:
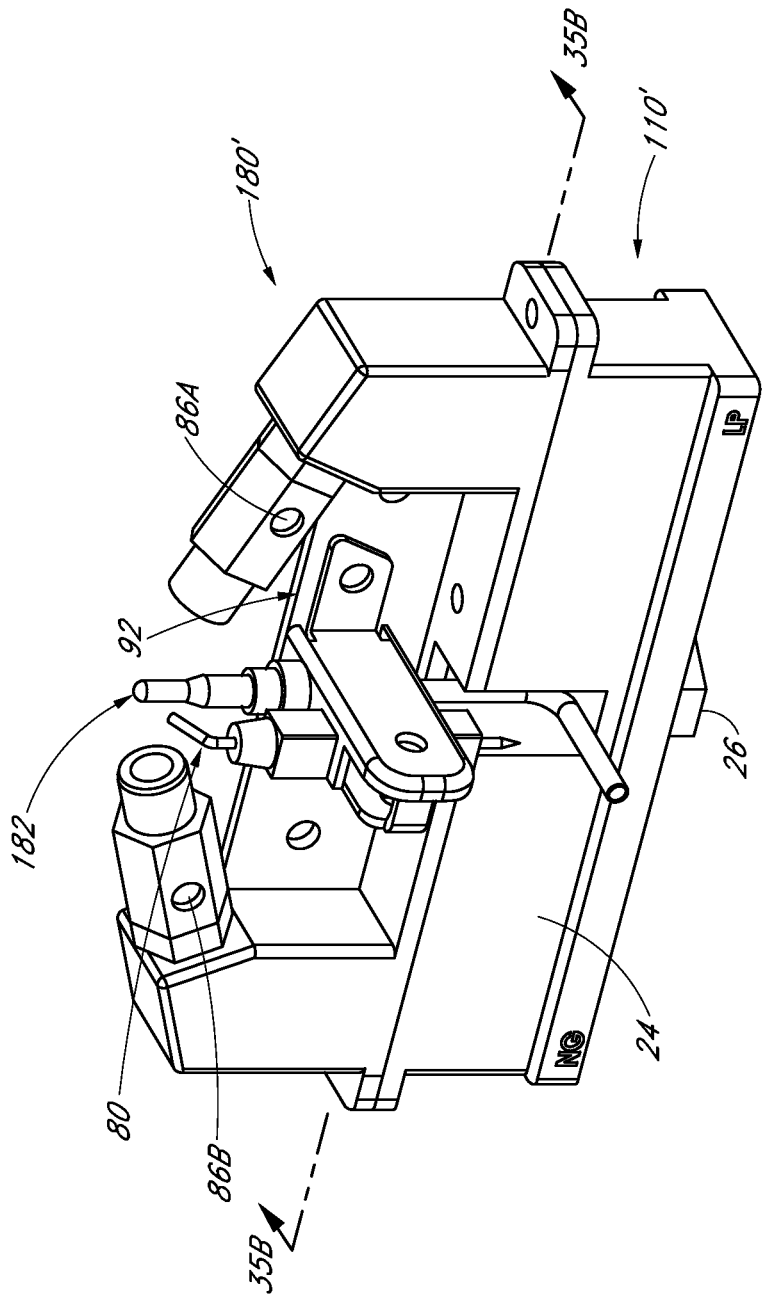
FIGS. 37A-B show perspective and cross sectional views of an oxygen depletion sensor.
Figure 37B:
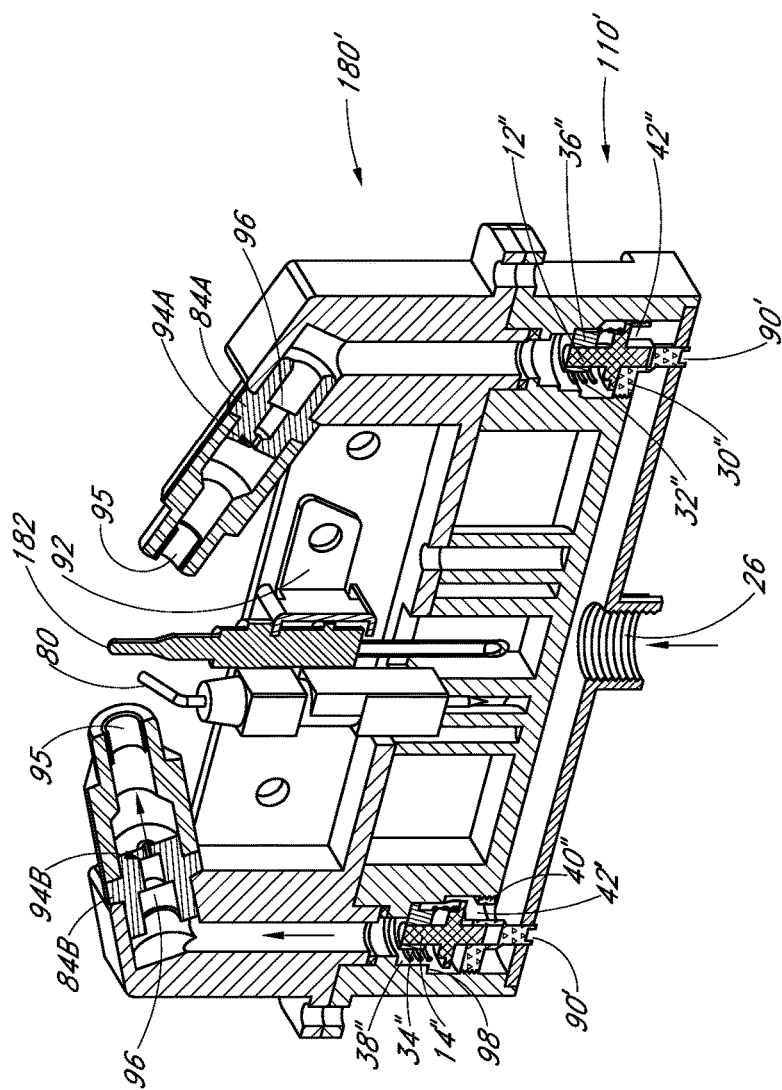
Figure 38A:
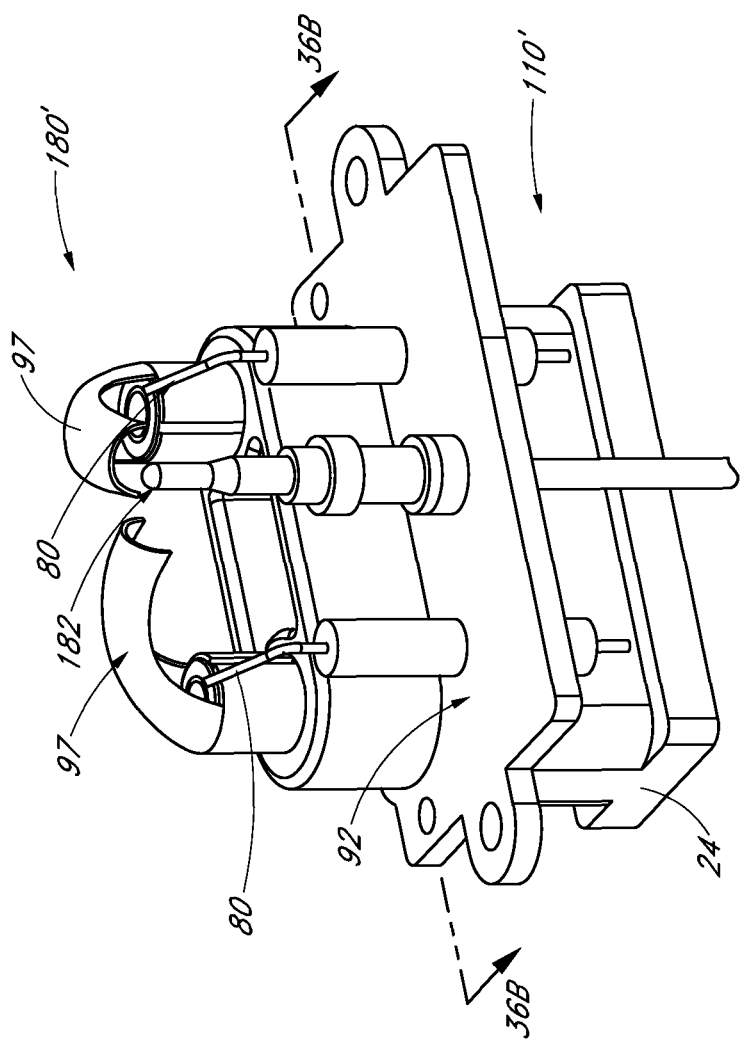
FIGS. 38A-B show perspective and cross sectional views of an oxygen depletion sensor.
Figure 38B:
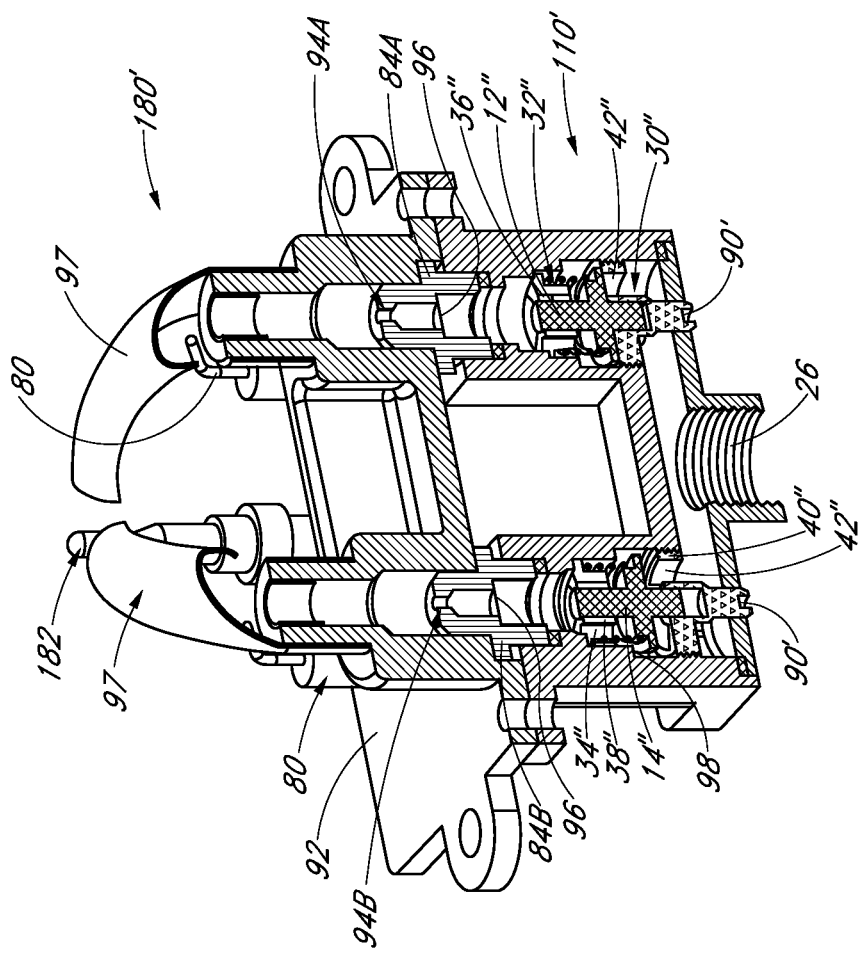

A filter 96 can be included anywhere along the fuel flow path within the heating assembly. As shown in FIGS. 36B, 37B and 38B, a filter 96 is within the injectors 84A, 84B. The filter can filter out impurities in the fuel flow.

In some embodiments, the valve 110' can allow for calibration of the valves 12", 14" from outside the housing. The front portions 30", 40" can pass through the housing 24 and can include a detent 90'. The detent can be used to adjust the position of the front portion within the valve 110'. For example, the detent 90' can receive the head of a screw driver, Allen wrench or other tool to adjust the position of the front portion.

Turning now to FIGS. 39A-B and 40A-C, two additional embodiments of a nozzle 160 are shown. The nozzle 160 is a pressure sensitive nozzle similar to that described previously. As has also been mentioned previously, various features (such as the internal valve) of the nozzles 160 shown and described can also be used in other components, such as in fuel selector valves, and ODSs.

Figure 39A:
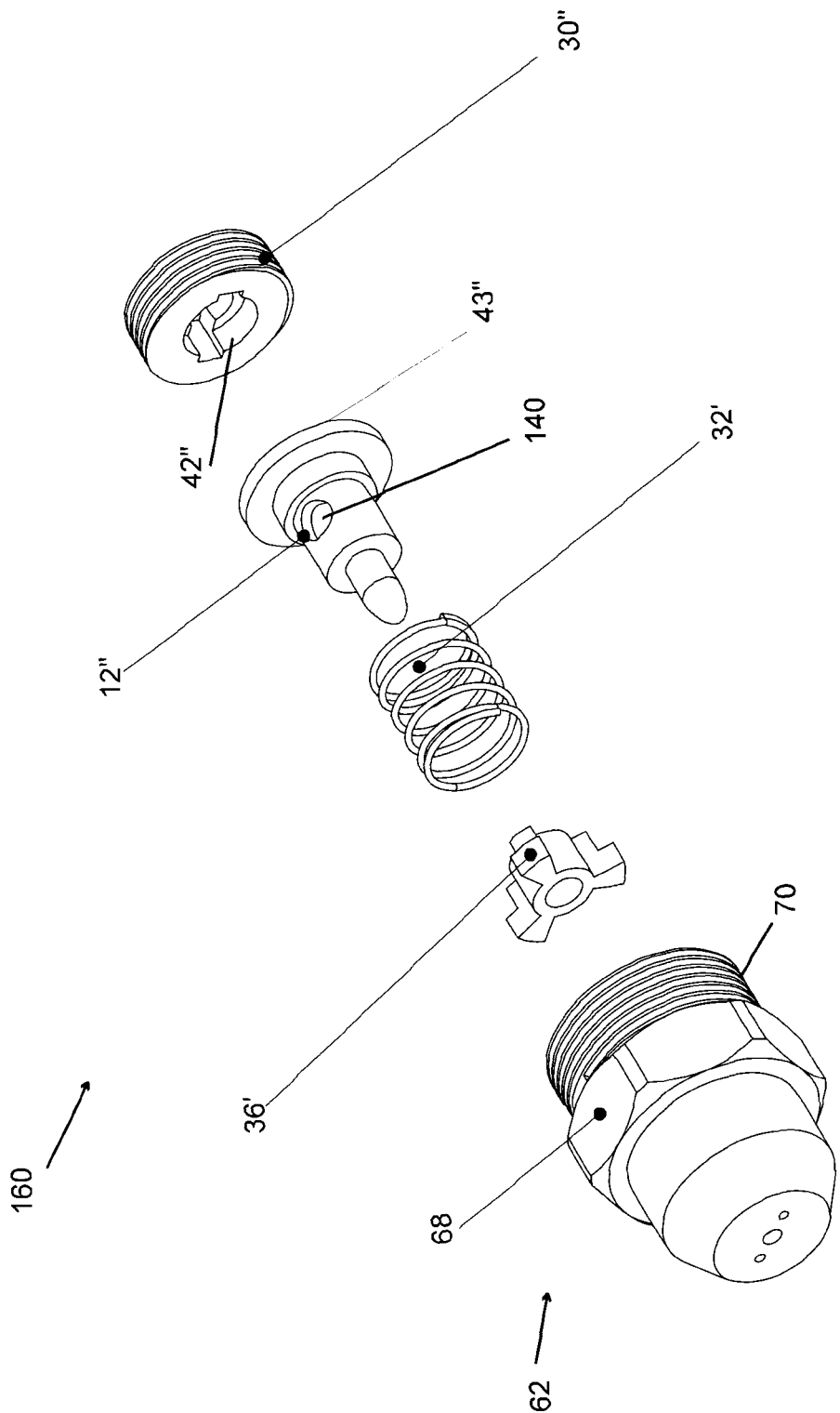
FIG. 39A illustrates an exploded view of an embodiment of a nozzle.
Figure 39B:
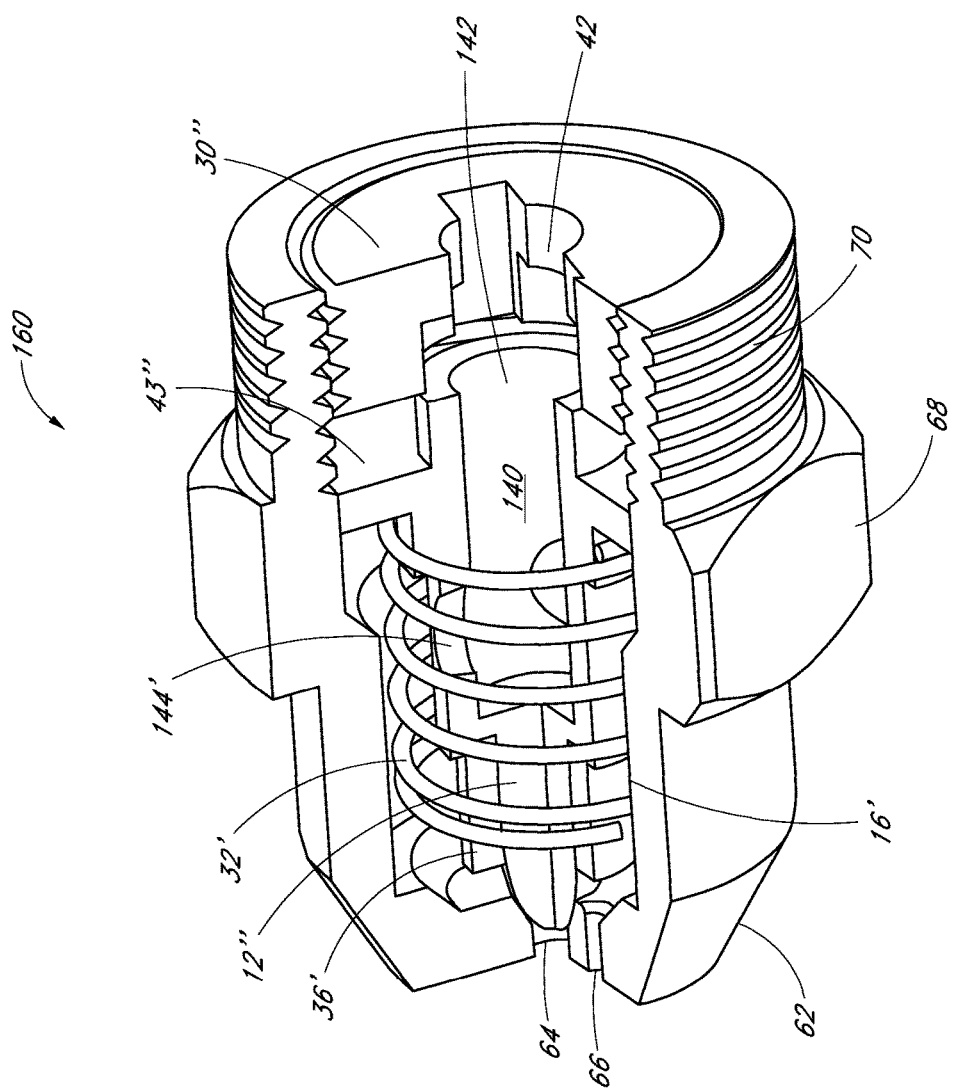
FIG. 39B shows a partial cross section of the nozzle of FIG. 39A.

Referring first to FIGS. 39A-B, the nozzle 160 includes a front portion 30", a valve 12", a spring 32', and a rear portion 36', all of which can be positioned inside a nozzle body 62. The nozzle body 62 can be a single piece or a multi-piece body and can include a flange 68 and threads 70.

The spring 32' can be a single stage or a dual stage spring. As shown, the spring 32' is a single stage spring and is configured to move from a first position to a second position at a set pressure. In the second position, the valve 12" can reduce or block flow through the nozzle 160. As shown in FIG. 39B, flow through orifice 64 can be blocked by the valve 12", while one or more orifices 66 remain open. In this way, the nozzle can function in a manner similar to those previously described.

The valve 12" can have a passage 140 through which fluid, such as fuel, can pass. The passage 140 can have an inlet 142 and an outlet 144. As shown, there is one inlet 142 and two outlets 144, though any number of inlets and outlets can be used. The passage can be in central region or can direct fluid to or through a central region of the valve 12". The valve 12" can also include a front ledge 43". The front ledge 43" and the passage 140 can be used to direct all, or a substantial portion, of the fluid flow through the valve 12" and can increase the forces acting on the valve to reliably open and/or close the valve.

Figure 40A:
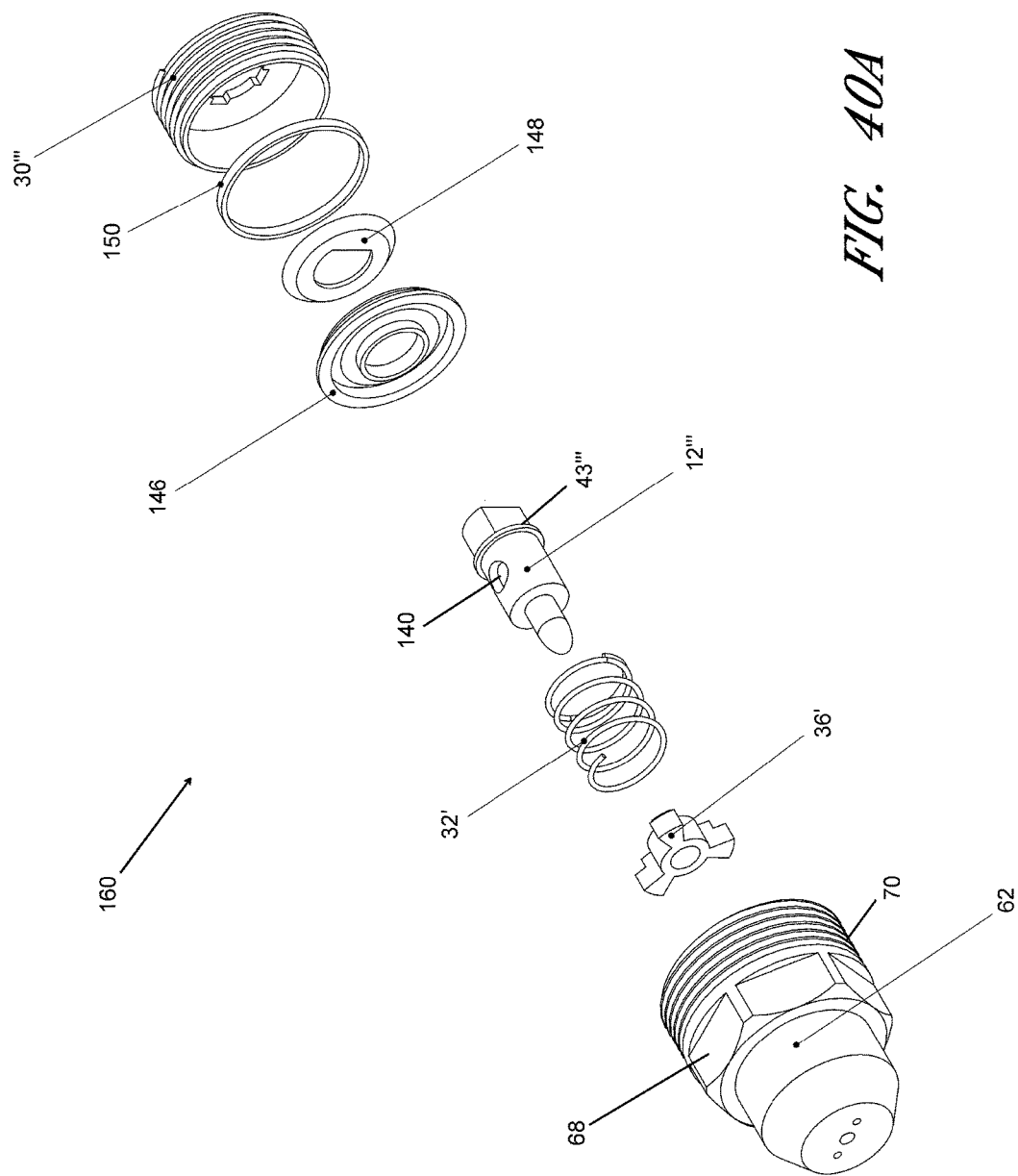
FIG. 40A illustrates an exploded view of an embodiment of a nozzle.
Figure 40B:
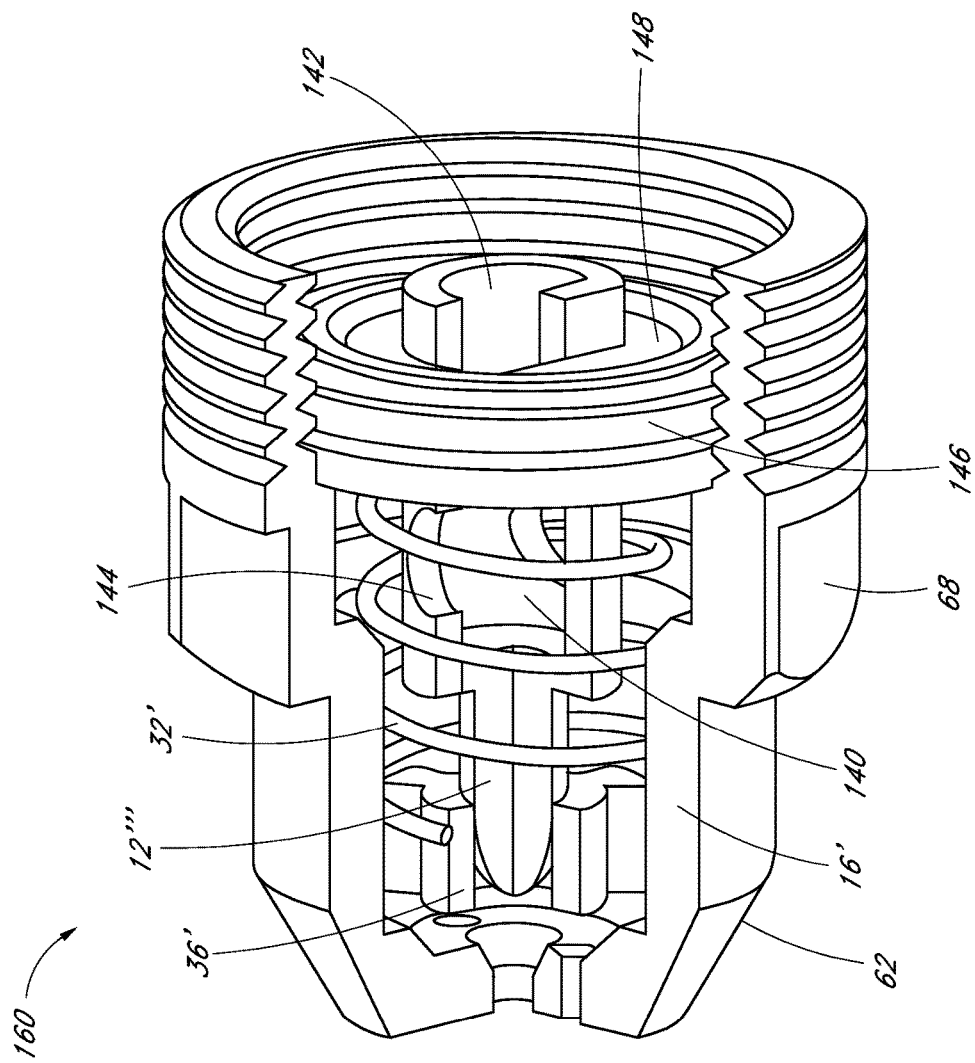
FIG. 40B is a partial cross section of the nozzle of FIG. 40A.
Figure 40C:
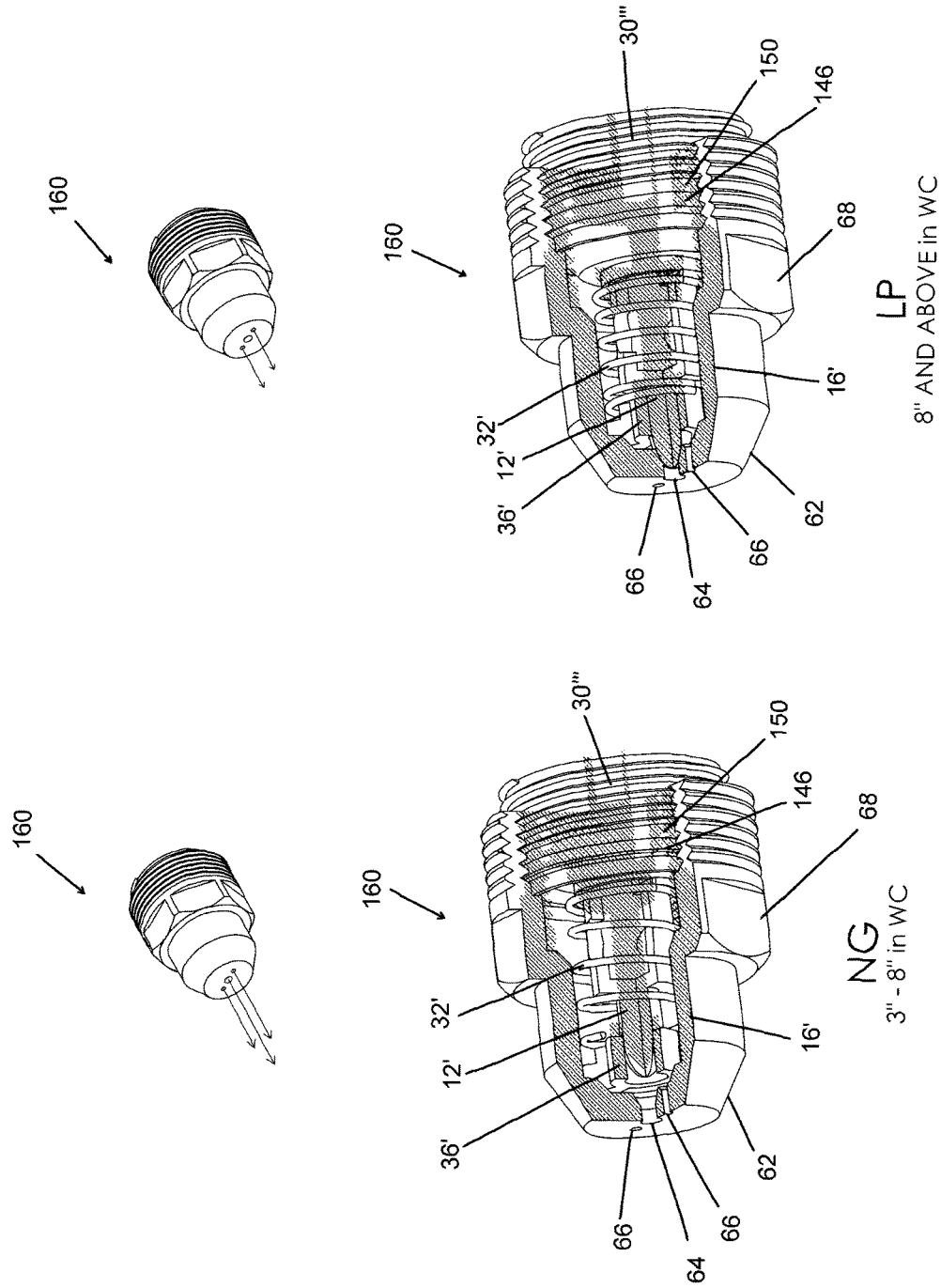
FIG. 40C shows the nozzle of FIG. 40A in a first position and a second position.

Turning now to FIGS. 40A-C another variation of the nozzle 160 is shown. The valve 12''' also has a passage 140 with an inlet 142 and an outlet 144. The front ledge 43''' of the valve 12''' can be used to connect a diaphragm 146 and a diaphragm retainer 148 to the valve 12'''. The nozzle 160 can also include a washer 150 and a front portion 130'''. The diaphragm retainer can be force fit or otherwise secured onto the valve 12'''. This can allow the diaphragm 146, the diaphragm retainer 148, and the valve 12''' to move together. Other configurations to connect a diaphragm to the valve 12''' can also be used.

The front portion 130''' can secure the washer 150 and diaphragm 146 in place within the nozzle. For example, in the cross section of FIG. 40B the front portion 30''' is not shown, but can be used to secure the washer 150 and diaphragm 146 in place at the location in the nozzle shown.

The diaphragm 146 can act as a spring force and in some embodiments can replace the spring 32'. In some embodiments, the spring 32' can serve to return the diaphragm 146 to an initial position. In some embodiments, the diaphragm can be set to allow the valve 12''' to move at a set fluid pressure, such as at 8 inches water column, or other pressures as has been described herein with reference to other valves. In some embodiments, the diaphragm can be made from various materials including silicone and/or rubber.

FIG. 40C shows the valve 12''' in two different positions, such as at an initial position at a lower pressure and the second position at a higher pressure. At the higher pressure the hole 64 can be closed by the valve 12'''.

The valves 12" and 12''' can advantageously have an increased surface area that is exposed to the fluid flowing through the nozzle. This increased exposure can lead to increased repeatability and reliability of the nozzle under different flow circumstances. The increased surface area can help ensure that the valve sealingly closes the hole 64. Having the fluid flow through the valve and in particular, flow through the central region of the valve can focus the fluid pressure in the center of the valve. As the hole 64 is aligned with the center of the valve focusing the fluid pressure at the center of the valve can increase the reliability of the valve, sealing the hole at increased pressures. In addition, the diaphragm has the added benefit of regulating the gas pressure similar to a typical pressure regulator. This can beneficially provide additional fluid pressure regulation throughout a heater system.

In some embodiments, a fuel selector valve and/or an ODS can also have a valve with a passage therethrough and/or a diaphragm.

Advantageously, certain embodiments of the heating assembly as described herein facilitates a single appliance unit being efficaciously used with different fuel sources. This desirably saves on inventory costs, offers a retailer or store to stock and provide a single unit that is usable with more than one fuel source, and permits customers the convenience of readily obtaining a unit which operates with the fuel source of their choice.

Advantageously, certain embodiments of the heating assembly can transition between the different operating configurations as desired with relative ease and without or with little adjustment by an installer and/or an end user. Preferably, a user does not need to make a fuel selection through any type of control or adjustment. The systems described herein can alleviate many of the different adjustments and changes required to change from one fuel to another in many prior art heating sources.

It will be understood that the embodiments and components described herein can be used with, without and/or instead of other embodiments and components as described herein or otherwise. For example, the fuel selector valve described herein can be connected to the regulator 120 of the heater 100 shown in FIGS. 1 and 2.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures or characteristics of any embodiment described above may be combined in any suitable manner, as would be apparent to one of ordinary skill in the art from this disclosure, in one or more embodiments.

Similarly, it should be appreciated that in the above description of embodiments, various features of the inventions are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A dual fuel oxygen depletion sensor comprising:
   a housing having a single inlet and a single outlet, and having a first fluid flow path and a second fluid flow path through the housing between the inlet and the outlet;
   a first air intake;
   a second air intake;
   a first injector within the housing and defining part of the first fluid flow path, the first injector comprising a first orifice, the first orifice configured to direct a first fuel from the inlet and towards the outlet while drawing air into the housing through the first air intake;
   a second injector within the housing and defining part of the second fluid flow path, the second injector comprising a second orifice, the second orifice configured to direct a second fuel from the inlet and towards the outlet while drawing air into the housing through the second air intake, wherein the first fuel is at a first pressure different from a second pressure of the second fuel;
   a first valve within the housing and defining part of the first fluid flow path, the first valve configured to control a flow of the first fuel to the first injector; and
   a second valve within the housing and defining part of the second fluid flow path, the second valve configured to control a flow of the second fuel to the second injector.

2. The dual fuel oxygen depletion sensor of claim 1, the first orifice comprising a first hole sized differently from a second hole comprising the second orifice.

3. The dual fuel oxygen depletion sensor of claim 1, the first air intake comprising a first hole sized differently from a second hole comprising the second air intake.

4. The dual fuel oxygen depletion sensor of claim 1, wherein the first valve is configured to open at the first pressure and close at the second pressure, and wherein the second valve is configured to open at the second pressure and close at the first pressure.

5. The oxygen depletion sensor of claim 4, further comprising a first biasing member configured to open the first valve by a first predetermined fluid pressure acting on the first valve, the first predetermined fluid pressure being insufficient to open the second valve.

6. The oxygen depletion sensor of claim 5, further comprising a second biasing member configured to open the second valve by a second predetermined fluid pressure acting on the second valve, wherein each of the first and second biasing members comprise at least one of a spring and a diaphragm.

7. The oxygen depletion sensor of claim 1, further comprising a thermocouple and an igniter.

8. The oxygen depletion sensor of claim 1, further comprising an adjustable valve seat configured to calibrate the first valve.

9. A heating system comprising the dual fuel oxygen depletion sensor of claim 1, and a gas valve configured to direct fuel to the dual fuel oxygen depletion sensor, wherein the heating system is part of a water heater, a fireplace, a gas oven, a stove, a BBQ, or a gas dryer.

10. The dual fuel oxygen depletion sensor of claim 1, wherein at least one of the first and second air intakes comprise a hole of an adjustable size.

* * * * *